US009508937B2

(12) United States Patent
Jenekhe et al.

(10) Patent No.: US 9,508,937 B2
(45) Date of Patent: Nov. 29, 2016

(54) ACENAPHTHYLENE IMIDE-DERIVED SEMICONDUCTORS

(71) Applicant: University of Washington through its Center for Commercialization, Seattle, WA (US)

(72) Inventors: Samson A. Jenekhe, Seattle, WA (US); Haiyan Li, Seattle, WA (US); Felix Sunjoo Kim, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/420,886

(22) PCT Filed: Aug. 21, 2013

(86) PCT No.: PCT/US2013/055984
§ 371 (c)(1),
(2) Date: Feb. 10, 2015

(87) PCT Pub. No.: WO2014/031750
PCT Pub. Date: Feb. 27, 2014

(65) Prior Publication Data
US 2015/0243906 A1    Aug. 27, 2015

Related U.S. Application Data

(60) Provisional application No. 61/692,167, filed on Aug. 22, 2012.

(51) Int. Cl.
*H01L 51/00* (2006.01)
*C07D 221/18* (2006.01)
(Continued)

(52) U.S. Cl.
CPC ......... *H01L 51/0072* (2013.01); *C07D 221/18* (2013.01); *C07D 471/06* (2013.01);
(Continued)

(58) Field of Classification Search
CPC ............ H01L 51/0072; C07D 221/18; C07D 471/06; C07D 495/16; C07D 519/00; C08G 61/122; C08G 61/126
See application file for complete search history.

(56) References Cited

U.S. PATENT DOCUMENTS

| 6,046,342 A | 4/2000 | Jung |
| 2007/0160905 A1 | 7/2007 | Morishita |

(Continued)

FOREIGN PATENT DOCUMENTS

| CN | 102782011 A | 11/2012 |
| EP | 2 493 960 A0 | 9/2012 |

(Continued)

OTHER PUBLICATIONS

Barattin, R., et al., "Synthesis of Two Complementary Molecular Moulds," Eur. J. Org. Chem. 2009, 1022-1026.*

(Continued)

*Primary Examiner* — Liam J Heincer
*Assistant Examiner* — Nicholas Hill
(74) *Attorney, Agent, or Firm* — Christensen O'Connor Johnson Kindness PLLC

(57) ABSTRACT

Novel acenaphthylene imide-derived semiconductor materials, including small molecule compounds, polymers and oligomers. Also provided are methods for making the novel semiconductor materials and the use of the novel semiconducting materials in electronic or optoelectronic device. In some embodiments, the novel semiconducting materials are used as n-channel component in organic field-effect transistors as well as complementary electronic circuits including inverters. High mobility can be achieved.

22 Claims, 7 Drawing Sheets

(51) Int. Cl.
| | |
|---|---|
| C07D 471/06 | (2006.01) |
| C07D 471/22 | (2006.01) |
| C07D 495/16 | (2006.01) |
| C07D 519/00 | (2006.01) |
| C08G 61/12 | (2006.01) |
| C09K 11/06 | (2006.01) |
| H01L 51/05 | (2006.01) |
| H01L 51/44 | (2006.01) |

(52) U.S. Cl.
CPC ............ *C07D471/22* (2013.01); *C07D 495/16* (2013.01); *C07D 519/00* (2013.01); *C08G 61/122* (2013.01); *C08G 61/126* (2013.01); *C09K 11/06* (2013.01); *H01L 51/0036* (2013.01); *H01L 51/0039* (2013.01); *H01L 51/0043* (2013.01); *H01L 51/0053* (2013.01); *H01L 51/0068* (2013.01); *H01L 51/0071* (2013.01); *C08G 2261/12* (2013.01); *C08G 2261/18* (2013.01); *C08G 2261/3142* (2013.01); *C08G 2261/3223* (2013.01); *C08G 2261/3241* (2013.01); *C08G 2261/3243* (2013.01); *C08G 2261/61* (2013.01); *C08G 2261/92* (2013.01); *C09K 2211/1033* (2013.01); *C09K 2211/1077* (2013.01); *C09K 2211/1081* (2013.01); *C09K 2211/1085* (2013.01); *H01L 51/0026* (2013.01); *H01L 51/0545* (2013.01); *H01L 51/0558* (2013.01); *H01L 51/44* (2013.01)

(56) References Cited

U.S. PATENT DOCUMENTS

| | | |
|---|---|---|
| 2011/0101276 A1 | 5/2011 | Rybtchinski |
| 2011/0136333 A1 | 6/2011 | Facchetti |
| 2012/0152357 A1 | 6/2012 | Brown et al. |
| 2012/0255615 A1 | 10/2012 | Sellinger et al. |
| 2012/0273732 A1 | 11/2012 | Jenekhe et al. |

FOREIGN PATENT DOCUMENTS

| | | | |
|---|---|---|---|
| WO | 2009/126203 | A1 | 10/2009 |
| WO | 2010/011658 | A2 | 1/2010 |
| WO | 2011/051292 | A1 | 5/2011 |
| WO | 2013/096924 | A1 | 6/2013 |
| WO | 2013/102038 | A1 | 7/2013 |
| WO | 2014/031750 | A1 | 2/2014 |
| WO | 2015/038671 | A2 | 3/2015 |

OTHER PUBLICATIONS

Yu, M., et al., "Self-assembly of Hydrogen-bonded Chains of Molecular Landers," Chem. Commun., 2010, 46, 5545-5547.*
Anthony, J.E., et al., "n-Type Organic Semiconductors in Organic Electronics," Advanced Materials 22(34):3876-3892, Aug. 2010.
Duan, L., et al., "Novel Naphthalimide Derivatives With Near-Infrared Emission: Synthesis via Photochemical Cycloaromatization. Fluorescence in Solvents and Living Cell," Tetrahedron Letters 50(1):22-25, Jan. 2009.
Herrera, H., et al., "Linear and Star-Shaped Naphthalimide-Fused Pyrazinacenes," Chemical Communications 49(7):713-715, Jan. 2013.
International Preliminary Report on Patentability mailed Feb. 24, 2015, issued in corresponding International Application No. PCT/US2013/055984, filed Aug. 21, 2013, 1 page.
International Search Report and Written Opinion mailed Dec. 4, 2013, issued in corresponding International Application No. PCT/US2013/055984, filed Aug. 21, 2013, 12 pages.
International Search Report and Written Opinion mailed Mar. 4, 2015, issued in corresponding International Application No. PCT/US2014/055030, filed Sep. 10, 2014, 9 pages.
Li, H., et al., "High-Mobility n-Type Conjugated Polymers Based on Electron-Deficient Tetraazabenzodifluoranthene Diimide for Organic Electronics," Journal of the American Chemical Society 135(40):14920-14923, Oct. 2013.
Li, H., et al., "Tetraazabenzodifluoranthene Diimides: Building Blocks for Solution-Processable n-Type Organic Semiconductors," Angewandte Chemie 52(21):5513-5517, May 2013.
Pho, T.V., et al., "Self-Assembling Decacyclene Triimides Prepared through a Regioselective Hextuple Friedel-Crafts Carbamylation," Angewandte Chemie 52(5):1446-1451, Jan. 2013.
Ponce Ortiz, R., et al., "Molecular and Electronic-Structure Basis of the Ambipolar Behavior of Naphthalimide-Terthiophene Derivatives: Implementation in Organic Field-Effect Transistors," Chemistry 19(37):12458-12467, Sep. 2013.
Ponce Ortiz, R., et al., "Organic n-Channel Field-Effect Transistors Based on Arylenediimide-Thiophene Derivatives," Journal of the American Chemical Society 132(24):8440-8452, Jun. 2010.
Ren, G., et al., "Non-Fullerene Acceptor-Based Bulk Heterojunction Polymer Solar Cells: Engineering the Nanomorphology via Processing Additives," Advanced Energy Materials 1(5):946-953, Oct. 2011.
Reusch, W., "Virtual Textbook of Organic Chemistry," Jun. 2010, <http://www2.chemistry.msu.edu/faculty/reusch/VirtTxtJml/intro1.htm> [retrieved May 2, 2016], 4 pages.
Roncali, J., et al., "From One- to Three-Dimensional Organic Semiconductors: In Search of the Organic Silicon?" Advanced Materials 19(16):2045-2060, Aug. 2007.
Sariciftci, N.S., et al., "Photoinduced Electron Transfer From a Conducting Polymer to Buckminsterfullerene," Science 258(5087):1474-1476, Nov. 1992.
Schwenn, P.E., et al., "A Small Molecule Non-Fullerene Electron Acceptor for Organic Solar Cells," Advanced Energy Materials 1(1):73-81, Jan. 2011.
Shaheen, S.E., et al., "2.5% Efficient Organic Plastic Solar Cells," Applied Physics Letters 78(6):841-843, Feb. 2011.
Small, C.E., et al., "High-Efficiency Inverted Dithienogermole-Thienopyrrolodione-Based Polymer Solar Cells," Nature Photonics 6(2):115-120, Feb. 2012.
Sonar, P., et al., "Organic Non-Fullerene Acceptors for Organic Photovoltaics," Energy & Environmental Science 4(5):1558-1574, May 2011.
Stille, J.K., "The Palladium-Catalyzed Cross-Coupling Reactions of Organotin Reagents With Organic Electrophiles," Angewandte Chemie 25(6):508-524, Jun. 1986.
Stolar, M., and T. Baumgartner, "Organic n-Type Materials for Charge Transport and Charge Storage Applications," Physical Chemistry Chemical Physics 15(23):9007-9024, Jun. 2013.
Subramaniyan, S., et al., "Effects of Side Chains on Thiazolothiazole-Based Copolymer Semiconductors for High Performance Solar Cells," Advanced Energy Materials 1(5):854-860, Oct. 2011.
Subramaniyan, S., et al., "New Thiazolothiazole Copolymer Semiconductors for Highly Efficient Solar Cells," Macromolecules 44(16):6245-6248, Aug. 2011.
Sun, Y., et al., "Inverted Polymer Solar Cells Integrated With a Low-Temperature-Annealed Sol-Gel-Derived ZnO Film as an Electron Transport Layer," Advanced Materials 23(14):1679-1683, Apr. 2011.
Sun, Z., et al., "Soluble and Stable Zethrenebis(dicarboximide) and Its Quinone," Organic Letters 12(20):4690-4693, Oct. 2010.
Tan, L., et al., "New Air-Stable Solution-Processed Organic n-Type Semiconductors Based on Sulfur-Rich Core-Expanded Naphthalene Diimides," Journal of Materials Chemistry 21(44):18042-18048, Nov. 2011.
Thompson, B.C., and J.M. Fréchet, "Polymer-Fullerene Composite Solar Cells," Angewandte Chemie 47(1):58-77, Dec. 2007.
Tonzola, C.J., et al., "New n-Type Organic Semiconductors: Synthesis, Single Crystal Structures, Cyclic Voltammetry, Photophysics, Electron Transport, and Electroluminescence of a Series of

(56) References Cited

OTHER PUBLICATIONS

Diphenylanthrazolines," Journal of the American Chemical Society 125(44):13548-13558, Nov. 2003.

Trost, B.M., "Antiaromatic Peripheral Systems. Synthesis and Chemistry of Pyracyloquinone," Journal of the American Chemical Society 91(4):918-923, Feb. 1969.

Trost, B.M., et al., "Perturbed [12]Annulenes. The Synthesis of Pyracylenes," Journal of the American Chemical Society 93(3):737-745, Feb. 1971.

Usta, H., et al., "n-Channel Semiconductor Materials Design for Organic Complementary Circuits," Accounts of Chemical Research 44(7):501-510, Jul. 2011.

Verheijen, M.A., et al., "The Structure of Different Phases of Pure C70 Crystals," Chemical Physics 166(1-2):287-297, Oct. 1992.

Wang, E., et al., "Small Band Gap Polymers Synthesized via a Modified Nitration of 4,7-Dibromo-2,1,3-benzothiadiazole," Organic Letters 12(20):4470-4473, Oct. 2010.

Wang, Z., et al., "Anthracenedicarboximides as Air-Stable N-Channel Semiconductors for Thin-Film Transistors With Remarkable Current On-Off Ratios," Journal of the American Chemical Society 129(44):13362-13363, Nov. 2007.

Wen, L., et al., "New Tunable Thieno[3,4-b]pyrazine-Based Materials," Synthetic Metals 159(21-22):2299-2301, Nov. 2009.

Woo, C.H., et al., "Phenyl vs Alkyl Polythiophene: A Solar Cell Comparison Using a Vinazene Derivative as Acceptor," Chemistry of Materials 22(5):1673-1679, Mar. 2010.

Xin, H., et al., "Enhanced Open Circuit Voltage and Efficiency of Donor-Acceptor Copolymer Solar Cells by Using Indene-C60 Bisadduct," Chemistry of Materials 24(11):1995-2001, Jun. 2012.

Yan, H., et al., "A High-Mobility Electron-Transporting Polymer for Printed Transistors," Nature 457(7230):679-686, Feb. 2007.

Yu, G., et al., "Polymer Photovoltaic Cells: Enhanced Efficiencies via a Network of Internal Donor-Acceptor Heterojunctions," Science 270(5243):1789-1791, Dec. 1995.

Lang, Y., et al., "Integrated Molecular, Interfacial, and Device Engineering Towards High-Performance Non-Fullerene Based Organic Solar Cells," Advanced Materials 26(32):5708-5714, Aug. 2014.

Zaumseil, J., and H. Sirringhaus, "Electron and Ambipolar Transport in Organic Field-Effect Transistors," Chemical Reviews 107(4):1296-1323, Apr. 2007.

Zhan, X., et al., "A High-Mobility Electron-Transport Polymer With Broad Absorption and Its Use in Field-Effect Transistors and All-Polymer Solar Cells," Journal of the American Chemical Society 129(23):7246-7247, Jun. 2007.

Zhan, X., et al., "Rylene and Related Diimides for Organic Electronics," Advanced Materials 23(2):268-284, Jan. 2011.

Zheng, Q., et al., "Pyromellitic Diimides: Minimal Cores for High Mobility n-Channel Transistor Semiconductors," Journal of the American Chemical Society 130(44):14410-14411, Nov. 2008.

Zhou, E., et aL, "All-Polymer Solar Cells From Perylene Diimide Based Copolymers: Material Design and Phase Separation Control," Angewandte Chemie 50(12):2799-2803, Mar. 2011.

Zhou, T., et al., "Nitrile-Substituted QA Derivatives: New Acceptor Materials for Solution-Processable Organic Bulk Heterojunction Solar Cells," Advanced Energy Materials 1(3):431-439, May 2011.

Zhou, Y., et al., "Non-Fullerene Acceptors Containing Fluoranthene-Fused Imides for Solution-Processed Inverted Organic Solar Cells," Chemical Communications 49(51):5802-5804, Jun. 2013.

Zhou, Y., et al., "A Non-Fullerene Small Molecule as Efficient Electron Acceptor in Organic Bulk Heterojunction Solar Cells," Advanced Materials 24(7):957-961, Feb. 2012.

Zhu, Y., et al., "Poly(pyrazinoquinoxaline)s: New n-Type Conjugated Polymers That Exhibit Highly Reversible Reduction and High Electron Affinity," Macromolecular Rapid Communications 25(21):1829-1834, Nov. 2004.

Ahmed, E., et al., "Benzobisthiazole-Based Donor-Acceptor Copolymer Semiconductors for Photovoltaic Cells and Highly Stable Field-Effect Transistors," Macromolecules 44(18):7207-7219, Sep. 2011.

Ahmed, E., et al., "Design of New Electron Acceptor Materials for Organic Photovoltaics: Synthesis, Electron Transport, Photophysics, and Photovoltaic Properties of Oligothiophene-Functionalized Naphthalene Diimides," Chemistry of Materials 23(20):4563-4577, Oct. 2011.

Anthony, J.E., "Small-Molecule, Nonfullerene Acceptors for Polymer Bulk Heterojunction Organic Photovoltaics," Chemistry of Materials 23(3):583-590, Feb. 2011.

Babel, A., and S.A. Jenekhe, "High Electron Mobility in Ladder Polymer Field-Effect Transistors," Journal of the American Chemical Society 125(45):13656-13657, Nov. 2003.

Beaupré, S., et al., "Multicolored Electrochromic Cells Based on Poly(2,7-carbazole) Derivatives for Adaptive Camouflage," Chemistry of Materials 21(8):1504-1513, Apr. 2009.

Bloking, J.T., et al., "Solution-Processed Organic Solar Cells With Power Conversion Efficiencies of 2.5% Using Benzothiadiazole/Imide-Based Acceptors," Chemistry of Materials 23(24):5484-5490, Dec. 2011.

Blom, P.W.M., et al., "Device Physics of Polymer:Fullerene Bulk Heterojunction Solar Cells," Advanced Materials 19(12):1551-1566, Jun. 2007.

Brabec, C.J., et al., "Effect of LiF/Metal Electrodes on the Performance of Plastic Solar Cells," Applied Physics Letters 80(7):1288-1290, Feb. 2002.

Briseno, A.L., et al., "Perylenediimide Nanowires and Their Use in Fabricating Field-Effect Transistors and Complementary Inverters," Nano Letters 7(9)2847-2853, Sep. 2007.

Briseno, A.L., et al., "Self-Assembly, Molecular Packing, and Electron Transport in n-Type Polymer Semiconductor Nanobelts," Chemistry of Materials 20(14):4712-4719, Jul. 2008.

CHen, C.-H., et al., "Synthesis and Characterization of Bridged Bithiophene-Based Conjugated Polymers for Photovoltaic Applications: Acceptor Strength and Ternary Blends," Macromolecules 43(2):697-708, Jan. 2010.

Chen, H.-Y., et al., "Polymer Solar Cells With Enhanced Open-Circuit Voltage and Efficiency," Nature Photonics 3(11):649-653, Nov. 2009.

Chen, Z., et al., "Naphthalenedicarboximide- vs Perylenedicarboximide-Based Copolymers. Synthesis and Semiconducting Properties in Bottom-Gate N-Channel Organic Transistors," Journal of the American Chemical Society 131(1):8-9, Jan. 2009.

Chochos, C.L., et al., "Rational Design of n-Type Organic Materials for High Performance Organic Photovoltaics," RSC Advances 3(20):7160-7181, May 2013.

Clarke, T.M., and J.R., Durrant, "Charge Photogeneration in Organic Solar Cells," Chemical Reviews 110(11):6736-6767, Nov. 2010.

Earmme, T., et al., "All-Polymer Bulk Heterojunction Solar Cells With 4.8% Efficiency Achieved by Solution Processing From a Co-Solvent," Advanced Materials 26(35):6080-6085, Sep. 2014.

Earmme, T., et al., "All-Polymer Solar Cells With 3.3% Efficiency Based on Naphthalene Diimide-Selenophene Copolymer Acceptor," Journal of the American Chemical Society 135(40):14960-14963, Oct. 2013.

Gao, X., et al., "Core-Expanded Naphthalene Diimides Fused With 2-(1,3-Dithiol-2-ylidene)malonitrile Groups for High-Performance, Ambient-Stable, Solution-Processed n-Channel Organic Thin Film Transistors," Journal of the American Chemical Society 132(11):3697-3699, Mar. 2010.

Geng, Y., et al., "Monodisperse Oligofluorenes Forming Glassy-Nematic Films for Polarized Blue Emission," Chemistry of Materials 15(2):542-549, Jan. 2003.

Goel, A., et al., "Size Analysis of Single Fullerene Molecules by Electron Microscopy," Carbon 42(10):1907-1915, 2004.

González, S.R., et al., "A β-Naphthaleneimide-Modified Terthiophene Exhibiting Charge Transfer and Polarization Through

(56) References Cited

OTHER PUBLICATIONS the Short Molecular Axis. Joint Spectroscopic and Theoretical Study," Journal of Physical Chemistry A 112(29):6732-6740, Jul. 2008.

Gregg, B.A., "Entropy of Charge Separation in Organic Photovoltaic Cells: The Benefit of Higher Dimensionality," Journal of Physical Chemistry Letters 2(24):3013-3015, Dec. 2011.

Gui, K., et al., "A Flexible n-Type Organic Semiconductor for Optoelectronics," Journal of Materials Chemistry 22(5):1800-1806, Feb. 2012.

Günes, S., et al., "Conjugated Polymer-Based Organic Solar Cells," Chemical Reviews 107(4):1324-1338, Apr. 2007.

Guo, X., and M.D. Watson, "Conjugated Polymers From Naphthalene Bisimide," Organic Letters 10(23):5333-5336, Dec. 2008.

HE, Z., et al., "Enhanced Power-Conversion Efficiency in Polymer Solar Cells Using an Inverted Device Structure," Nature Photonics 6(9):591-595, Sep. 2012.

Hong, D.-J., et al., "Self-Organized Spiral Columns in Laterally Grafted Rods," Chemical Communications 46(27):4896-4898, Jul. 2010.

Huang, X., et al., "Novel Dyes Based on Naphthalimide Moiety as Electron Acceptor for Efficient Dye-Sensitized Solar Cells," Dyes and Pigments 90(3):297-303, Sep. 2011.

Hundt, N., et al., "Polymers Containing Rigid Benzodithiophene Repeating Unit With Extended Electron Delocalization," Organic Letters 11(19):4422-4425, Oct. 2009.

Hüttner, S., et al., "n-Type Organic Field Effect Transistors From Perylene Bisimide Block Copolymers and Homopolymers," Applied Physics Letters 92(9):093302, 2008, 3 pages.

Jamieson, F.C., et al., "Fullerene Crystallisation as a Key Driver of Charge Separation in Polymer/Fullerene Bulk Heterojunction Solar Cells," Chemical Science 3(2):485-492, Feb. 2012.

Johansson Seechurn, C.C.C., et al., "Palladium-Catalyzed Cross-Coupling: A Historical Contextual Perspective to the 2010 Nobel Prize," Angewandte Chemie 51(21):5062-5085, May 2012.

Kanibolotsky, A.L., et al., "Star-Shaped π-Conjugated Oligomers and Their Applications in Organic Electronics and Photonics," Chemical Society Reviews 39(7):2695-2728, Jul. 2010.

Kim, F.S., et al., "One-Dimensional Nanostructures of π-Conjugated Molecular Systems: Assembly, Properties, and Applications From Photovoltaics, Sensors, and Nanophotonics to Nanoelectronics," Chemistry of Materials 23(3):682-732, Feb. 2011.

Kim, J.Y., et al., "Efficient Tandem Polymer Solar Cells Fabricated by All-Solution Processing," Science 317(5835):222-225, Jul. 2007.

Kwon, T.W., et al., "n-Type Conjugated Dendrimers: Convergent Synthesis, Photophysics, Electroluminescence, and Use as Electron-Transport Materials for Light-Emitting Diodes," Chemistry of Materials 16(23):4657-4666, Nov. 2004.

Letizia, J.A., et al., "n-Channel Polymers by Design: Optimizing the Interplay of Solubilizing Substituents, Crystal Packing, and Field-Effect Transistor Characteristics in Polymeric Bithiophene-Imide Semiconductors," Journal of the American Chemical Society 130(30):9679-9694, Jul. 2008.

Li, G., et al., "High-Efficiency Solution Processable Polymer Photovoltaic Cells by Self-Organization of Polymer Blends," Nature Materials 4(11):864-868, Nov. 2005.

Li, G., et al., "Polymer Solar Cells," Nature Photonics 6(3):153-161, Mar. 2012.

Liang, Y., et al., "For the Bright Future—Bulk Heterojunction Polymer Solar Cells With Power Conversion Efficiency of 7.4%," Advanced Materials 22(20):E135-E138, May 2010.

Liu, S., et al., "Synthesis and Optical Properties of a Series of Thermally Stable Diphenylanthrazolines," Dyes and Pigments 81(3):218-223, Jun. 2009.

Liu, T., and A. Troisi, "What Makes Fullerene Acceptors Special as Electron Acceptors in Organic Solar Cells and How to Replace Them," Advanced Materials 25(7):1038-1041, Feb. 2013.

Lo, S.-C., and P.L. Burn, "Development of Dendrimers: Macromolecules for Use in Organic Light-Emitting Diodes and Solar Cells," Chemical Reviews 107(4):1097-1116, Apr. 2007.

Ma, W., et al., "Thermally Stable, Efficient Polymer Solar Cells With Nanoscale Control of the Interpenetrating Network Morphology," Advanced Functional Materials 15(10):1617-1622, Oct. 2002.

Miyaura, N., and A. Suzuki, "Palladium-Catalyzed Cross-Coupling Reactions of Organoboron Compounds," Chemical Reviews 95(7):2457-2483, Nov. 1995.

Mori, D., et al., "Polymer/Polymer Blend Solar Cells Improved by Using High-Molecular-Weight Fluorene-Based Copolymer as Electron Acceptor," ACS Applied Materials & Interfaces 4(7):3325-3329, Jul. 2012.

Nielsen, C.B., et al., "Efficient Truxenone-Based Acceptors for Organic Photovoltaics," Journal of Materials Chemistry A 1(1):73-76, Jan. 2013.

Nietfeld, J.P., et al., "Structural Effects on the Electronic Properties of Extended Fused-Ring Thieno[3,4-b]pyrazine Analogues," Journal of Organic Chemistry 76(15):6383-6388, Aug. 2011.

Palmaerts, A., et al., "Development of Novel Processable Electron Accepting Conjugated Polymers Containing Fluoranthene Units in the Main Chain," Polymer 50(21):5007-5015, Oct. 2009.

Park, S.H., et al., "Bulk Heterojunction Solar Cells With Internal Quantum Efficiency Approaching 100%," Nature Photonics 3(3)297-302, May 2009.

\* cited by examiner

ACENAPHTHYLENE IMIDE-DERIVED SEMICONDUCTORS

BACKGROUND

N-type organic semiconductors are needed for fabricating n-channel organic field effect transistors, p-n junction diodes, and complementary organic logic circuits. However, high performance electron transport materials are still relatively rare. Therefore, development of new n-type organic semiconductors with high charge carrier mobility, improved processability, high thermal and oxidative stability remains a major challenge in the field of organic electronics.

Among the existing n-type organic semiconductors, naphthalene diimides (NDIs) and perylene diimides (PDIs) and their derivatives are of particular interest as electron-transport materials because of their high electron affinity, chemical stability, as well as their relatively large planar structures (Anthony et al., *Adv. Mater.* 2010, 22, (34), 3876; Zhan et al., *Adv. Mater.* 23, (2), 268). Recent research has also developed other new diimide compounds, such as benzene and anthracene diimides (Zheng et al., *J. Am. Chem. Soc.* 2008, 130, 14410; Wang et al., *J. Am. Chem. Soc.* 2007, 129, 13362). Other attempts have also aimed to increase the molecular size in order to extend the π-conjugation and promote better solid state packing by expansion of the NDI and PDI cores (Gao et al., *J. Am. Chem. Soc.* 2010, 132, 3697; Tan et al., *J. Mater. Chem.,* 2011, 21, (44), 18042). Beside the interesting properties obtained from thin films of arylene diimides, self-assembly of nanowires of naphthalene diimides and perylene diimides and their applications in organic nanoelectronics have also been extensively investigated, showing that a dramatic increase in electron mobility can result from crystalline nanostructures (Kim et al., *Chem. Mater.* 2011, 23, 682; Briseno et al., *Nano Lett.* 2007, 7, 2847). Another family of n-type organic semiconductors which has drawn attention is the imine nitrogen-containing heteroaromatics, including pyridine, quinoline, pyrazine, thiazole, benzothiadiazole, benzobisthiazole, etc. Members of this later class are also known for their low lying LUMO energy levels, high electron affinities and high field-effect mobilities (Tonzola et al., *J. Am. Chem. Soc.* 2003, 125, 13548).

Further, polymer-based semiconductors have also been studied in Babel et al., *J. Am. Chem. Soc.,* 2003, 125, 13656; Briseno et al., *Chem. Mater.* 2008, 20, 4712; Chen et al., *J. Am. Chem. Soc.* 2009, 131, 8; Yan et al., *Nature* 2009, 457, (7230), 679; Huttner et al., *Appl. Phys. Lett.* 2008, 92, 093302; Letizia et al., *J. Am. Chem. Soc.* 2008, 130, (30), 9679; Zhan et al., *J. Am. Chem. Soc.* 2007, 129, 7246; and Ahmed et al., *Chem. Mater.* 2011, 23, (20), 4563.

Thus, a need exists for novel organic semiconductors, including n-type small molecule-based and polymer-based semiconductors suitable for uses as active components in organic electronic and optoelectronic devices. In particular, materials which provide good transistor performance such as high charge mobility, high on/off current ratios, and low threshold voltages are needed. Good solubility and thermal stability is also needed.

SUMMARY

Embodiments described herein include compounds, compositions, devices, methods of making, and methods of using.

For example, provided is a compound represented by:

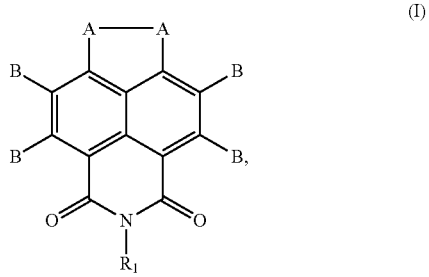

wherein: (i) one or both of A are —C(O)—, and the remaining A, if any, is —CH$_2$—; (ii) R$_1$ is an optionally substituted C$_1$-C$_{50}$ organic group; and (iii) B at each occurrence is independently selected from hydrogen, halogen, cyano, nitro, optionally substituted alkyl group and optionally substituted heteroalkyl group, or a structure wherein each pair of substituents B in ortho position optionally forms a conjugated ring.

In one embodiment, the compound is represented by:

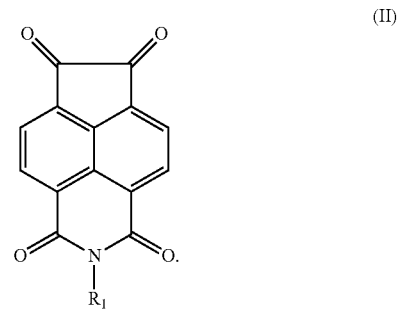

In another embodiment, the compound is represented by:

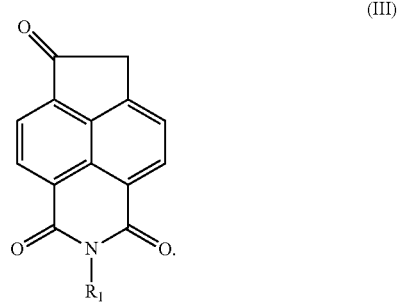

Also provided is a method for making the compound described above, comprising
(i) reacting an oxidant with a compound represented by formula (IV):

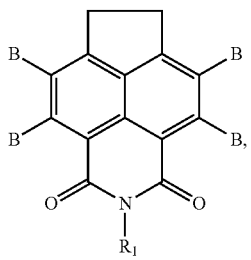

(IV)

wherein $R_1$ and B have the same definitions as previously described; and (ii) separating a first product represented by

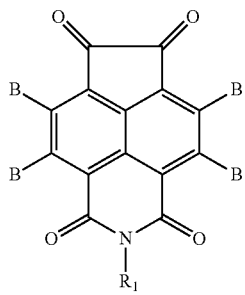

(V)

from a second product represented by

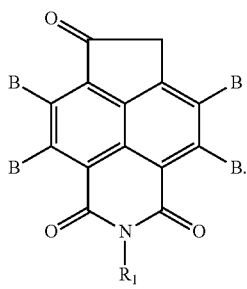

(VI)

In one embodiment, the oxidant is selected from $CrO_3$ and $SeO_2$.

Also provided is a method for using the compound described above, comprising reacting said compound with a second compound comprising one or more primary amine groups.

In one embodiment, the second compound is represented by

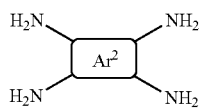

(XX)

or its acid complex

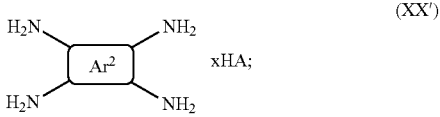

(XX')

wherein $Ar^2$ comprises an optionally substituted aryl ring or an optionally substituted heteroaryl ring, or two or more of said rings fused together; and wherein HA is HCl, HBr, HI, $CH_3COOH$, $H_2SO_4$ or $H_3PO_4$, x is 1, 2, 3 or 4.

In another embodiment, the second compound is represented by

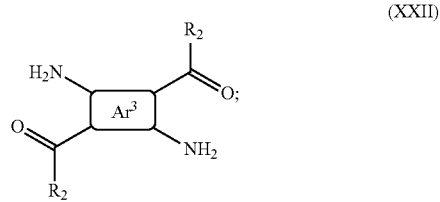

(XXII)

wherein $Ar^3$ comprises an optionally substituted aryl ring or an optionally substituted heteroaryl ring, or two or more of said rings fused together; and wherein $R_2$ at each occurrence is an end group optionally linked by a single bond or by one or more conjugation side groups.

In a further embodiment, the second compound is represented by

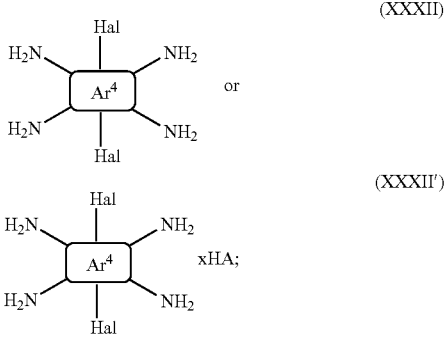

(XXXII)

or (XXXII')

wherein $Ar^4$ comprises an optionally substituted aryl ring or an optionally substituted heteroaryl ring, or two or more of said rings fused together; wherein Hal at each occurrence comprises a halogen optionally linked by one or more conjugation side groups; and wherein HA and x have the same definitions as previously described.

In yet another embodiment, the second compound is represented by

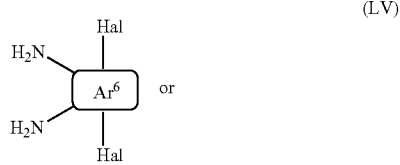

(LV)

-continued

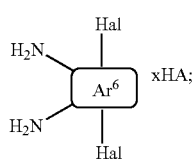
(LV')

wherein Ar⁶ comprises an optionally substituted aryl ring or an optionally substituted heteroaryl ring, or two or more of said rings fused together; and wherein Hal, HA and x have the same definitions as previously described.

In yet a further embodiment, the second compound is represented by represented by

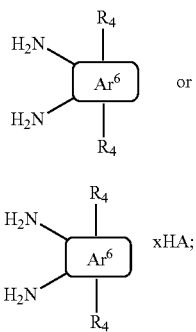
(LVII)

(LVII')

wherein $R_4$ at each occurrence comprises an end group linked by one or more conjugation side groups; and wherein Ar⁶, HA and x have the same definitions as previously described.

Further provided is a compound represented by:

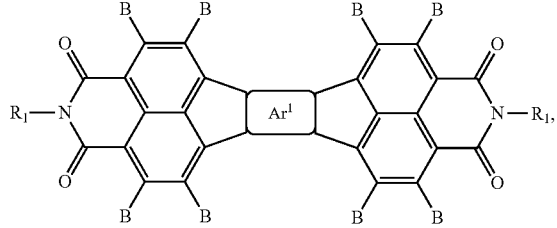
(VII)

wherein: (i) Ar¹ comprises three or more rings fused together, each ring is an optionally substituted aryl ring or an optionally substituted heteroaryl ring; (ii) $R_1$ and B have the same definitions as previously described.

Further provided is a polymer comprising one or more first repeating units RU1 represented by

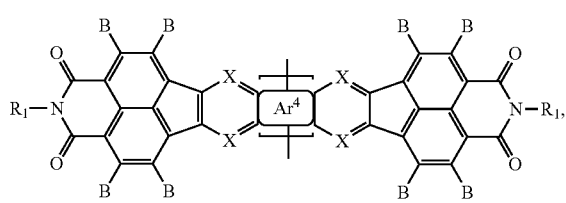
(XXIV)

wherein: (i) X at each occurrence is independently selected from

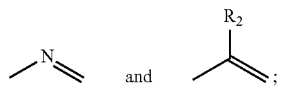

and (ii) Ar⁴, $R_1$, $R_2$ and B have the same definitions as previously described.

Additionally provided is a compound represented by

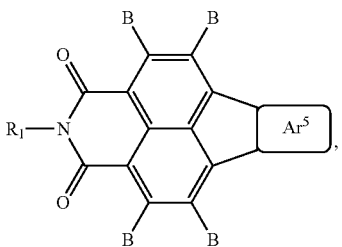
(XXXIV)

wherein: (i) Ar⁵ comprises two or more rings fused together, each ring is an optionally substituted aryl ring or an optionally substituted heteroaryl ring; (ii) $R_1$ and B have the same definitions as previously described.

Additionally provided is a polymer comprising one or more first repeating units RU3 represented by

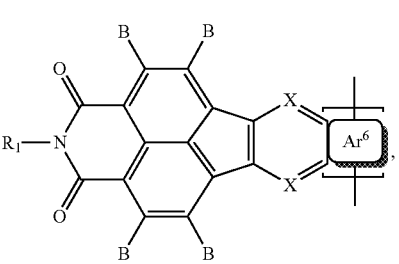
(LIX)

wherein: Ar⁶, $R_1$, X and B have the same definitions as previously described.

Also provided are compositions as well as electronic or optoelectronic devices comprising at least one compound or polymer described herein or made by any of the methods described herein. In one embodiment, the device is a transistor such as an organic-field effect transistor. In another embodiment, the device is a complementary electronic circuit such as an inverter.

At least one advantage for at least some embodiments of the semiconducting materials described herein is high charge carrier mobility.

At least another advantage for at least some embodiments of the semiconducting materials described herein is good solution processability.

At least another advantage for at least some embodiments of the semiconducting materials described herein is good thermal stability.

At least one further advantage for at least some embodiments of the semiconducting materials described herein is increased electron affinity.

At least one further advantage for at least some embodiments of the semiconducting materials described herein is extended π-conjugation and improved intermolecular electronic coupling.

At least one further advantage for at least one of the embodiments of the semiconducting materials described herein is ready self-assembling into single crystalline nano- or microstructures.

At least one further advantage for at least one of the embodiments of the semiconducting materials described herein is good switching characteristics when used as the n-channel component in complementary electronic circuits such as an inverter.

At least one further advantage for at least one of the embodiments of the semiconducting materials described herein is comparable on-current and off-current when used as n-channel component in complementary electronic circuits such as an inverter.

At least one further advantage for at least one of the embodiments of the semiconducting materials described herein is high gain when used as n-channel component in complementary electronic circuits such as an inverter.

Another further advantage for at least some embodiments is synthetic versatility and ability to tune the electronic properties based on structural variations.

DETAILED DESCRIPTION

Introduction

Figure 1:
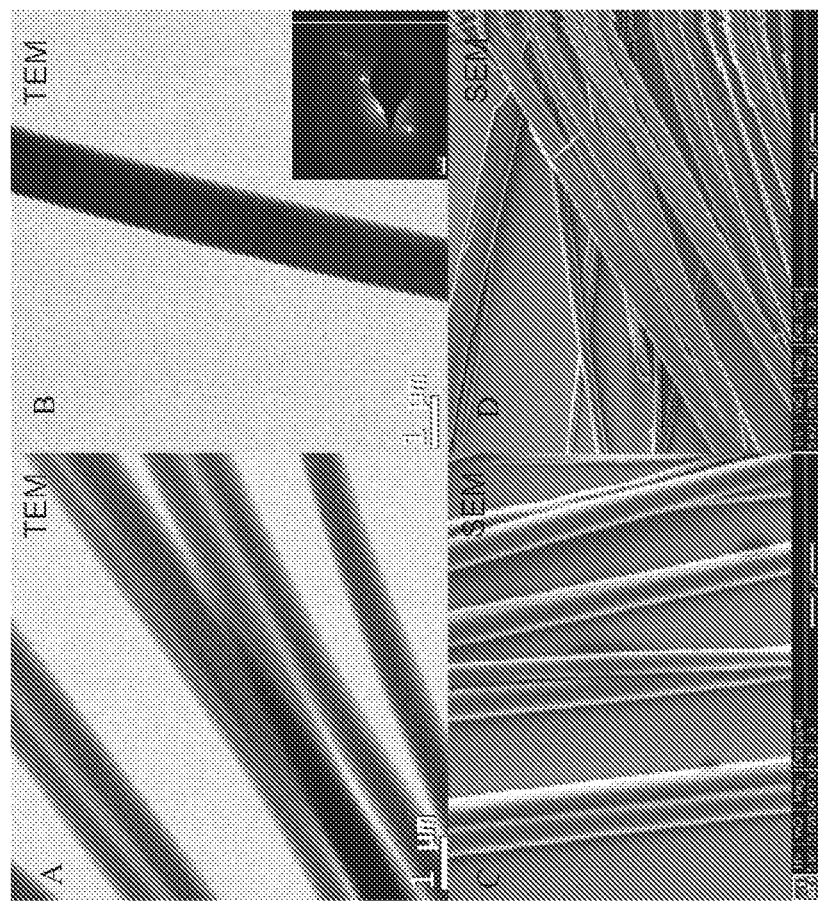
FIG. 1 shows SEM and TEM images with corresponding electron diffraction (inset) of an exemplary compound described herein (BFI)

All references described herein are hereby incorporated by reference in their entireties. Various terms are further described herein below:

"A", "an", and "the" can refer to "at least one" or "one or more" unless specified otherwise.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

"Alkyl" can refer to, for example, linear, branched, or cyclic alkyl groups. This term is exemplified by groups such as methyl, ethyl, n-propyl, isopropyl, n-butyl, t-butyl, n-pentyl, ethylhexyl, dodecyl, isopentyl, cyclohexyl, and the like.

"Aryl" can refer to, for example, aromatic carbocyclic groups having one or more single rings (e.g., phenyl or biphenyl) or multiple condensed rings (e.g., naphthyl or anthryl).

"Heteroalkyl" can refer to, for example, an alkyl group wherein one or more carbon atoms are substituted with heteroatoms.

"Heteroaryl" can refer to, for example, an aryl group wherein one or more carbon atoms are substituted with heteroatoms.

"Fluoroalkyl" can refer to, for example, an alkyl group wherein one or more hydrogen atoms are substituted with fluoro. Fluoroalkyl described herein include perfluoroalkyl as well as partially fluorinated alkyl.

"Fluoroalkoxide" can refer to, for example, an alkoxide group wherein one or more hydrogen atoms are substituted with fluoro. Fluoroalkoxide described herein include perfluoroalkoxide group as well as partially fluorinated alkoxide.

"n" and "m" can refer to a positive integer.

Part I—Monoketo and Diketo Intermediate

Structure of Monoketo and Diketo Intermediate

A variety of 1,2-dihydroacenaphthylene-based compounds are known in the art and described in, for example, (i) Huang et al., *Dyes Pigm.* 2011, 90, (3), 297-303; (ii) Sun et al., *Org. Lett.* 2010, 12, (20), 4690-4693; (iii) Nietfeld et al., *The Journal of Organic Chemistry* 2011, 76, (15), 6383-6388; (iv) Palmaerts et al., *Polymer* 2009, 50, (21), 5007-5015; (v) Wen et al., *Synth. Met.* 2009, 159, (21-22), 2299-2301; (vi) González et al., *The Journal of Physical Chemistry A* 2008, 112, (29), 6732-6740; (vii) Ortiz et al., *J. Am. Chem. Soc.* 2010, 132, (24), 8440-8452; (viii) Trost et al., *J. Am. Chem. Soc.* 1971, 93, 737-745; (ix) Trost et al., *J. Am. Chem. Soc.* 1969, 91, (4), 918-923; and (x) WO/2009/126203, all of which are hereby incorporated by reference by their entireties.

Many embodiments described herein relate to a compound represented by formula (I):

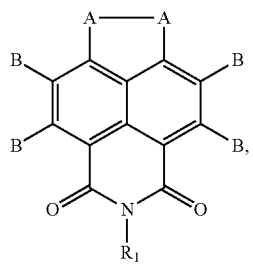

(I)

wherein: (i) one or both of A are —C(O)—, and the remaining A, if any, is —CH$_2$—; (ii) $R_1$ is an optionally substituted $C_1$-$C_{50}$ organic group; and (iii) B at each occurrence is independently selected from hydrogen, halogen, cyano, nitro, optionally substituted alkyl group and optionally substituted heteroalkyl group, or a structure wherein each pair of substituents B in ortho position optionally forms a conjugated ring.

$R_1$ can be, for example, an optionally substituted linear, branched or cyclic $C_1$-$C_{36}$ alkyl group or an optionally substituted linear, branched or cyclic $C_1$-$C_{36}$ heteroalkyl group. $R_1$ can be, for example, an optionally substituted linear or branched $C_{12}$-$C_{36}$ alkyl group or an optionally substituted linear or branched $C_{12}$-$C_{36}$ heteroalkyl group. $R_1$ can be, for example, unsubstituted or substituted with one or more halogens. $R_1$ can be, for example, a linear or branched fluoroalkyl group or a linear or branched fluoroalkoxide group. In addition, $R_1$ can be any other solubilizing group known in the art.

B can be, for example, hydrogen, halogen, cyano, nitro, an optionally substituted alkyl group, or an optionally substituted heteroalkyl group. B at each occurrence can be, for example, hydrogen, fluoro, a linear or branched $C_1$-$C_{24}$, $C_1$-$C_{12}$ or $C_1$-$C_6$ alkyl group, or a linear or branched $C_1$-$C_{24}$, $C_1$-$C_{12}$ or $C_1$-$C_6$ heteroalkyl group. In addition, for example, B at each occurrence can be hydrogen or independently selected from an optionally substituted $C_1$-$C_{30}$ organic group. In one embodiment, each B is the same. This can provide for a symmetrical compound.

In one embodiment, B at each occurrence is hydrogen. In another embodiment, each pair of substituents B in ortho position forms a conjugated ring such as, for example, a benzene ring. In a further embodiment, at least one B comprises a reactive group. In yet another embodiment, at least two B comprise reactive groups, and the compound is a monomer suitable for polymerization. In yet a further embodiment, at least one B comprises a side conjugation group described herein.

In some embodiments, both A are —C(O)—, and the compound is a diketo intermediate represented by formula (V):

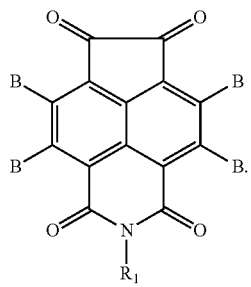

(V)

In a particular embodiment wherein B is hydrogen, the diketo intermediate can be represented by formula (II):

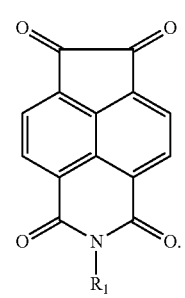

(II)

In some embodiments, only one A is —C(O)— with the other being hydrogen, and the compound is a monoketo intermediate represented by formula (VI):

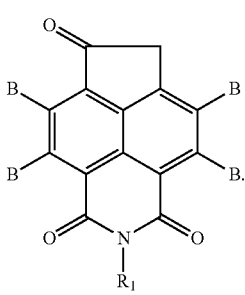

(VI)

In a particular embodiment wherein B is hydrogen, the monoketo intermediate is represented by formula (III):

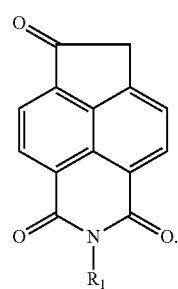

(III)

Methods for making Monoketo and Diketo Intermediate

The monoketo intermediate and the diketo intermediate described herein can be made by, for example, reacting an oxidant with a compound represented by formula (IV):

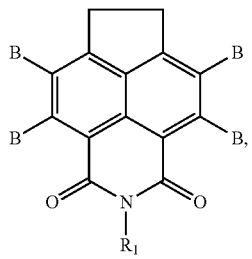

(IV)

and separating a first product represented by

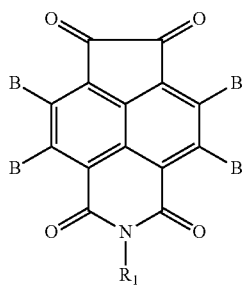

(V)

from a second product represented by

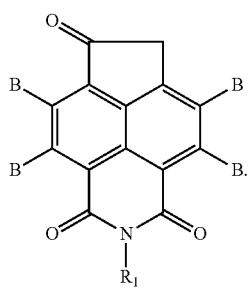

(VI)

Oxidation agents and oxidants are generally known in the art. The oxidant can be, for example, selected from $CrO_3$, $H_2CrO_4$, $Na_2CrO_4$, $O_3$, $RCO_3H$, tBuOOH/NaOCl, DMSO/PyHBr_3, DMSO/2-pyrrolidinone HBr_3, $SeO_2$ and $MnO_2$. In one embodiment, the oxidant is $CrO_3$. In another embodiment, the oxidant is $SeO_2$.

The first product and the second product can be obtained under different reaction conditions, for example under different reaction temperatures. See, for example, working examples below.

The first product and the second product can be separated by, for example, chromatographic methods. Various chromatographic methods are known in the art and described in, for example, James M. Miller, *Chromatography: Concepts and Contrasts*, 2$^{nd}$ Ed., John Wiley, 2009, which is hereby incorporated by reference in its entirety. In a particular embodiment, the first product and the second product are separated by thin film chromatography.

Use of Monoketo and Diketo Intermediate

Reactions at the ketone can be carried out as known in organic synthetic chemistry. For example, the ketone can be reacted with nucleophilic groups. The monoketo intermediate and the diketo intermediate described herein can be used to, for example, synthesize downstream compounds, monomers, oligomers, and polymers. The intermediate compound can be reacted with, for example, a second compound comprising one or more amine groups, including primary and secondary amines, preferably primary amine groups.

The second compound can comprise, for example, at least one primary amine group, at least two primary amine groups, or at least four primary amine groups. The second compound can comprise, for example, at least one aromatic or heteroaromatic ring. The aromatic or heteroaromatic ring can be, for example, a five-membered ring or a six-membered ring. The second compound can comprise, for example, one pair of ortho-positioned primary amine groups on an aromatic or heteroaromatic ring, or two pairs of ortho-positioned primary amine groups on the same or two different aromatic or heteroaromatic rings. The second compound can comprise, for example, one pair of ortho-positioned groups, comprising a primary amine group and a ketone or an aldehyde group, on an aromatic or heteroaromatic ring. The second compound can comprise, for example, two pairs of ortho-positioned groups, each pair comprising a primary amine group and a ketone or an aldehyde group, on the same or two different aromatic or heteroaromatic rings.

Additional reactions for the ketone compounds are described hereinbelow.

Part II—Type-A Compound

Structure of Type-A Compound

Many embodiments described herein relate to Type-A compounds represented by formula (VII):

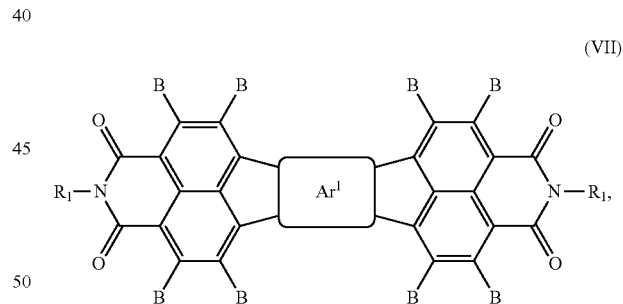

(VII)

wherein: (i) $Ar^1$ comprises three or more rings fused together, each ring is an optionally substituted aryl ring or an optionally substituted heteroaryl ring; (ii) $R_1$ and B have the same definitions as previously described.

$Ar^1$ can be, for example, a heteroaryl group comprising in the heteroaromatic ring(s) one or more N heteroatoms, or two or more N heteroatoms, or three or more N heteroatoms, or four or more N heteroatoms, or five or more N heteroatoms, or six or more N heteroatoms. $Ar^1$ can be, for example, a heteroaryl group comprising one or more imine moieties, or two or more imine moieties, or three or more imine moieties, or four or more imine moieties, or five or more imine moieties, or six or more imine moieties.

In some embodiments, B is hydrogen and $Ar^1$ is represented by, for example,

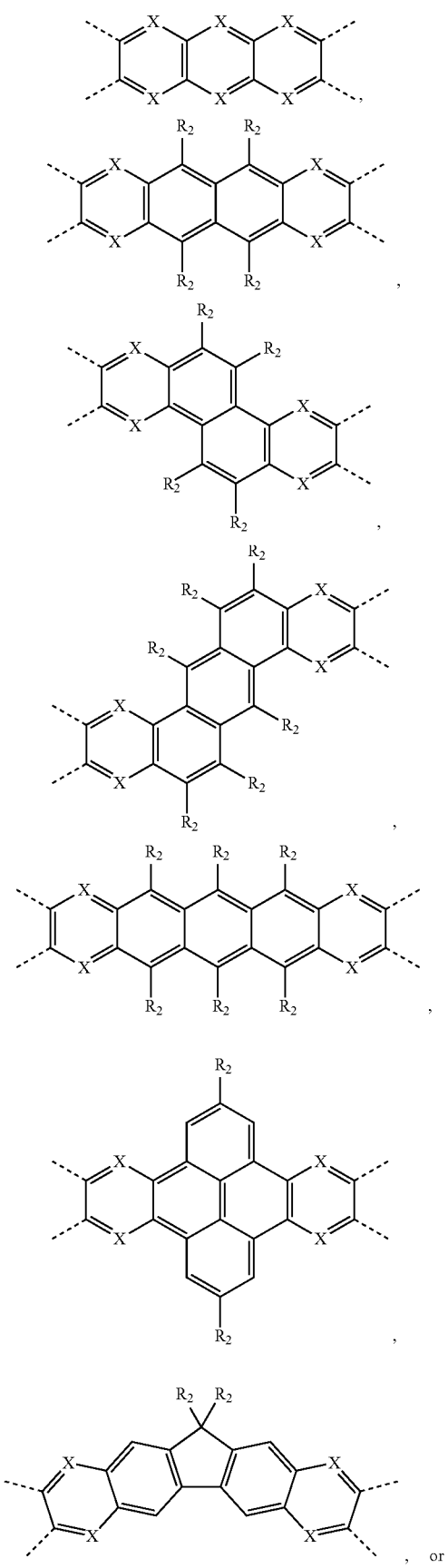

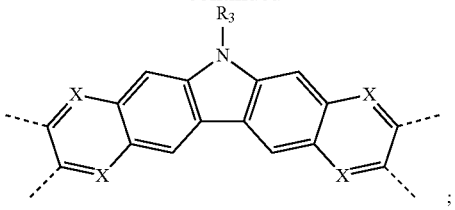

wherein X at each occurrence is independently selected from

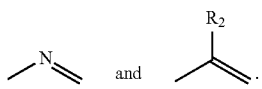

R$_2$ at each occurrence can comprise, for example, an end group or a substituent and optionally one or more conjugation side groups linking the end group (or substituent) and the aromatic group that R$_2$ is attached to. When R$_2$ comprises at least one conjugation side group, the end group (or substituent) can be linked to the aromatic group via said conjugation side group. When R$_2$ comprises no conjugation side group, the end group (or substituent) can be linked directly to the aromatic group by a single bond.

The end group or substituent described herein can be, for example, selected from hydrogen, halogen, cyano, nitro, an optionally substituted alkyl group and an optionally substituted heteroalkyl group. The end group or substituent can be, for example, hydrogen, cyano, an optionally substituted linear or branched $C_1$-$C_{24}$, $C_1$-$C_{12}$ or $C_1$-$C_6$ alkyl group, or an optionally substituted linear or branched $C_1$-$C_{24}$, $C_1$-$C_{12}$ or $C_1$-$C_6$ heteroalkyl group. The end group or substituent can be, for example, unsubstituted or substituted with one or more halogens. The end group or substituent can be, for example, a linear or branched fluoroalkyl group or a linear or branched fluoroalkoxide group. In some particular embodiments, R$_2$ comprises at least one conjugation side group, and the end group or substituent is selected from hydrogen, cyano, a linear or branched alkyl such as —CH$_3$, and a linear or branched fluoroalkyl such as —CF$_3$.

The optional conjugation side group described herein can be, for example, independently selected from an optionally substituted aryl group, an optionally substituted heteroaryl group, an optionally substituted ethenylene, and ethynylene. The conjugation side group, can be, for example, an optionally substituted $C_5$-$C_{24}$ or $C_5$-$C_{12}$ aryl group, or an optionally substituted $C_5$-$C_{24}$ or $C_5$-$C_{12}$ heteroaryl group. In some embodiments, each conjugation side group is independently selected from

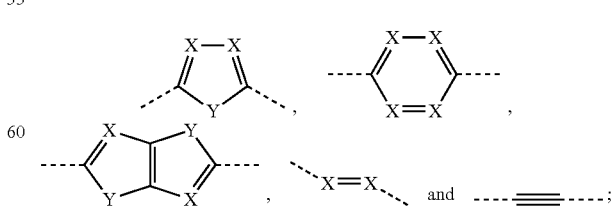

wherein Y is O, S, Se, Te, N(R$_3$), C(R$_3$)$_2$, Si(R$_3$)$_2$. Particular embodiments of the conjugation side group include the following:

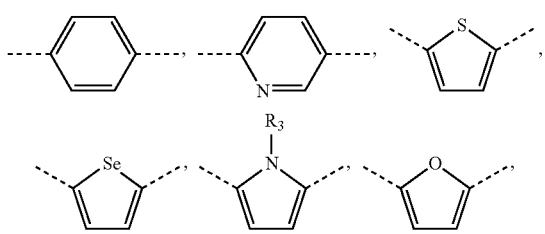

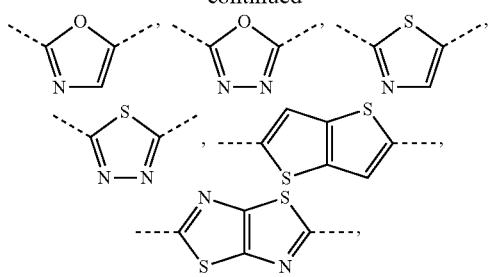

all of which can be further substituted with, for example, an optionally substituted linear or branched $C_1$-$C_{24}$, $C_1$-$C_{12}$ or $C_1$-$C_6$ alkyl group including fluoroalkyl, or an optionally substituted linear or branched $C_1$-$C_{24}$, $C_1$-$C_{12}$ or $C_1$-$C_6$ heteroalkyl group including fluoroalkoxide.

$R_3$ can be, for example, hydrogen, cyano, an optionally substituted linear or branched $C_1$-$C_{24}$, $C_1$-$C_{12}$ or $C_1$-$C_6$ alkyl group, or an optionally substituted linear or branched $C_1$-$C_{24}$, $C_1$-$C_{12}$ or $C_1$-$C_6$ heteroalkyl group. $R_3$ can be, for example, unsubstituted or substituted with one or more halogens. $R_3$ can be, for example, a linear or branched fluoroalkyl group or a linear or branched fluoroalkoxide group. Particular embodiments of $R_3$ include hydrogen, cyano, a linear or branched alkyl such as —$CH_3$, and a linear or branched fluoroalkyl such as —$CF_3$.

Many embodiments of the Type-A compound described herein relate to a monomer (Type-A monomer) suitable for polymerization or copolymerization, wherein $Ar^1$ comprises one or more, or two or more polymerizable groups. Polymerizable groups are known in the art and include, for example, halogen atoms such as Br.

In some embodiments, the Type-A monomer is selected from formulae (VIII), (IX) and (X):

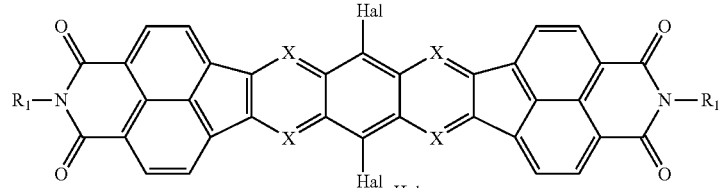
(VIII)

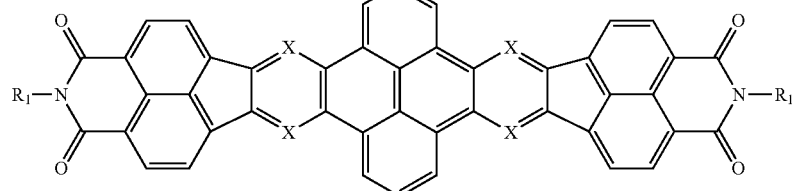
(IX)

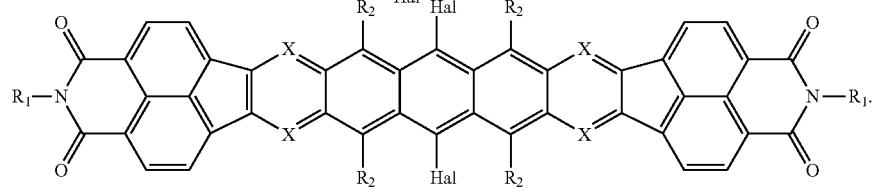
(X)

X, $R_1$, $R_2$ and the conjugation side group have the same definitions as previously described. Hal at each occurrence can comprise, for example, an halogen and optionally one or more conjugation side groups linking the halogen and the aromatic group that Hal is attached to. The halogen can be, for example, Br. The halogens can be para to each other. When Hal comprises at least one conjugation side group, the halogen can be linked to the aromatic group via said conjugation side group. When Hal comprises no conjugation side group, the halogen can be linked directly to the aromatic group by a single bond.

In a particular embodiment, the Type-A monomer is represented by formula (XI):

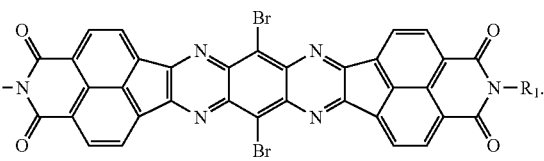
(XI)

Many embodiments of the Type-A compound described herein relate to a compound selected from formulae (XII), (XIII) and (XIV):

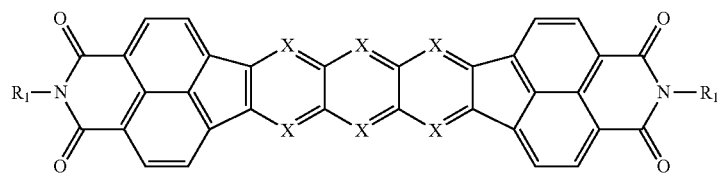
(XII)
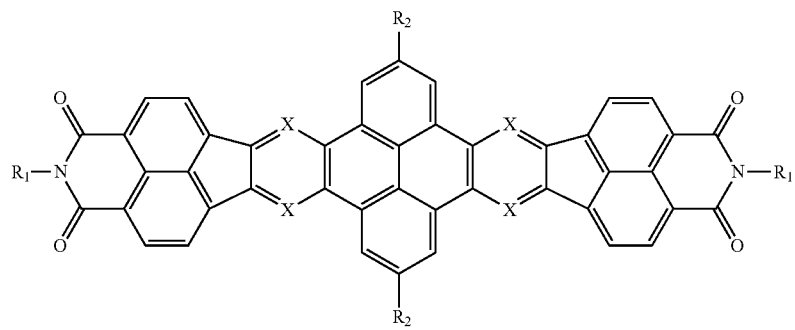
(XIII)
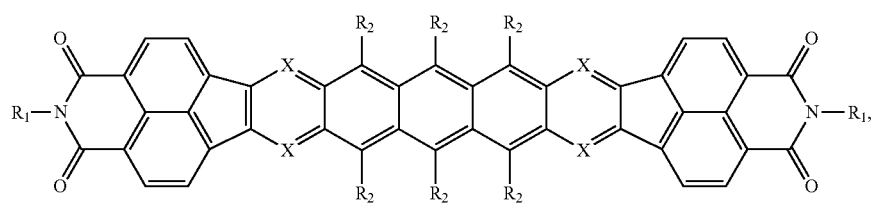
(XIV)
wherein X, R₁ and R₂ have the same definitions as previously described.
In some embodiments, the Type-A compound is selected from:
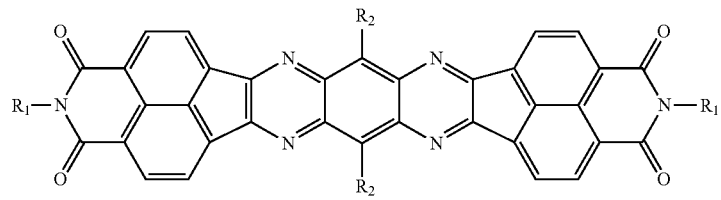
(XV)
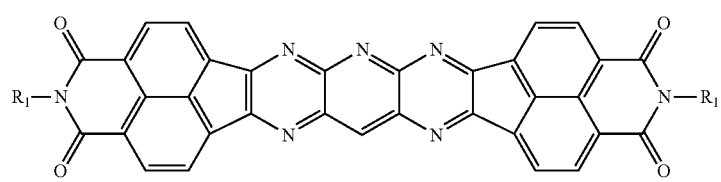
(XVI)
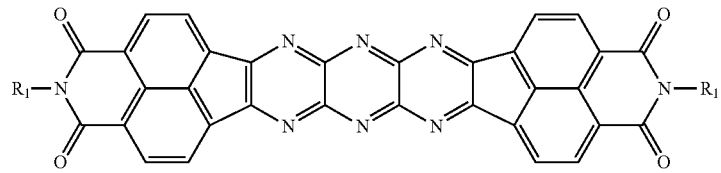
(XVII)
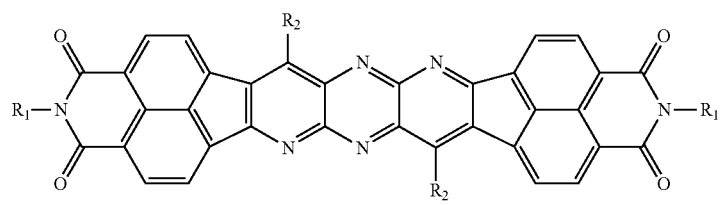
(XVIII)

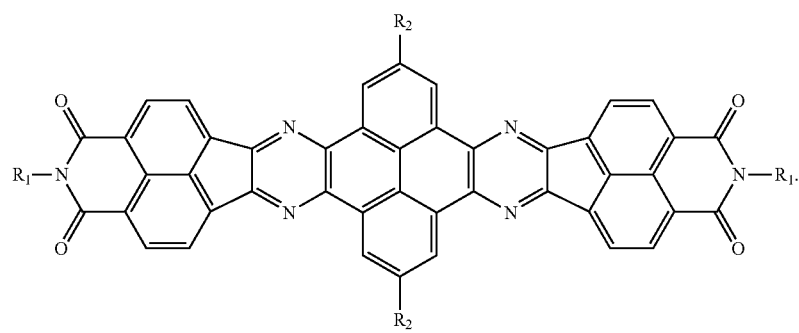
(XIX)
In some embodiments, the Type-A compound is selected from
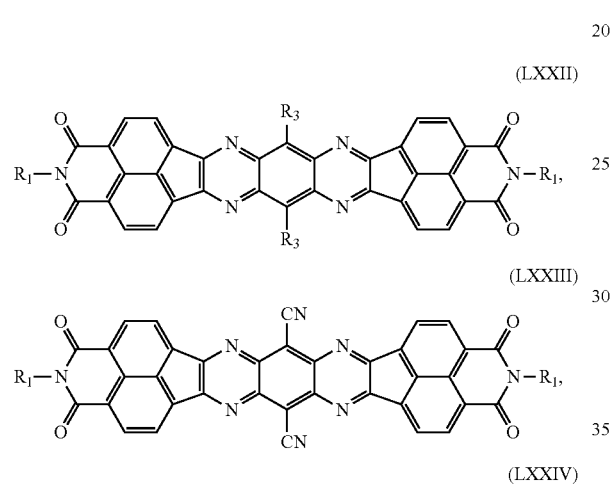
(LXXII)
(LXXIII)
(LXXIV)
(LXXV)
(LXXVI)
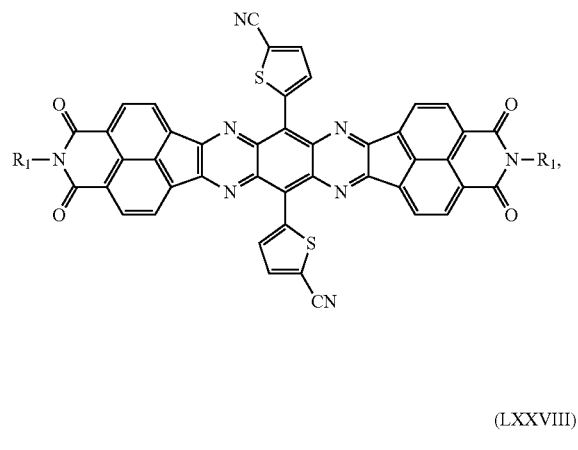
(LXXVII)
(LXXVIII)
(LXXIX)

In some embodiments, the Type-A compound can be represented by:

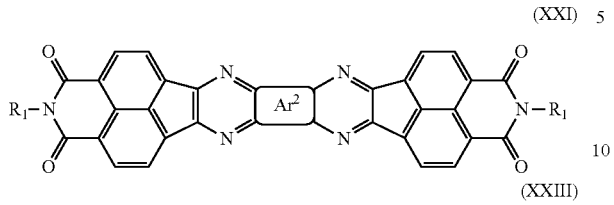
(XXI)

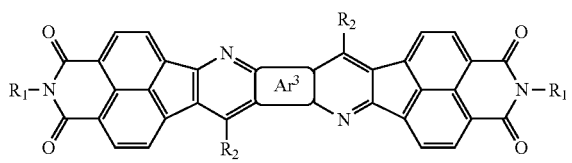
(XXIII)

wherein independently each of $Ar^2$ and $Ar^3$ comprises an optionally substituted aryl ring or an optionally substituted heteroaryl ring, or two or more of said rings fused together; and wherein $R_1$ and $R_2$ have the same definitions as previously described.

$Ar^2$ and $Ar^3$ can be independently selected from, for example, the following:

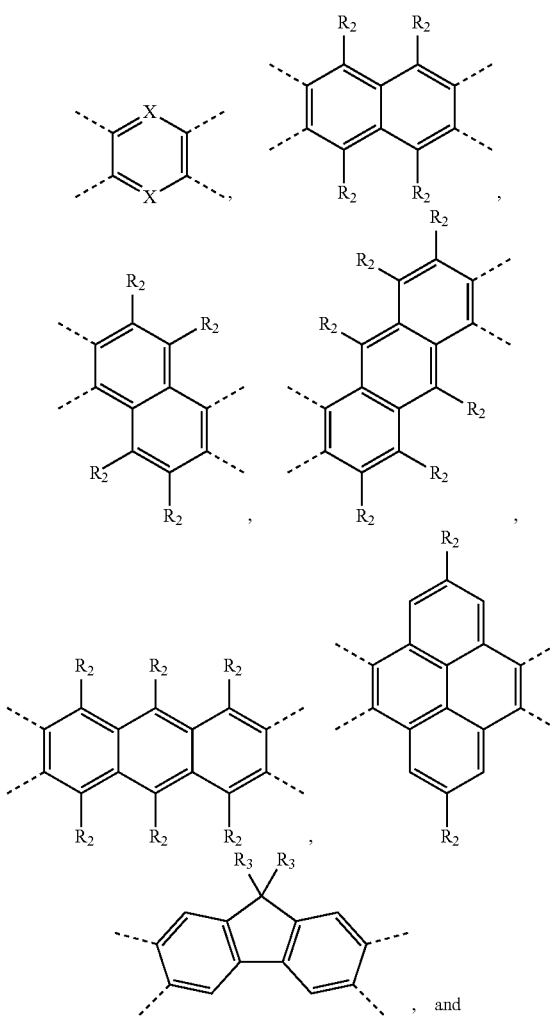
, and

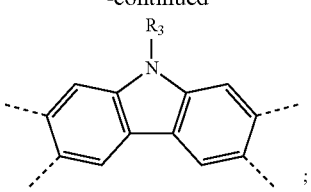
;

wherein X, $R_2$ and $R_3$ have the same definitions as previously described.

The molecule weight of the Type-A compound can be, for example, 5,000 or less, or 3,000 or less, or 2,000 or less, or 1,000 or less. The lower end of the molecular weight can be, for example, at least 500.

Methods for making Type-A Compound

The Type-A compound described herein can be made by, for example, reacting a diketo intermediate with a second compound represented by

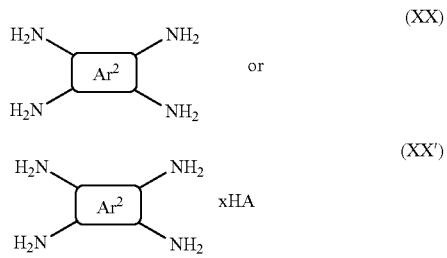

to obtain a third compound represented by

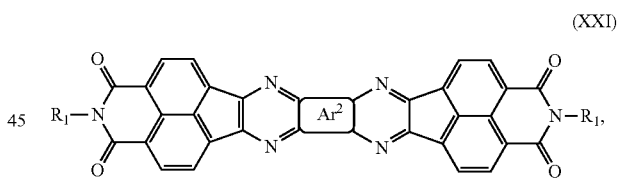
(XXI)

wherein $Ar^2$ and $R_1$ has the same definitions as previously described. The diketo intermediate is described in detail in Part I.

In one embodiment, $Ar^2$ comprises a six-membered ring not fused with another ring, compound (XX) and compound (XX') comprise two pairs of ortho-positioned primary amine groups on said ring. In another embodiment, $Ar^2$ comprises two or more rings fused together, and compound (XX) and compound (XX') comprise two pairs of ortho-positioned primary amine groups, with each pair linked to a different ring. HA can be, for example, hydrochloric acid (HCl), hydrobromic acid (HBr), hydroiodic acid (HI) or acetic acid (HOAc), sulfuric acid ($H_2SO_4$) or phosphoric acid ($H_3PO_4$); x can 1, 2, 3, or 4.

Further, the Type-A compound described herein can be made by, for example, reacting a monoketo intermediate with a second compound represented by

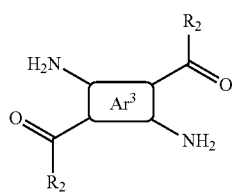
(XXII)

to obtain a third compound represented by

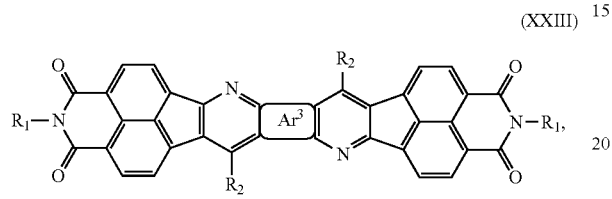
(XXIII)

wherein $Ar^3$, $R_1$ and $R_2$ have the same definitions as previously described. The monoketo intermediate is described in detail in Part I.

In one embodiment, $Ar^3$ comprises a six-membered ring not fused with another ring, and compound (XXII) comprises two pairs of ortho-positioned groups on said ring, with each pair comprising a primary amine group and a ketone group. In another embodiment, $Ar^3$ comprises two or more rings fused together, and compound (XXII) comprises two pairs of ortho-positioned groups, with each pair comprising a primary amine group and a ketone group, wherein each pair is linked to a different ring.

Part III—Type-A Oligomers and Polymers

Structure of Type-A Polymer

Many embodiments described herein relate to a Type-A polymer comprising one or more first repeating units RU1, wherein RU1 is represented by formula (XXIV):

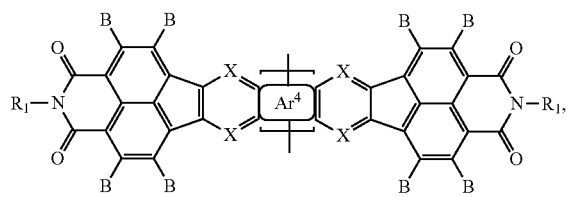
(XXIV)

wherein (i) $Ar^4$ comprises an optionally substituted aryl ring or an optionally substituted heteroaryl ring, or two or more of said rings fused together; (ii) X, B and $R_1$ have the same definitions as previously described.

For example, in some embodiments $Ar^4$ is represented by the following:

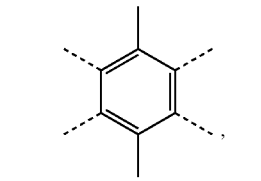

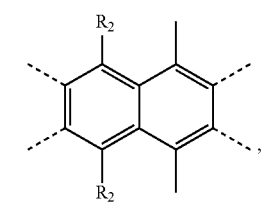

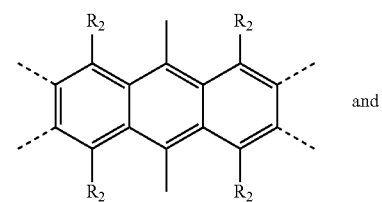
and

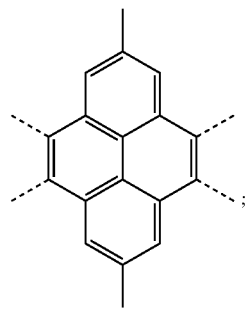

wherein X and $R_2$ have the same definitions as previously described.

In some embodiments, the one or more first repeating units RU1 are independently selected from formulae (XXV), (XXVI) and (XXVII)

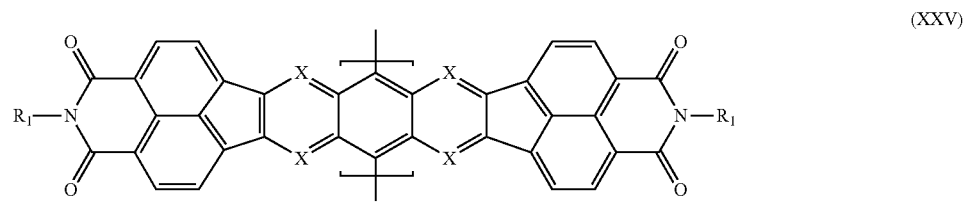
(XXV)

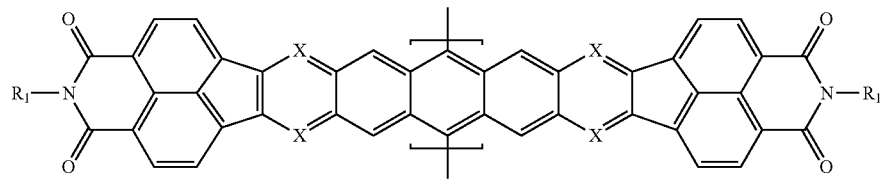

(XXVI)

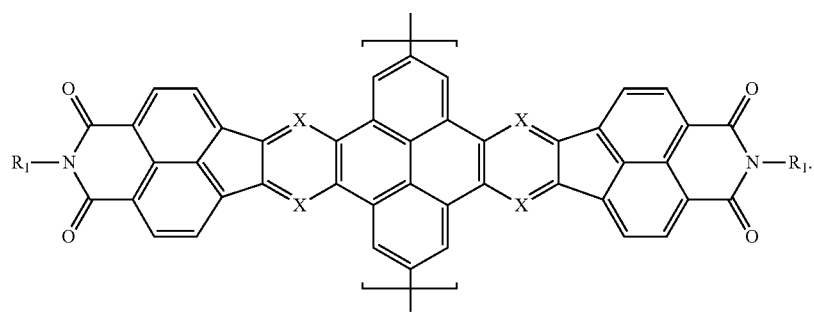

(XXVII)

The Type-A polymer can be, for example, a homopolymer represented by

(PA1)

The Type-A polymer can be, for example, a copolymer such as an alternating copolymer or a block copolymer.

In one embodiment, the Type-A polymer is an alternating copolymer represented by

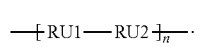

(PA2)

In one embodiment, the Type-A polymer is a block copolymer represented by

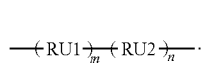

(PA3)

The copolymer can comprise, for example, at least two different RU1 repeating units.

In some embodiments, the Type-A polymer is a copolymer comprising one or more second repeating units RU2 selected from

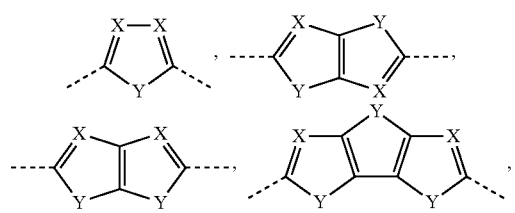

-continued

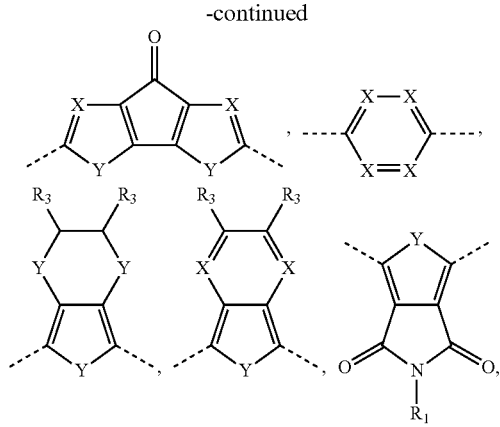

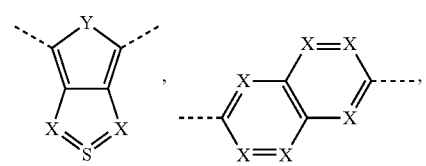

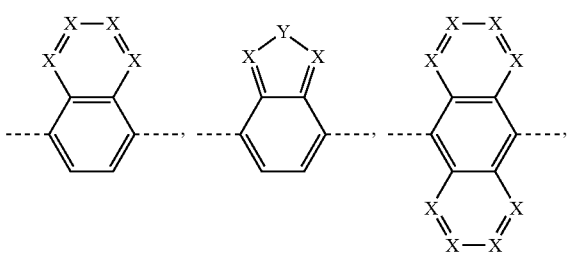

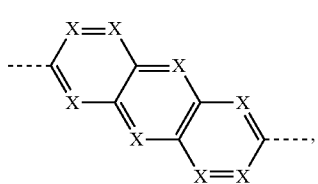

-continued

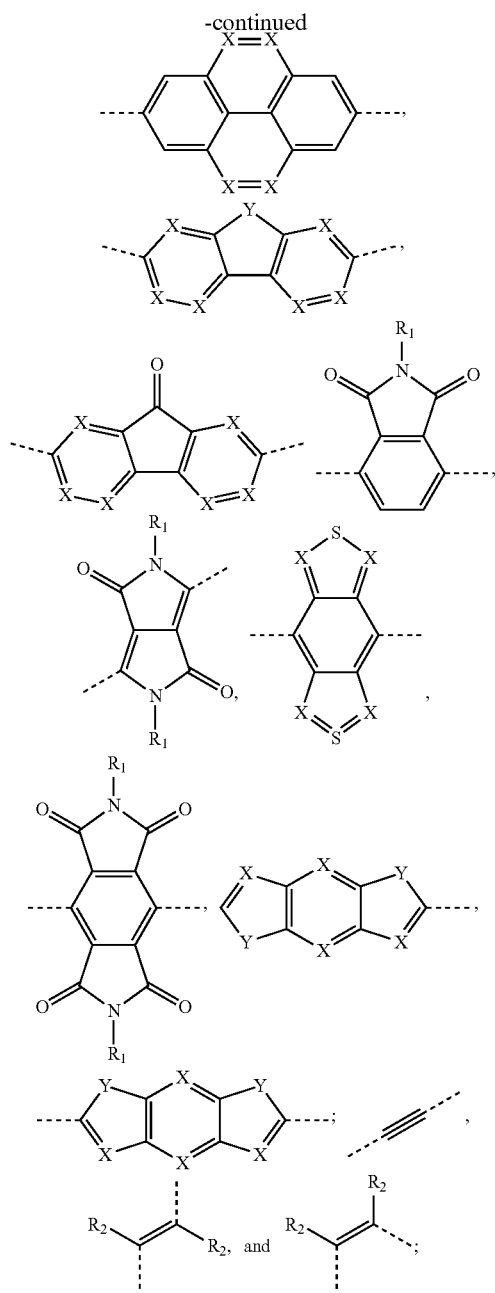

wherein X, Y, $R_1$, $R_2$ and $R_3$ have the same definitions as previously described.

In some embodiments, RU2 comprises at least one thiophene, selenophene, or thiazole ring. In some embodiments, RU2 comprises at least two or at least three rings fused together, optionally with at least one of said rings being a thiophene, selenophene, or thiazole ring. Particular embodiments of RU2 include optionally substituted thiophene, optionally substituted selenophene, optionally substituted thienothiophene and optionally substituted benzobisthiophene.

In one embodiment, the copolymer is an alternating copolymer, with the alternating section comprising at least one RU1 repeating unit and at least one RU2 repeating unit. In another embodiment, the copolymer is an alternating copolymer, with the alternating section comprising at least one RU1 repeating unit and at least two RU2 repeating units, said at least two RU2 units can be same or different. In a further embodiment, the copolymer is an alternating copolymer, with the alternating section comprising at least one RU1 repeating unit and at least three RU2 repeating units, said at least three RU2 units can be same or different. In an additional embodiment, the copolymer is an alternating copolymer, with the alternating section comprising at least two RU1 repeating units, said at least two RU1 units can be same or different.

In some embodiments, the Type-A polymer is selected from the following:

(XXVIII)

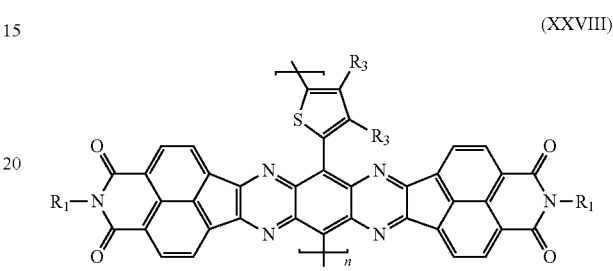

(XXIX)

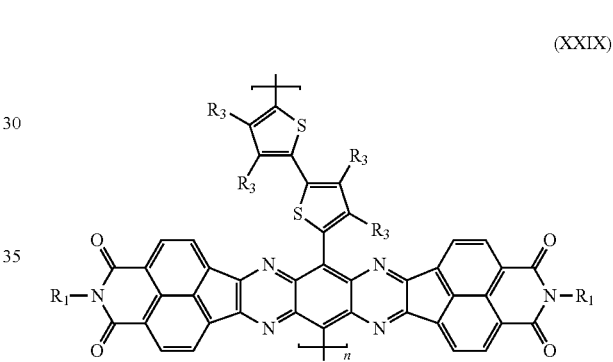

(XXX)

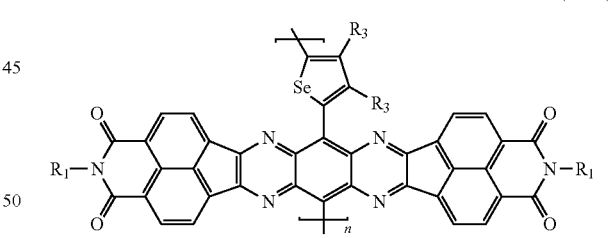

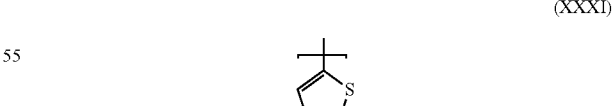

(XXXI)

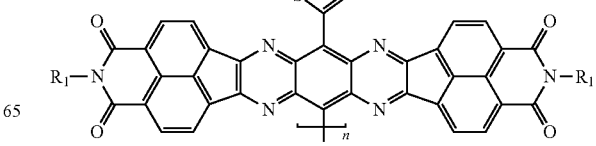

-continued (LXXX)

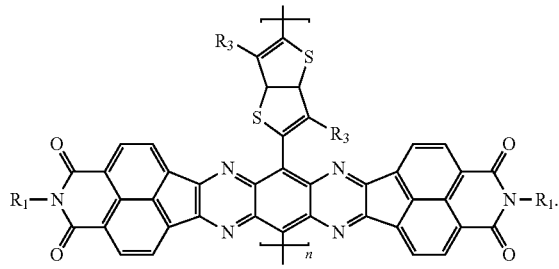

In these embodiments, n is a positive number, representing an average number of repeating units as known in the art of polymer chemistry. The weight average molecule weight (Mw) of the Type-A polymer can be, for example, 5,000 or more, or 10,000 or more, or 20,000 or more, or 50,000 or more, or 100,000 or more. The upper end of the molecular weight (Mw) range can be, for example, 2,000,000 or less, or 1,000,000 or less.

Methods for making Type-A Polymer

The Type-A monomer for the Type-A polymer described herein can be made by, for example, reacting a diketo intermediate with a second compound represented by (XXXII)

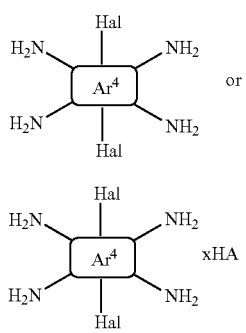

or (XXXII')

to obtain a third compound represented by (XXXIII)

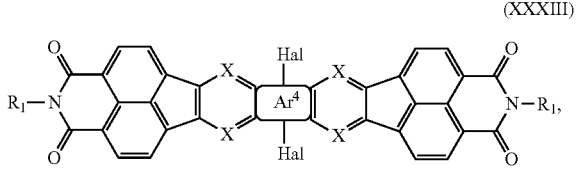

wherein $Ar^4$, $R_1$, X, Hal and HA have the same definitions as previously described. The diketo intermediate is described in detail in Part I. In one particular embodiment, Hal consists of Br. In one particular embodiment, X consists of N.

In one embodiment, $Ar^4$ comprises a six-membered ring not fused with another ring, and compound (XXXII) or (XXXII') comprises two pairs of ortho-positioned primary amine groups on said ring. In another embodiment, $Ar^4$ comprises two or more rings fused together, and compound (XXXII) or (XXXII') comprises two pairs of ortho-positioned primary amine groups, with each pair linked to a different ring.

From the Type-A monomer, the Type-A polymer can be made by, for example, Pd catalyzed coupling of the Type-A monomer with a di-tin derivative of RU2. The Type-A polymer can also be by Pd catalyzed coupling of any halogenated derivative of the RU1 with a di-tin derivative of RU2. Further, the halogenated derivative of the RU1 can also be used to make Type-A Compound by Pd catalyzed coupling with mono-tin derivative of RU2.

Part IV—Type-B Compound

Structure of Type-B Compound

Many embodiments described herein relate to a Type-B compound represented by formula (XXXIV):

(XXXIV)

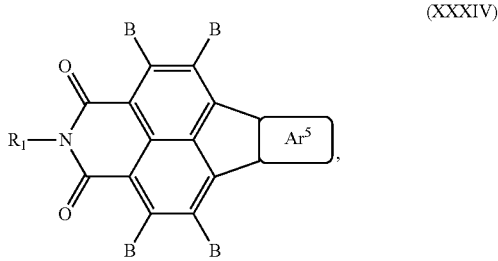

wherein: (i) $Ar^5$ comprises two or more rings fused together, each ring is an optionally substituted aryl ring or an optionally substituted heteroaryl ring; (ii) $R_1$ and B have the same definitions as previously described.

$Ar^5$ can be, for example, a heteroaryl group comprising in the heteroaromatic ring(s) one or more N heteroatoms, or two or more N heteroatoms, or three or more N heteroatoms, or four or more N heteroatoms. $Ar^5$ can be, for example, a heteroaryl group comprising one or more imine moieties, or two or more imine moieties, or three or more imine moieties, or four or more imine moieties.

Many embodiments of the Type-B compound described herein relate to a monomer (Type-B monomer) suitable for polymerization or copolymerization, wherein $Ar^5$ comprises one or more, or two or more polymerizable groups. Polymerizable groups are known in the art and include, for example, halogen atoms such as Br.

In some embodiments wherein B is hydrogen, the Type-B monomer compound is represented by formula (XXXV):

(XXXV)

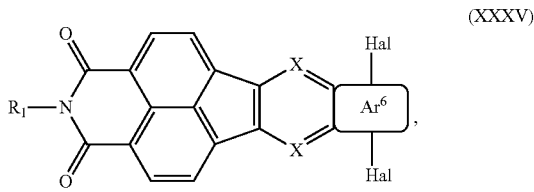

wherein: (i) $Ar^6$ comprises an optionally substituted aryl ring or an optionally substituted heteroaryl ring, or two or more of said rings fused together; (ii) Hal and X have the same definitions as previously described.

In some embodiments, the Type-B monomer is selected from formulae (XXXVI), (XXXVII), (XXXVIII), (XXXIX) and (XL):

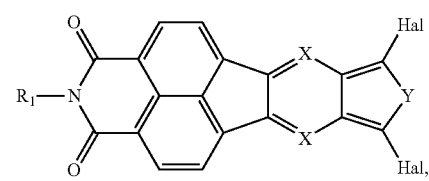
(XXXVI)

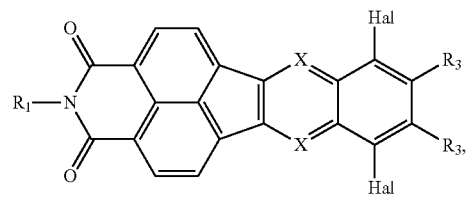
(XXXVII)

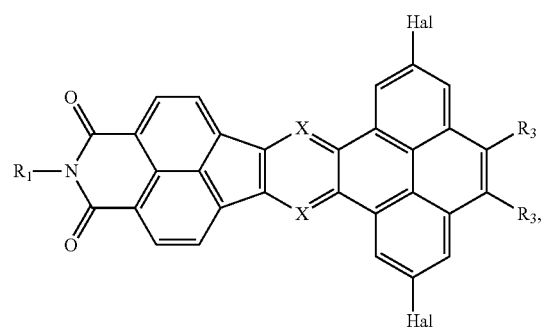
(XXXVIII)

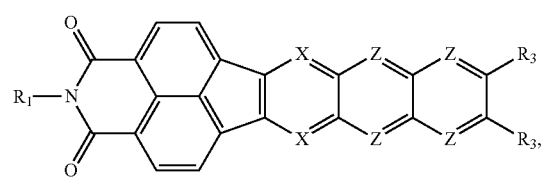
(XXXIX)

and

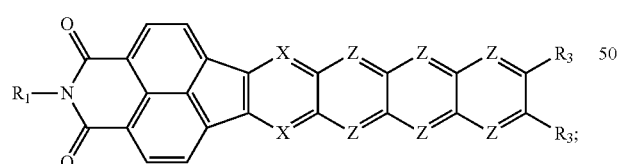
(XL)

wherein: (i) Z at each occurrence is independently selected from X and

;

(ii) Hal, X, Y and $R_1$ have the same definitions as previously described.

Particular embodiments of the Type-B monomer described herein include the following:

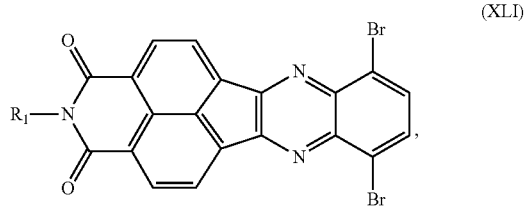
(XLI)

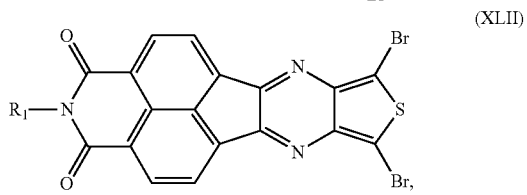
(XLII)

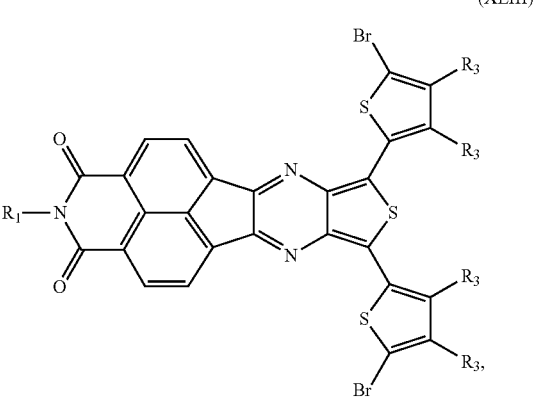
(XLIII)

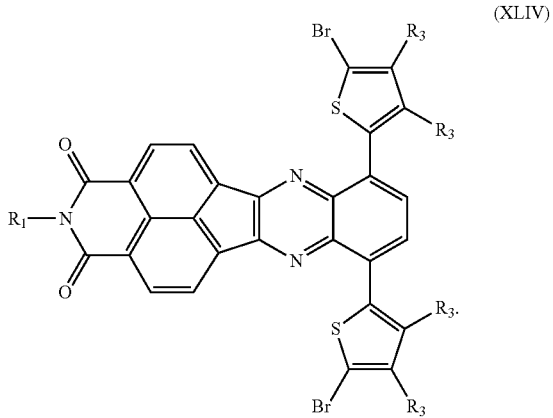
(XLIV)

Many embodiments of the Type-B compound described herein relate to a compound represented by formula (XLV):

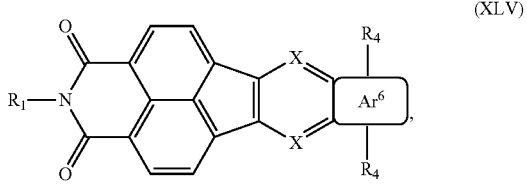
(XLV)

wherein: (i) $R_4$ at each occurrence comprises an end group and one or more conjugation side groups linking the end group and the aromatic group that $R_4$ is attached to; (ii) $Ar^6$, X, $R_1$, and the end group and the conjugation side group have the same definitions as previously described.

In some embodiments, $R_4$ can be a linear conjugated group comprising at least one, at least two or at least three conjugation side groups connected to each other with an end group attached. In some embodiments, the end group is selected from hydrogen, a linear or branched alkyl including —$CH_3$, and a linear or branched fluoroalkyl including —$CF_3$.

In some embodiments, the Type-B compound is selected from formulae (XLVI), (XLVII), (XLVIII), (XLIX) and (L):

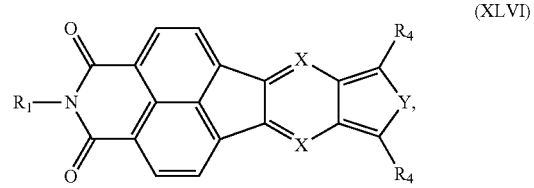
(XLVI)

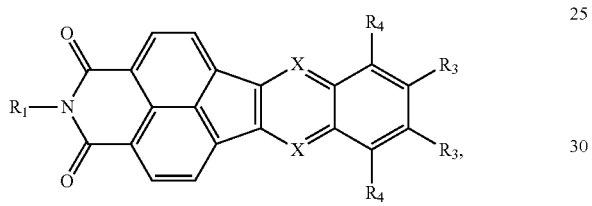
(XLVII)

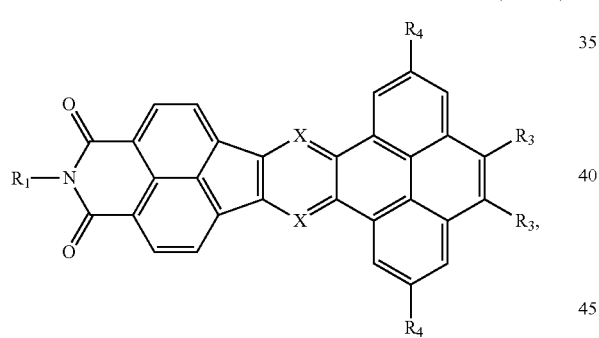
(XLVIII)

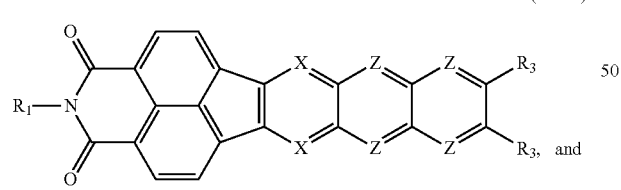
(XLIX)

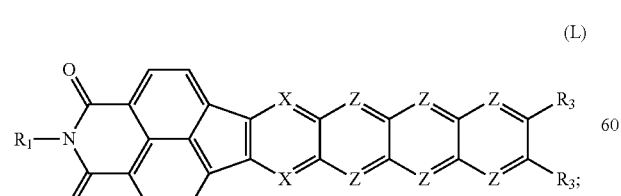
(L)

wherein X, Y, Z, $R_1$ and $R_4$ have the same definitions as previously described.

Particular embodiments of the Type-B compound described herein include the following:

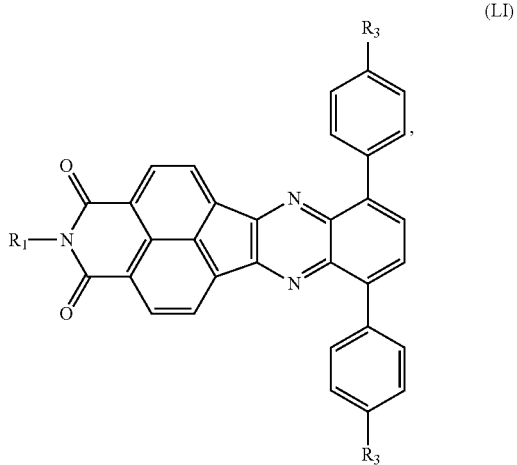
(LI)

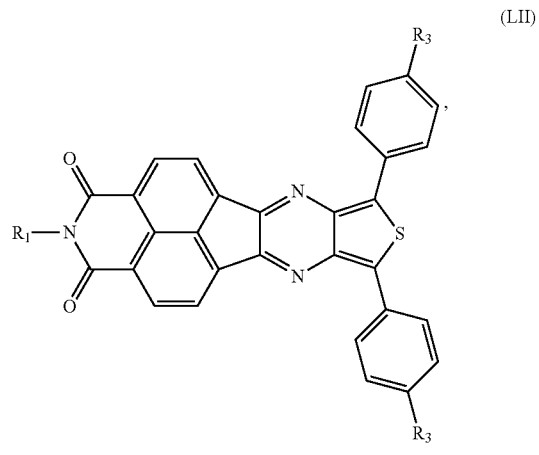
(LII)

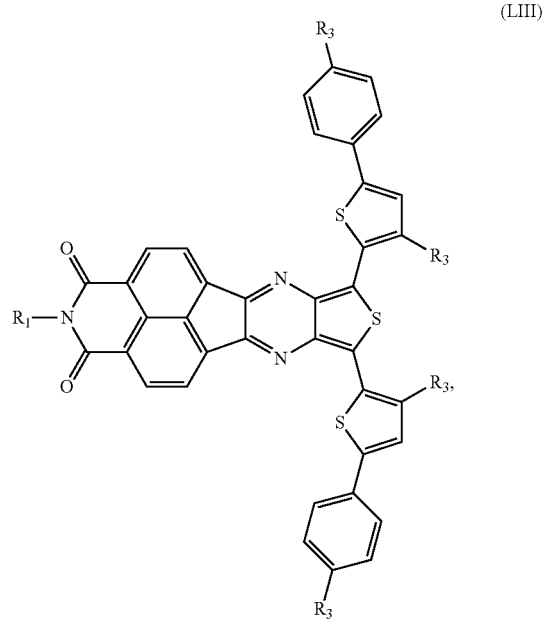
(LIII)

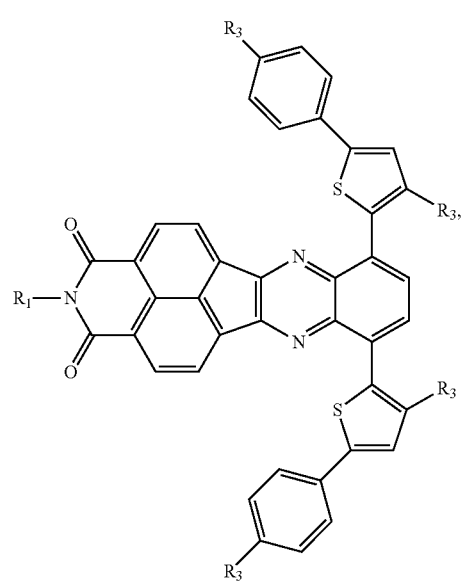
(LIV)
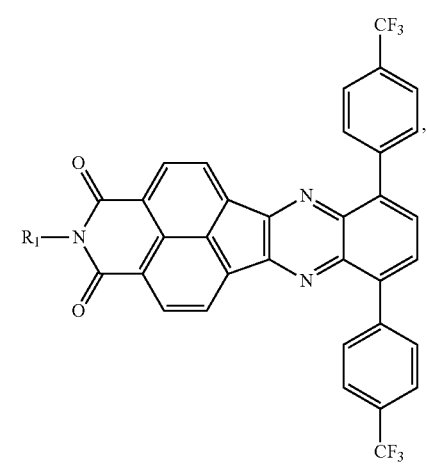
(LXXXI)
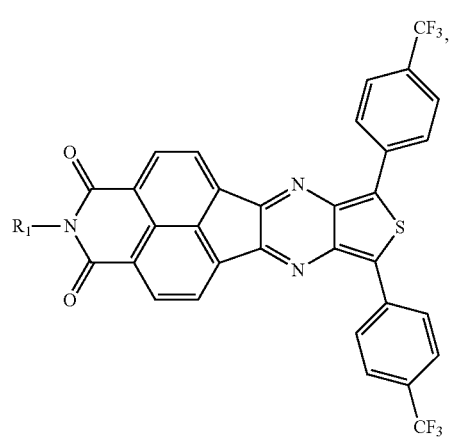
(LXXXII)
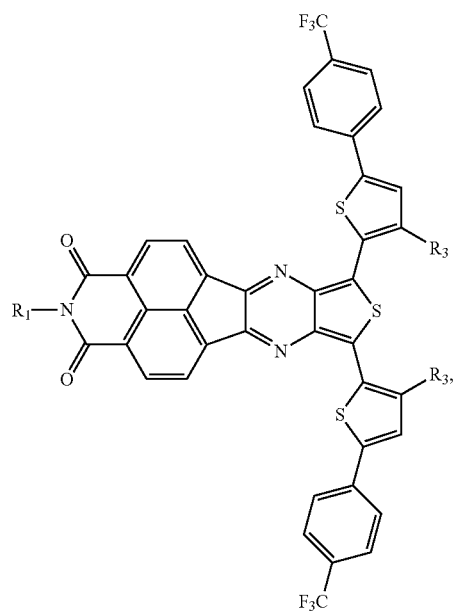
(LXXXIII)
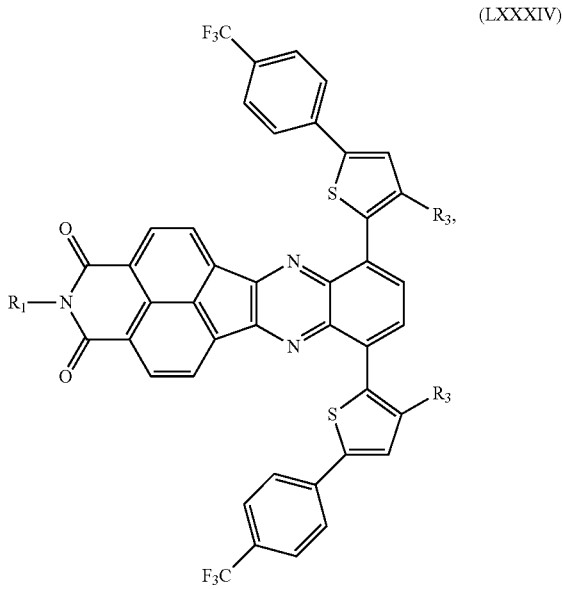
(LXXXIV)
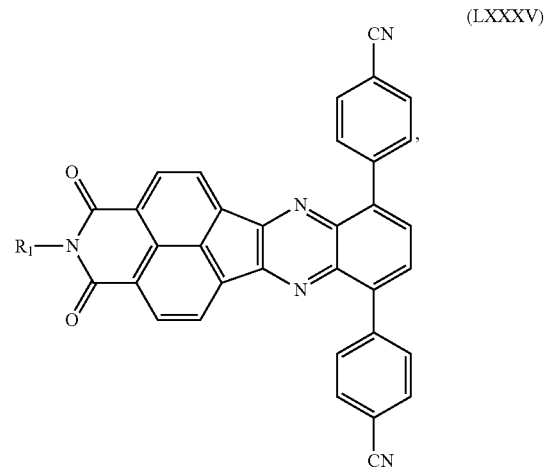
(LXXXV)

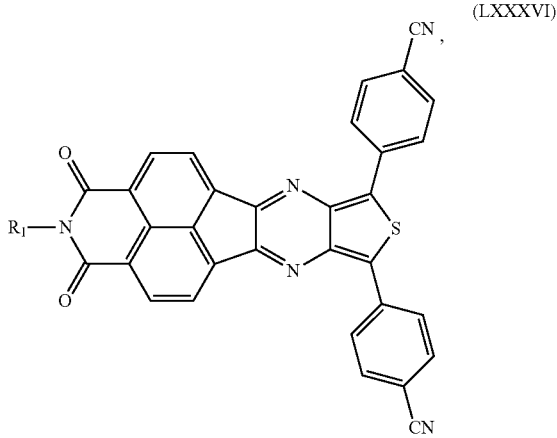

(LXXXVI)

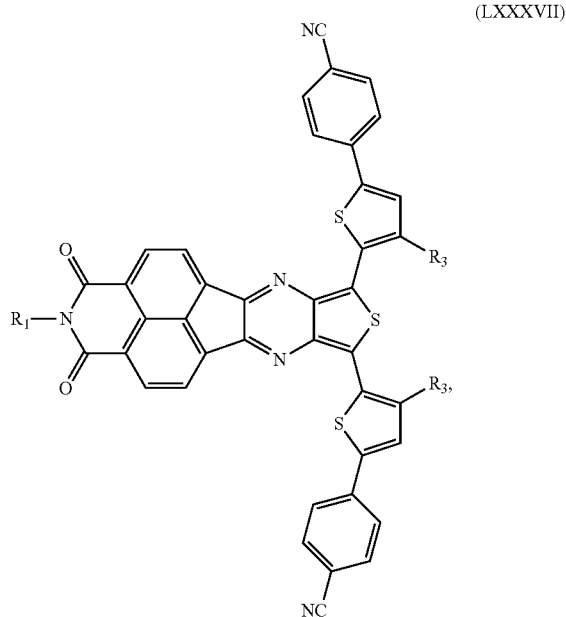

(LXXXVII)

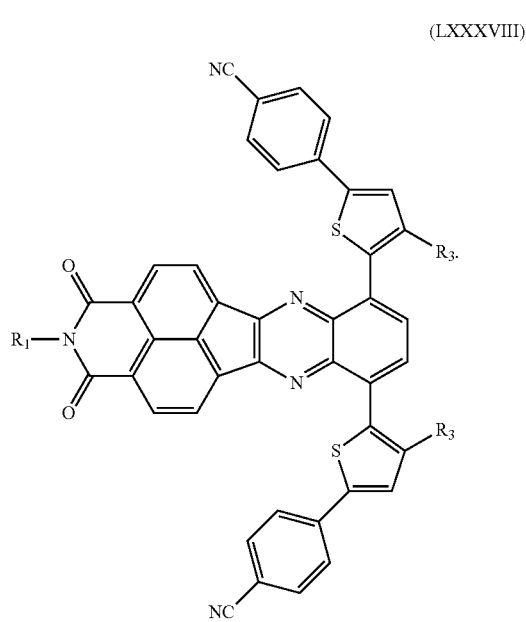

(LXXXVIII)

The molecule weight of the Type-B compound can be, for example, 5,000 or less, or 3,000 or less, or 2,000 or less, or 1,000 or less. The lower end of the molecular weight can be, for example, at least 500.

Methods for making Type-B Compound

The Type-B compounds described herein can be made by, for example, reacting a diketo intermediate with a second compound represented by

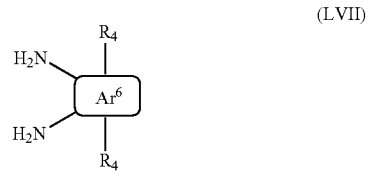

(LVII)

to obtain a third compound represented by

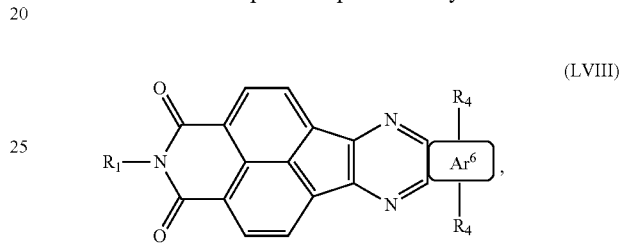

(LVIII)

wherein $Ar^6$, $R_1$ and $R_4$ have the same definitions as previously described. The diketo intermediate is described in detail in Part I.

In one embodiment, $Ar^6$ comprises a six-membered ring optionally fused with another ring, and compound (LVII) comprises one pair of ortho-positioned primary amine groups on said six-membered ring. In another embodiment, $Ar^6$ comprises a five-membered ring, and compound (LVII) comprises one pair of ortho-positioned primary amine groups on said five-membered ring.

Part V—Type-B Oligomers and Polymers

Structure of Type-B Polymer

Many embodiments described herein relate to a Type-B polymer of structure comprising one or more first repeating units RU3, wherein RU3 is represented by formula (LIX):

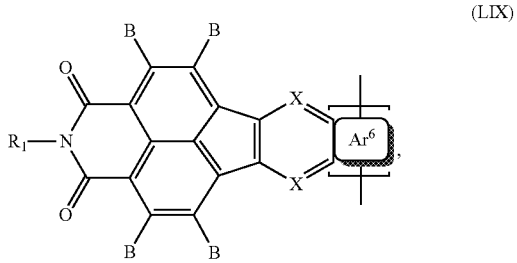

(LIX)

wherein (i) $Ar^6$ comprises an optionally substituted aryl ring or an optionally substituted heteroaryl ring, or two or more of said rings fused together; (ii) X, B and $R_1$ have the same definitions as previously described.

In some embodiments, the one or more first repeating units RU3 are selected from formulae (LX), (LXI), (LXII), (LXIII) and (LXIV)

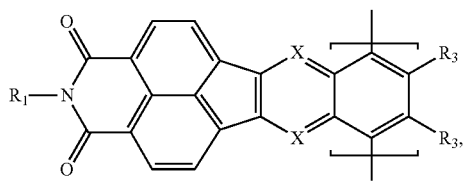
(LX)

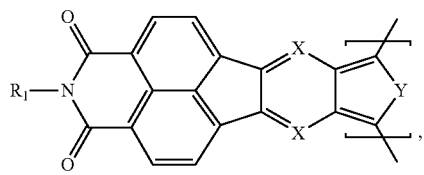
(LXI)

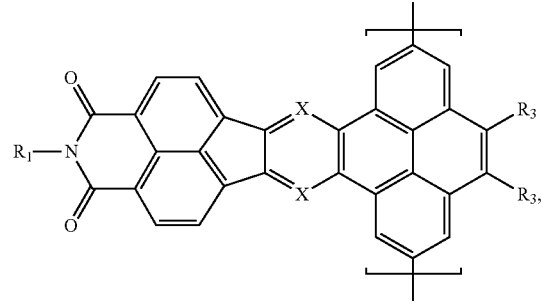
(LXII)

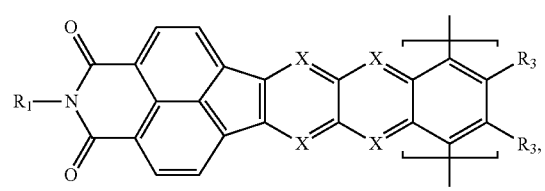
(LXIII)

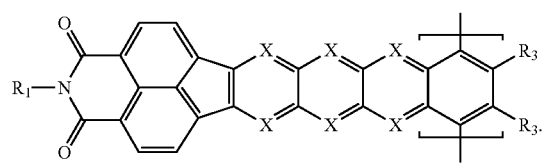
(LXIV)

The Type-B polymer can be, for example, a homopolymer represented by

(PB1)

The Type-B polymer can be, for example, a copolymer such as an alternating copolymer or a block copolymer. The copolymer can comprises, for example, at least two different RU3 repeating units.

In one embodiment, the Type-B polymer is an alternating copolymer represented by

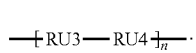
(PB2)

In one embodiment, the Type-B polymer is a block copolymer represented by

(PB3)

The copolymer can comprises, for example, at least two different RU3 repeating units.

In some embodiments, the Type-B polymer is a copolymer comprising one or more second repeating units RU4 selected from

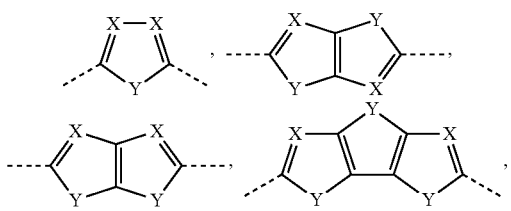

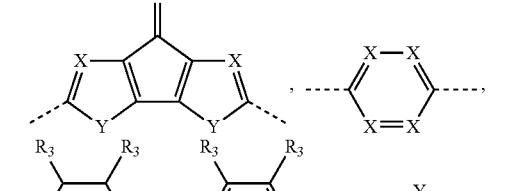

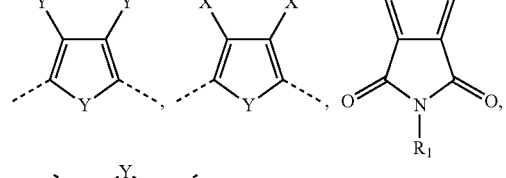

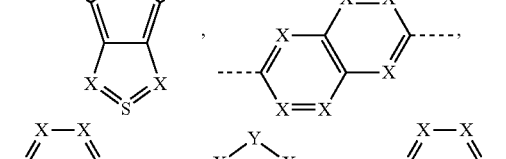

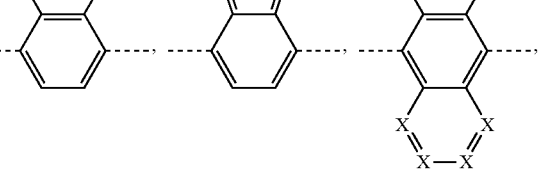

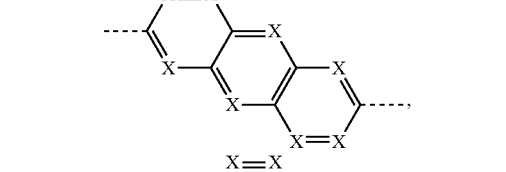

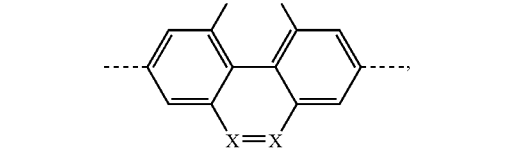

-continued

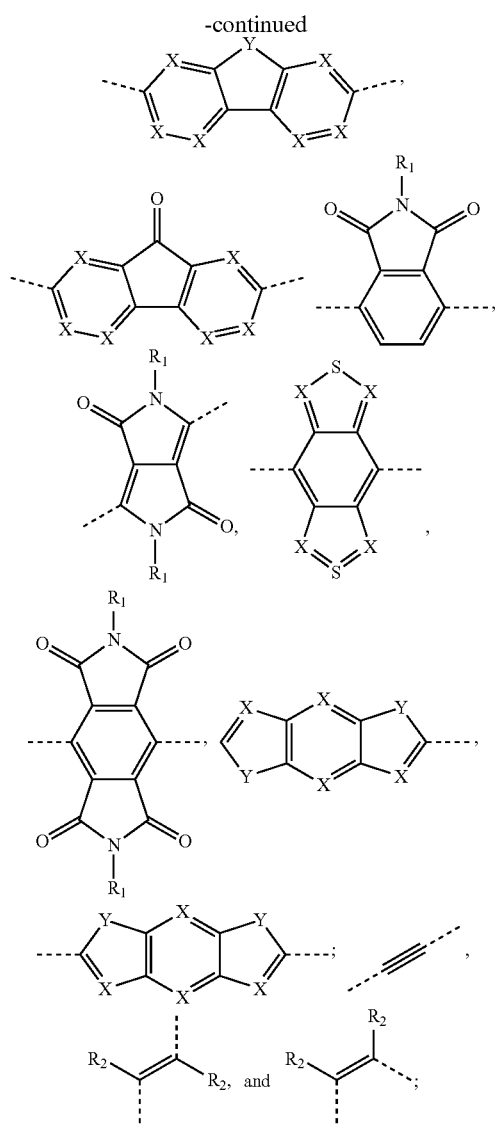

wherein X, Y, $R_1$, $R_2$ and $R_3$ have the same definitions as previously described.

In some embodiments, RU4 comprises at least one thiophene or selenophene ring. In some embodiments, RU4 comprises at least two or at least three rings fused together, optionally with at least one of said rings being a thiophene or selenophene ring. Particular embodiments of RU4 include optionally substituted thiophene, optionally substituted selenophene, optionally substituted benzobisthiophene, and optionally substituted fluorene.

In one embodiment, the copolymer is an alternating copolymer, with the alternating section comprising at least one RU3 repeating unit and at least one RU4 repeating unit. In another embodiment, the copolymer is an alternating copolymer, with the alternating section comprising at least one RU3 repeating unit and at least two RU4 repeating units, said at least two RU4 units can be same or different. In a further embodiment, the copolymer is an alternating copolymer, with the alternating section comprising at least one RU3 repeating unit and at least three RU4 repeating units, said at least three RU4 units can be same or different. In an additional embodiment, the copolymer is an alternating copolymer, with the alternating section comprising at least two RU3 repeating units, said at least two RU3 units can be same or different.

In some embodiments, the Type-B polymer is selected from the following

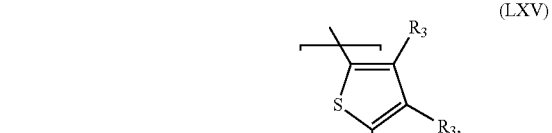

(LXV)

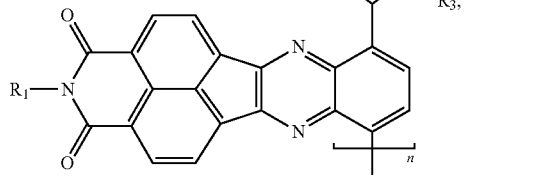

(LXVI)

(LXVII)

(LXVIII)

(LXIX)

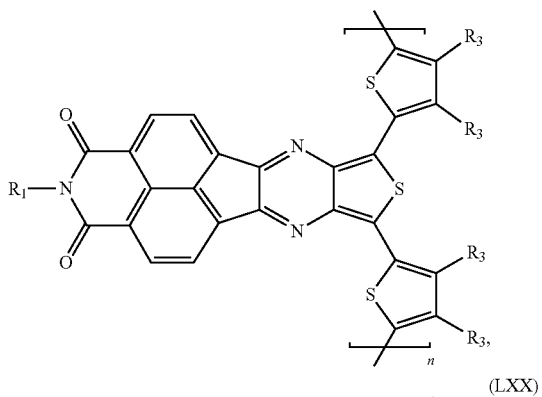

(LXX)

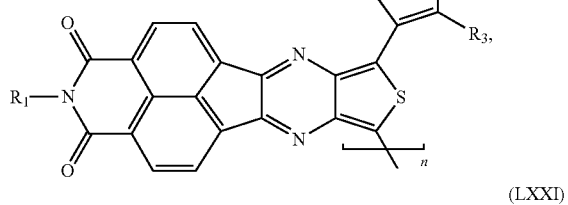

(LXXI)

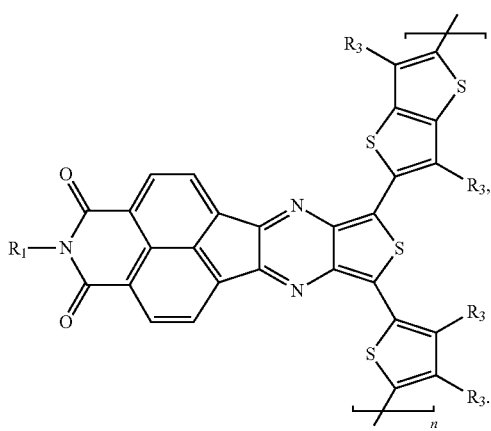

The weight average molecule weight (Mw) of the Type-B polymer can be, for example, 5,000 or more, or 10,000 or more, or 20,000 or more, or 50,000 or more, or 100,000 or more. The upper end of the molecular weight (Mw) range can be, for example, 2,000,000 or less, or 1,000,000 or less.

Methods for making Type-B Polymer

The Type-B monomer for the Type-B polymer described herein can be made by, for example, reacting a diketo intermediate with a second compound represented by (LV)

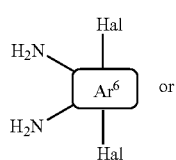 or (LV')

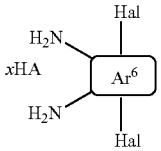

to obtain a third compound represented by (LVI)

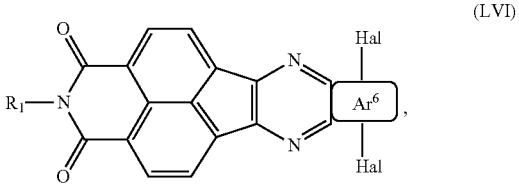

wherein $Ar^6$, $R_1$, Hal and HA have the same definitions as previously described. The diketo intermediate is described in detail in Part I. In some embodiments, x is 1 or 2. In a particular embodiment, Hal consists of Br.

In one embodiment, $Ar^6$ comprises a six-membered ring optionally fused with another ring, and compound (LV) comprises one pair of ortho-positioned primary amine groups on said six-membered ring. In another embodiment, $Ar^6$ comprises a five-membered ring optionally fused with another ring, and compound (LV) comprises one pair of ortho-positioned primary amine groups on said five-membered ring.

From the Type-B monomer, the Type-B polymer can be made by, for example, Pd catalyzed coupling of the Type-B monomer with a di-tin derivative of RU4. The Type-A polymer can also be by Pd catalyzed coupling of any halogenated derivative of the RU3 with a di-tin derivative of RU4. Further, the halogenated derivative of the RU3 can also be used to make Type-B Compound by Pd catalyzed coupling with mono-tin derivative of RU4.

Part VI—Devices

Organic Electronic Devices

The compounds and polymers described herein have advantageous electronic structures and solid morphologies for applications in organic electronic and optoelectronic devices. The electronic structures and the solid morphologies of the disclosed materials can also be fine tuned through variation of the chemical structures. Therefore, also provided are organic electronic devices and optoelectronic devices comprising one or more of the disclosed materials or formulations described herein such as organic field effect transistors (OFETs), thin film transistors (TFTs), logic circuits, integrated circuits, radio frequency identification tags (RFID), flat displays, organic photovoltaics (OPVs), solar cells, light emitting diodes (LEDs), light emitting transistor, etc. Also provided are the uses of the materials described herein as charge transporting, semiconducting, photoconducting, and/or light emitting components in electronic or optoelectronic devices.

In such devices, the disclosed materials are generally present as a thin film. In some embodiments, the disclosed materials have good solubility in common organic solvents; therefore they can be processed using solution processing techniques including spin coating, casting, dip coating, inkjet printing, screen printing, spray coating, doctor blade coating, roll coating, bar coating, die coating and dispense methods, and may also be employed in thermal evaporation or solution processes for making organic electronic devices. The solution can be prepared by dissolving the disclosed materials into a solvent or mixed solvents such as chloroform, dichloromethane, toluene, chlorobenzene, dichlorobenzene, trichlorobenzene, xylene, trifluoroacetic acid, formic acid, acetic acid, etc. at room temperature or at high temperature. The thickness of the thin films is not particularly specified and can be adjusted to fit the need of different applications.

Transistors

Many embodiments of the devices described herein relate to a field-effect transistor comprising at least one charge transporting material selected from Type-A compound, Type-A polymer, Type-B compound and Type-B polymer.

In some embodiment, the field-effect transistor comprises a thin-film of the charge transporting material described herein. The thin film can be deposited from a solution of the charge transporting material. The thin-film can be fabricated by spin coating. The thin-film can be fabricated by vacuum vapor deposition.

The field-effect transistor can be a n-channel transistor, or an ambipolar transistor. The electron mobility of the field-effect transistor can be, for example, $1 \times 10^{-5}$ cm$^2$/Vs or higher, or $1 \times 10^{-4}$ cm$^2$/Vs or higher, or $1 \times 10^{-3}$ cm$^2$/Vs or higher, or $1 \times 10^{-2}$ cm$^2$/Vs or higher, or 0.1 cm$^2$/Vs or higher. The on/off current ratio of the field-effect transistor can be, for example, at least $10^4$, or at least $10^5$, or at least $10^6$, or about $10^4$-$10^7$, or about $10^5$-$10^6$.

The organic thin film transistors described herein typically have a configuration such that a semiconductor layer including the compounds and/or polymers described herein is formed therein while also contacting the source electrode, drain electrode and insulating layer of the transistor.

The organic thin film transistor is typically thermally annealed Annealing is performed while the film is set on a substrate, and is believed (without wishing to be bound by theory) to allow for at least partial self-ordering and/or π-stacking of the compounds and/or polymers to occur in the solid state. The annealing temperature is determined depending on the property of the material, but is preferably from room temperature to 300° C., and more preferably from 50 to 300° C. In many embodiments, thermal annealing is carried out at least 150° C., or preferably above 170° C., or above 200° C. When the annealing temperature is too low, the organic solvent remaining in the organic film cannot be well removed therefrom. In contrast, when the annealing temperature is too high, the organic film can be thermally decomposed Annealing is preferably performed in a vacuum, or under nitrogen, argon or air atmosphere. In some embodiments annealing is performed in an atmosphere including a vapor of an organic solvent capable of dissolving the material so that the molecular motion of the material is accelerated, and thereby a good organic thin film can be prepared. The annealing time is properly determined depending on the aggregation speed of the material.

An insulating (dielectric) layer is used in the organic thin film transistors comprising the materials described herein, situated between the gate electrode and the organic thin film comprising the material. Various insulating materials can be used for the insulating layer. Specific examples of the insulating materials include inorganic insulating materials such as silicon oxide, silicon nitride, aluminum oxide, aluminum nitride, titanium oxide, tantalum oxide, tin oxide, vanadium oxide, barium strontium titanate, barium zirconate titanate, lead zirconium titanate, lead lanthanum titanate, strontium titanate, barium titanate, barium magnesium fluoride, bismuth tantalate niobate, hafnium oxide, and trioxide yttrium; organic insulating materials such as polymer materials, e.g., polyimide, polyvinyl alcohol, polyvinyl phenol, polystyrene, polyester, polyethylene, polyphenylene sulfide, unsubstituted or halogen-atom substituted polyparaxylylene, polyacrylonitrile, and cyanoethylpullulan; etc. These materials can be used alone or in combination. Among these materials, materials having a high dielectric constant and a low conductivity are preferably used.

Suitable methods for forming such an insulating layer include dry processes such as CVD methods, plasma CVD methods, plasma polymerization methods, and vapor deposition methods; wet processes such as spray coating methods, spin coating methods, dip coating methods, inkjet coating methods, cast coating methods, blade coating methods, and bar coating methods; etc.

In order to improve the adhesion between the insulating layer and organic semiconductor layer, to promote charge transport, and to reduce the gate voltage and leak current, an organic thin film (intermediate layer) can be employed between the insulating layer and organic semiconductor layer. The materials for use in the intermediate layer are not particularly limited as long as the materials do not chemically affect the properties of the organic semiconductor layer, and for example, molecular films of organic materials, and thin films of polymers can be used therefor. Specific examples of the materials for use in preparing the molecular films include coupling agents such as octadecyltrichlorosilane, octyltrichlorosilane, octyltrimethoxysilane, hexamethyldisilazane (HMDS), and octadecylphosphonic acid. Specific examples of the polymers for use in preparing the polymer films include the polymers mentioned above for use in the insulating layer. Such polymer films can serve as the insulating layer as well as the intermediate layer.

The materials of the electrodes (such as gate electrodes, source electrodes and drain electrodes) of the organic thin film transistor described herein are not particularly limited as long as the materials are electrically conductive. Specific examples of the materials include metals such as platinum, gold, silver, nickel, chromium, copper, iron, tin, antimony, lead, tantalum, indium, aluminum, zinc, tungsten, titanium, calcium, and magnesium; alloys of these metals; electrically conductive metal oxides such as indium tin oxide (ITO); inorganic or organic semiconductors, whose electroconductivity is improved by doping or the like, such as silicon single crystal, polysilicon, amorphous silicon, germanium, graphite, carbon nanotube, polyacetylene, polyparaphenylene, polythiophene, polypyrrole, polyaniline, polythienylenevinylene, polyparaphenylenevinylene, and complexes of polyethylenedioxythiophene (PEDOT) and polystyrene sulfonic acid.

Solar Cells

Solar cells described herein can be fabricated by, for example, first spin-coating a buffer layer, such as a PEDOT:PSS buffer layer, on top of an electrode and substrate, such as ITO-coated glass substrates (e.g., 10 Ω/sq, Shanghai B. Tree Tech. Consult Co., Ltd., Shanghai, China). Spin coating is known in the art and the spin coating can be adapted to the needs. One example s to spin coat at 1500 rpm for 60 s and dry at 150° C. for 10 min under vacuum. The thickness of the buffer layer (e.g., PEDOT) can be, for example, around 10 nm to 100 nm, or about 40 nm.

The active layer of the solar cells comprising the compounds and/or polymers described herein can comprise a mixed "heterojunction" active layer that is a phase separated blend of the materials described herein and an electron donor material. The electron donor materials can be a variety of organic materials (small molecules, oligomers, polymers, or polymer composites) that have a LUMO energy level that is at least about 0.2 to 0.6 eV more positive than the LUMO energy level of the compounds described herein, and a HOMO energy level that is more positive than the HOMO energy level of the compounds described herein.

In many embodiments of the solar cells described herein, a composite or composition comprising a solution or dispersion of one or more of the material described herein and one or more donor materials (for example P3HT or poly[(4,4'-bis(3-(2-ethyl-hexyl)dithieno[3,2-b:2',3'-d]silole)-2,6-diyl-alt-(2,5-bis(3-(2-ethyl-hexyl)thiophen-2yl)thiazolo[5,4-d]thiazole)] (PSEHTT, see CN102782011A, EP2493960A1, US20120273732, and Subramaniyan et al., *Adv. Energy Mater.* 2011, 1, 854-860) is spin-coated on top of the PEDOT:PSS layer to form a layer comprising the one or more material described herein and one or more electron donating materials.

The active layer of the solar cells comprising the compounds and/or polymers described herein can comprise a mixed "heterojunction" active layer that is a phase separated blend of the materials described herein and an electron acceptor material. The electron acceptor material can comprise a variety of organic materials (small molecules, oligomers, polymers, or polymers) that have a LUMO energy level that is at least about 0.2 to 0.6 eV more negative than the LUMO energy level of the polymers described herein, and a HOMO energy level that is more negative than the HOMO energy level of the polymers described herein. In many embodiments, the electron acceptor material can be a fullerene or a modified fullerene (e.g., $C_{61}$-phenyl-butyric acid methyl ester, $PC_{61}BM$, or $C_{71}$-phenyl-butyric acid methyl ester, $PC_{71}BM$). In other embodiments, the electron acceptor material can be an electron accepting semiconducting organic small molecule, oligomer, or polymer having appropriate LUMO and HOMO energies (at least about 0.2-0.6 eV more negative than the LUMO energy level and a more negative HOMO energy level than the HOMO energy level of the polymers described herein). Examples of such electron acceptor materials can include small molecules, oligomers, polymers, or polymers having highly electron deficient functional groups, such as for example naphthalene diimide, perylene diimide, rylene, phthalimide, and related derivatives comprising electron accepting groups.

In some embodiments of the solar cells described herein, a composition comprising a solution or dispersion of one or more of materials described herein and one or more acceptor materials (for example fullerene derivatives) is spin-coated on top of the buffer layer, such as PEDOT:PSS layer, for example at a suitable speed as known in the art, e.g. at 1000 rpm for 30 seconds, to form a layer comprising the one or more materials described herein and one or more electron accepting materials. In some embodiments, the solution or dispersion is applied using a hot solvent, and dried under vacuum immediately after the deposition the polymers.

The coated device precursor can then be annealed, for example on a hot plate at in a glove box, to form the active layer. The active layer can also be spin-coated in air and dried in a vacuum oven without thermal annealing. The solvents for dissolving the mixture of the material described herein and the electron donors, or the mixture of the material described herein and the electron acceptors, can be chloroform, chlorobenzene, 1,2-dichlorobenzene, etc. The solvents for the blend can be a single solvent such as chloroform, chlorobenzene, 1,2-dichlorobenzene or a mixture of two or three different solvents, the second (third) solvent can be 1,8-diiodooctane, 1,8-dibromoctane, 1,8-octanedithiol, etc. Optionally, the solvents can be heated so as to increase the solubility of the material described herein and/or the electron donors or the electron acceptors, as an aid to film formation.

Thermal annealing is believed to induce at least partial phase separation between the material described herein and the electron donors, or between the material described herein and the electron acceptors, forming the "heterojunctions" on the nanometer scale that are believed to be the site of light-induced charge separation.

After cooling down, the solar cell precursors comprising the active material-coated substrates can be taken out of the glove box and loaded in a thermal evaporator (e.g., BOC Edwards, 306) for the deposition of the cathode. The cathode consisting of, for example, 1.0 nm LiF and 80 nm aluminum layers, can be sequentially deposited through a shadow mask on top of the active layers in a vacuum of, for example, $8 \times 10^{-7}$ torr. Each substrate can contain, for example, a plurality of (e.g. 5) solar cells with an active area of, for example, 4 $mm^2$.

Solar cells described herein can also be fabricated by, for example, first spin-coating a buffer layer, such as a ZnO, on top of an electrode and substrate, such as ITO-coated glass substrates (e.g., 10 Ω/sq, Shanghai B. Tree Tech. Consult Co., Ltd., Shanghai, China). Spin coating is known in the art and the spin coating can be adapted to the needs. One example is to spin coat at 1500 rpm for 60 s and dry at 200° C. for 60 min in air. The thickness of the buffer layer (e.g., ZnO) can be, for example, around 10 nm to 100 nm, or about 30 nm.

The active layer of the solar cells comprising the compounds and/or polymers described herein can comprise a mixed "heterojunction" active layer that is a phase separated blend of the materials described herein and an electron donor material. The electron donor materials can be a variety of organic materials (small molecules, oligomers, polymers, or polymer composites) that have a LUMO energy level that is at least about 0.2 to 0.6 eV more positive than the LUMO energy level of the compounds described herein, and a HOMO energy level that is more positive than the HOMO energy level of the compounds described herein.

In many embodiments of the solar cells described herein, a composite or composition comprising a solution or dispersion of one or more of the materials described herein and one or more donor materials (for example P3HT or poly[(4,4'-bis(3-(2-ethyl-hexyl)dithieno[3,2-b:2',3'-d]silole)-2,6-diyl-alt-(2,5-bis(3-(2-ethyl-hexyl)thiophen-2yl)thiazolo[5,4-d]thiazole)] (PSEHTT, see CN102782011A, EP2493960A1, US20120273732, and Subramaniyan et al., *Adv. Energy Mater.* 2011, 1, 854-860) is spin-coated on top of the ZnO layer to form a layer comprising the one or more material described herein and one or more electron donating materials.

The active layer of the solar cells comprising the compounds and/or polymers described herein can comprise a mixed "heterojunction" active layer that is a phase separated blend of the materials described herein and an electron acceptor material. The electron acceptor material can comprise a variety of organic materials (small molecules, oligomers, polymers, or polymers) that have a LUMO energy level that is at least about 0.2 to 0.6 eV more negative than the LUMO energy level of the polymers described herein, and a HOMO energy level that is more negative than the HOMO energy level of the polymers described herein. In many embodiments, the electron acceptor material can be a fullerene or a modified fullerene (e.g., $C_{61}$-phenyl-butyric acid methyl ester, $PC_{61}BM$, or $C_{71}$-phenyl-butyric acid methyl ester, $PC_{71}BM$). In other embodiments, the electron acceptor material can be an electron accepting semiconducting organic small molecule, oligomer, or polymer having appropriate LUMO and HOMO energies (at least about 0.2-0.6 eV more negative than the LUMO energy level and a more negative HOMO energy level than the HOMO energy level of the polymers described herein). Examples of such electron acceptor materials can include small molecules, oligomers, polymers, or polymers having highly electron deficient functional groups, such as for example naphthalene diimide, perylene diimide, rylene, phthalimide, and related derivatives comprising electron accepting groups.

In some embodiments of the solar cells described herein, a composition comprising a solution or dispersion of one or more of materials described herein and one or more acceptor materials (for example fullerene derivatives) is spin-coated on top of the buffer layer, such as ZnO layer, for example at a suitable speed as known in the art, e.g. at 1000 rpm for 30 seconds, to form a layer comprising the one or more materials described herein and one or more electron accepting materials. In some embodiments, the solution or dispersion is applied using a hot solvent, and dried under vacuum immediately after the deposition the polymers.

The coated device precursor can then be annealed, for example on a hot plate in a glove box, to form the active layer. The active layer can also be spin-coated in air and dried in a vacuum oven without thermal annealing. The solvents for dissolving the mixture of the material described herein and the electron donors, or the mixture of the material described herein and the electron acceptors, can be chloroform, chlorobenzene, 1,2-dichlorobenzene, etc. The solvents for the blend can be a single solvent such as chloroform, chlorobenzene, 1,2-dichlorobenzene or a mixture of two or three different solvents, the second (third) solvent can be 1,8-diiodooctane, 1,8-dibromoctane, 1,8-octanedithiol, etc. Optionally, the solvents can be heated so as to increase the solubility of the material described herein and/or the electron donors or the electron acceptors, as an aid to film formation.

Thermal annealing is believed to induce at least partial phase separation between the material described herein and the electron donors, or between the material described herein and the electron acceptors, forming the "heterojunctions" on the nanometer scale that are believed to be the site of light-induced charge separation.

After cooling down, the solar cell precursors comprising the active material-coated substrates can be taken out of the glove box and loaded in a thermal evaporator (e.g., BOC Edwards, 306) for the deposition of the anode. The anode consisting of, for example, 10.0 nm $MoO_3$ and 100 nm Ag, can be sequentially deposited through a shadow mask on top of the active layers in a vacuum of, for example, $8 \times 10^{-7}$ torr. Each substrate can contain, for example, a plurality of (e.g. 5) solar cells with an active area of, for example, 4 mm$^2$.

WORKING EXAMPLES

Part I

Example 1A

Synthesis of Diketone Intermediates

Materials and Methods:

Unless stated otherwise, starting materials were purchased and used without further purification.

$^1$H NMR and $^{13}$C NMR spectra were recorded on a Bruker AV500 at 500 MHz using either deuterochloroform (CDCl$_3$) or deuterotrifluoroacetic acid (CF$_3$COOD) as the solvent.

Mass spectra were obtained from Bruker AutoFlex II Matrix-Assisted LASER Desorption Ionization—Time of Flight Mass Spectrometer (MALDI-TOF) using benzo[α] pyrene as a matrix recorded in a (+)-reflector mode.

Thermogravimetric analysis of the molecules was conducted on a TA Instruments model Q50TGA. A heating rate of 10° C./min under a flow of N$_2$ was used with runs conducted from room temperature to 800° C.

Cyclic voltammetry was done on an EG&G Princeton Applied Research potentiostat/galvanostat (model 273A). Data were analyzed by using a Model 270 Electrochemical Analysis System Software on a PC computer. A three-electrode cell was used, using platinum wire electrodes as both counter and working electrode. Silver/silver ion (Ag in 0.1 M AgNO$_3$ solution, Bioanalytical System, Inc.) was used as a reference electrode. Ferrocene/ferrocenium (Fc/Fc$^+$) was used as an internal standard. All solutions were purged with N$_2$ for 20 min before each experiment.

UV-Vis absorption spectra were collected on a Perkin-Elmer model Lambda 900 UV/Vis/near-IR spectrophotometer.

The photoluminescence (PL) emission spectra were obtained with a Photon Technology International (PTI) Inc. model QM2001-4 spectrofluorimeter.

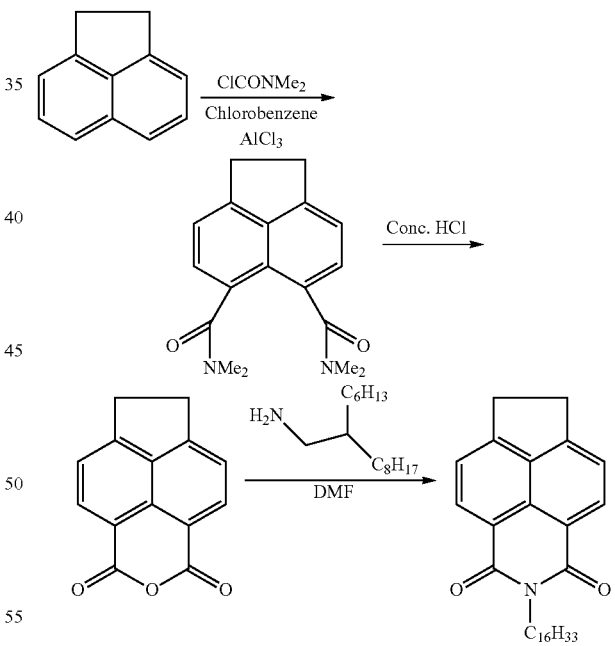

Synthesis of N5,N5,N6,N6-tetramethyl-1,2-dihydroacenaphthylene-5,6-dicarboxamide (Trost et al., *J. Am. Chem. Soc.* 1971, 93, (3), 737-745). Under N$_2$, 1,2-dihydroacenaphthylene (12 g, 77.9 mmol) and dimethylcarmonyl chloride were dissolved in 120 mL of chlorobenzene. The solution was then cooled to 0° C. followed by adding 28 g of AlCl$_3$ portion-wise. The mixture was slowly hearted to 80° C. After stirring at 80° C. for 4 hours, the solution was cooled back to 0° C. and additional 14 g of dimethylcarmonyl chloride and 19 g of AlCl₃ were added. The dark solution was refluxed for additional 2-4 hours. The solution was cooled to room temperature and poured into 800 mL of cold aqueous hydrochloric acid solution (5%). The organic phase was extracted with chloroform, washed subsequently with sodium bicarbonate solution and water, and dried over sodium sulfate. After removal of the solvents in vacuo, the residue solid materials were dissolved in hot ethanol. Crystals formed in 12 hours and were collected by filtration (more crystals formed from the mother liquid. Crystals can also formed directly from hot chlorobenzene solution). Yield: 15.4 mg (66.7%). ¹H NMR (CDCl₃, 500.046 MHz): δ=7.40 (d, 2H, ³J=7.0 Hz, Np), 7.33 (d, 2H, ³J=7.0 Hz, Np), 3.43 (s, 4H, CH₂), 3.11 (s, 9H, CH₃), 2.89 (s, 9H, CH₃).

Synthesis of 1,2-dihydroacenaphthylene dicarboxylic acid anhydride

N5,N5,N6,N6-tetramethyl-1,2-dihydroacenaphthylene-5,6-dicarboxamide (4.0 g, 13.5 mmol) was suspended in 10 mL of concentric hydrochloric acid. The mixture was heated to reflux for 4-5 hours. The solution was then cooled to 0° C. The off-white precipitate was collected by filtration and washed with cold water. The crude materials were recrystallized from hot acetic anhydride solution to afford pure product as light brown needles. Yield (2.08 g, 68.7%). ¹H NMR (CDCl₃, 500.046 MHz): δ=8.54 (d, 2H, ³J=7.0 Hz, Np), 7.65 (d, 2H, ³J=7.0 Hz, Np), 3.45 (s, 4H, CH₂).

Synthesis of N-hexyldecyl-1,2-dihydroacenaphthylene dicarboxylic acid imide

Under N₂, 1,2-dihydroacenaphthylene dicarboxylic acid anhydride (1.2 g, 5.36 mmol) and 2-hexyldecan-1-amine (1.5 g, 6.22 mmol) were dissolved in 15 mL of DMF. The solution was slowly heated to 90° C. for 12 hours and to 110° C. for additional 12 hours. After cooling back to room temperature, water was added to quench the reaction. The organic phase was extracted with chloroform, washed subsequently with water and brine, dried over sodium sulfate. After removal of the solvents, the crude materials were further purified by column chromatography with hexanes: chloroform (2v:1v) as the eluent. Yield (1.56, 65.1%). ¹H NMR (CDCl₃, 500.046 MHz): δ=8.51 (d, 2H, ³J=7.0 Hz, Np), 7.58 (d, 2H, ³J=7.0 Hz, Np), 4.14 (d, ³J=7.0 Hz, 4H, Hexyldecyl-CH₂), 3.59 (s, 4H, CH₂), 2.01 (m, 1H, hexyldecyl-CH), 1.5-1.2 (m, 24H, hexyldecyl-CH₂), 0.87 (m, 6H, hexyldecyl-CH₃).

Synthesis of N-decyltetradecyl-1,2-dihydroacenaphthylene dicarboxylic acid imide N-decyltetradecyl-1,2-dihydroacenaphthylene dicarboxylic acid imide was prepared similarly as N-hexyldecyl-1,2-dihydroacenaphthylene dicarboxylic acid imide by using 1,2-dihydroacenaphthylene dicarboxylic acid anhydride (1.2 g, 5.36 mmol) and 2-decyltetradecan-1-amine (2.20 g, 6.22 mmol). Yield (2.40, 69.1%). ¹H NMR (CDCl₃, 500.046 MHz): δ=8.48 (d, 2H, ³J=7.0 Hz, Np), 7.58 (d, 2H, ³J=7.0 Hz, Np), 4.14 (d, ³J=7.0 Hz, 4H, CH₂), 3.59 (s, 4H, CH₂), 2.01 (m, 1H, CH), 1.5-1.2 (m, 40H, CH₂), 0.87 (m, 6H, CH₃).

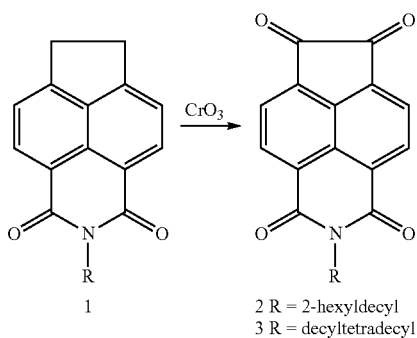

1

2 R = 2-hexyldecyl
3 R = decyltetradecyl

Compound 3. At 110° C., compound 1 (3.0 g, 5.36 mmole) was dissolved in 150 mL of acetic anhydride. After cooling back to room temperature, CrO₃ (1.6 g, 16.0 mmole) was added in portions. The solution was slowly warmed up to 50-80° C. and kept stirring for 4 hours. The dark green suspension was slowly poured onto 200 g of crushed ice. The crude material was extracted with CHCl₃, washed subsequently with water and brine. After removal of all the solvents, the solid materials were further purified by thin film chromatography using Hexanes, CH₃Cl and methanol mixed solvents as the eluent to afford a yellow solid. Yield: 1.0 g (32%). ¹H NMR (CDCl₃, 500.046 MHz): δ 8.84 (d, 2H, ³J=7.5 Hz, naphthalene-H), 8.38 (d, 2H, ³J=7.5 Hz, naphthalene-H), 4.19 (d, ³J=6.0 Hz, 2H, CH₂), 2.02 (m, 1H, CH), 1.5-1.2 (m, 4H, CH₂), 2.14 (m, 6H, Me); ¹³C NMR (125 MHz, CDCl₃): δ 186.2, 162.9, 143.8, 132.2, 126.7, 126.2, 122.9, 45.1, 36.6, 31.9, 31.6, 30.0, 29.7, 29.7, 29.6, 29.4, 29.3, 26.4, 22.7, 14.1; HRMS (m/z): [M]⁺ calcd. for C₃₈H₅₃NO₄, 587.83; found, 587.44.

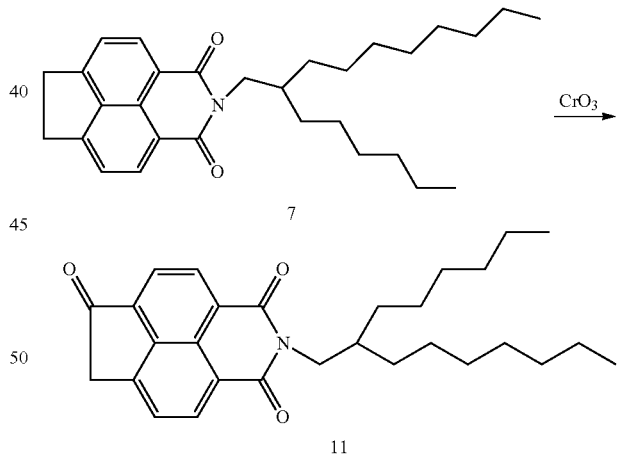

7

11

Compound 11. At 110° C., compound 7 (3.0 g, 5.36 mmole) was dissolved in 150 mL of acetic anhydride. After cooling back to room temperature, CrO₃ (1.6 g, 16.0 mmole) was added in portions. After stirring over night at room temperature, the dark green suspension was slowly poured onto 200 g of crushed ice. The crude material was extracted with CHCl₃, washed subsequently with water and brine. After removal of all the solvents, the solid materials were further purified by thin film chromatography using hexanes, CH₃Cl and methanol mixed solvents as the eluent to afford an orange solid. Yield: 0.27 g (8.7%). ¹H NMR (CDCl₃, 500.046 MHz): δ 8.71 (d, 1H, ³J=7.2 Hz, Np), 8.62 (d, 1H, $^3J$=7.2 Hz, Np), 8.17 (d, 1H, $^3J$=7.0 Hz, Np), 7.78 (d, 1H, $^3J$=7.0 Hz, Np), 4.16 (d, $^3J$=8.0 Hz, 2H, CH$_2$), 4.02 (s, 2H, CH$_2$), 2.03 (m, 1H, CH), 1.5-1.2 (m, 24H, CH$_2$), 0.87 (m, 6H, Me). HRMS (m/z): [M]$^-$ calcd. for C$_{29}$H$_{37}$NO$_3$, 447.28; found, 447.12.
Example 1B
Synthesis of Diketone Intermediates
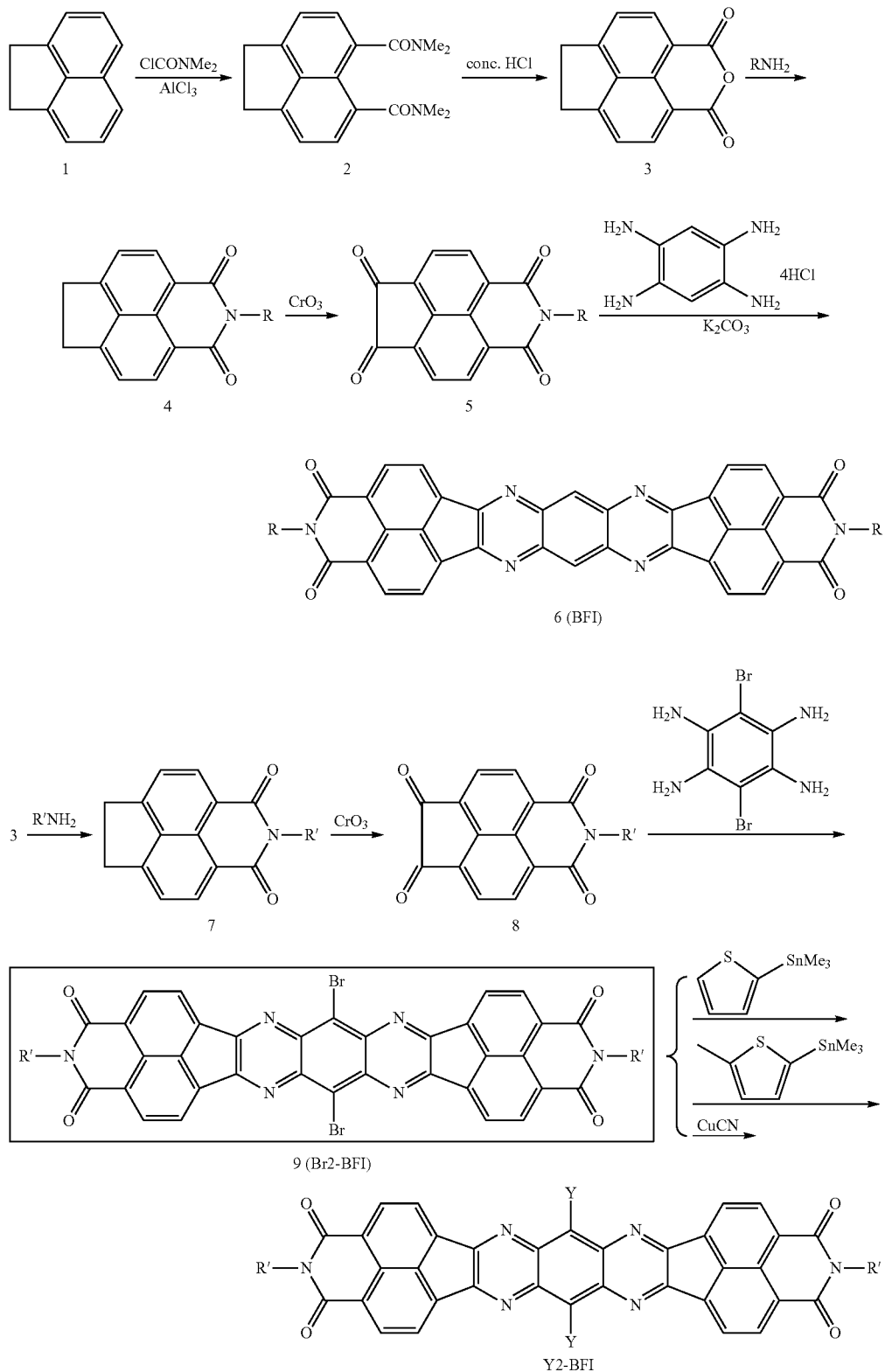

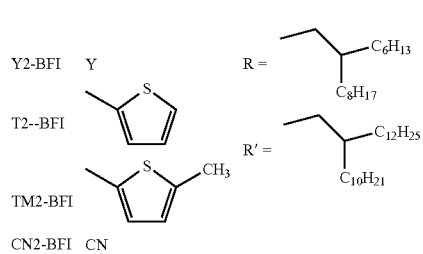

Synthesis of N5,N5,N6,N6-tetramethyl-1,2-dihydroacenaphthylene-5,6-dicarboxamide (Compound 2)

(Trost et al., *J. Am. Chem. Soc.* 1971, 93, (3), 737-745). Under $N_2$, 1,2-dihydroacenaphthylene (Compound 1, 12 g, 77.9 mmol) and dimethylcarbamoyl chloride (22 g, 206 mmol) were dissolved in 120 mL of chlorobenzene. The solution was then cooled to 0° C. followed by adding $AlCl_3$ (28 g, 209 mmol) portionwise. The mixture was slowly heated to 80° C. After stirring at 80° C. for 12 hours, the solution was cooled back to 0° C. and additional 14 g (130 mmol) of dimethylcarbamoyl chloride and 19 g (144 mmol) of $AlCl_3$ were added. The dark solution was refluxed for additional 12 hours. The solution was cooled to room temperature and poured into 800 mL of cold aqueous hydrochloric acid solution (5%). The organic phase was extracted with chloroform, washed subsequently with sodium bicarbonate solution and water, and dried over sodium sulfate. After removal of chloroform, crystals formed in 12 hs from chlorobenzene solution. Yield: 15.4 g (66.7%). $^1H$ NMR ($CDCl_3$, 500 MHz): δ=7.40 (d, 2H, $^3J$=7.0 Hz, Np), 7.33 (d, 2H, $^3J$=7.0 Hz, Np), 3.43 (s, 4H, $CH_2$), 3.11 (s, 6H, $CH_3$), 2.89 ppm (s, 6H, $CH_3$).

Synthesis of 1,2-dihydroacenaphthylene dicarboxylic acid anhydride (Compound 3)

Compound 2 (4.0 g, 13.5 mmol) was suspended in 10 mL of concentric hydrochloric acid. The mixture was heated to reflux for 4-5 hours. The solution was then cooled to 0° C. The off-white precipitate was collected by filtration and washed with cold water. The crude materials were recrystallized from hot acetic anhydride solution to afford pure product as needles. Yield (2.08 g, 68.7%). $^1H$ NMR ($CDCl_3$, 25° C., 500 MHz): δ=8.54 (d, 2H, $^3J$=7.0 Hz, Np), 7.65 (d, 2H, $^3J$=7.0 Hz, Np), 3.45 ppm (s, 4H, $CH_2$).

Synthesis of N-hexyldecyl-1,2-dihydroacenaphthylene dicarboxylic acid imide (Compound 4)

Under $N_2$, Compound 3 (1.2 g, 5.4 mmol) and 2-hexyldecan-1-amine (1.5 g, 6.2 mmol) were dissolved in 15 mL of DMF. The solution was slowly heated to 90° C. for 12 hours and to 110° C. for additional 12 hours. After cooling back to room temperature, water was added to quench the reaction. The organic phase was extracted with chloroform, washed subsequently with water and brine, dried over sodium sulfate. After removal of the solvents, the crude materials were further purified by column chromatography with hexanes: chloroform (2:1 v/v) as the eluent. Yield (1.56, 65.1%). $^1H$ NMR ($CDCl_3$, 25° C., 500 MHz): δ=8.51 (d, 2H, $^3J$=7.0 Hz, Np), 7.58 (d, 2H, $^3J$=7.0 Hz, Np), 4.14 (d, 2H, $^3J$=7.0 Hz, $CH_2$), 3.59 (s, 4H, $CH_2$), 2.01 (m, 1H, CH), 1.5-1.2 (m, 24H, $CH_2$), 0.87 ppm (m, 6H, $CH_3$). HRMS (m/z): $[M]^+$ calcd. for $C_{30}H_{41}NO_2$, 447.65; found, 448.35.

Synthesis of Compound 5

At 110° C., compound 4 (1.0 g, 2.2 mmol) was dissolved in 100 mL of acetic anhydride. After cooling back to room temperature, $CrO_3$ (600 mg, 6.1 mmol) was added in portions. The solution was slowly warmed up to 50-80° C. and kept stirring for 4 hours. The dark green suspension was slowly poured onto 100 g of crushed ice. The crude material was extracted with $CHCl_3$, washed subsequently with water and brine. After removal of all the solvents, the solid materials were further purified by thin film chromatography using hexanes: $CHCl_3$ (3:2 v/v) with a few drops of methanol as the eluent to afford a yellow solid. Yield: 210 mg (19.8%). $^1H$ NMR ($CDCl_3$, 25° C., 500 MHz): δ 8.83 (d, 2H, $^3J$=7.5 Hz, Np), 8.37 (d, 2H, $^3J$=7.5 Hz, Np), 4.20 (d, $^3J$=6.0 Hz, 2H, $CH_2$), 2.10 (m, 1H, CH), 1.5-1.2 (m, 24H, $CH_2$), 2.14 ppm (m, 6H, Me); HRMS (m/z): $[M]^+$ calcd. for $C_{30}H_{37}NO_4$, 475.62; found, 475.12.

Synthesis of N-decyltetradecyl-1,2-dihydroacenaphthylene dicarboxylic acid imide (Compound 7)

Under $N_2$, compound 3 (1.2 g, 5.4 mmol) and 2-decyltetradecyl-1-amine (2.2 g, 6.2 mmol) were dissolved in 25 mL of DMF. The solution was slowly heated to 90° C. for 12 hours and to 110° C. for additional 12 hours. After cooling back to room temperature, water was added to quench the reaction. The organic phase was extracted with chloroform, washed subsequently with water and brine, dried over sodium sulfate. After removal of the solvents, the crude materials were further purified by column chromatography with hexanes: chloroform (2:1 v/v) as the eluent Yield (2.4 g, 80.0%). $^1H$ NMR ($CDCl_3$, 25° C., 500 MHz): δ=8.51 (d, 2H, $^3J$=7.0 Hz, Np), 7.58 (d, 2H, $^3J$=7.0 Hz, Np), 4.14 (d, 2H, $^3J$=7.0 Hz, $CH_2$), 3.59 (s, 4H, $CH_2$), 2.01 (m, 1H, CH), 1.5-1.2 (m, 40H, $CH_2$), 0.87 ppm (m, 6H, $CH_3$). HRMS (m/z): $[M]^+$ calcd. for $C_{38}H_{57}NO_2$, 559.86; found, 560.46.

Synthesis of Compound 8

At 110° C., compound 7 (3.0 g, 5.4 mmol) was dissolved in 150 mL of acetic anhydride. After cooling back to room temperature, $CrO_3$ (1.6 g, 16.0 mmol) was added in portions.

The solution was slowly warmed up to 50-80° C. and kept stirring for 4 hours. The dark green suspension was slowly poured onto 200 g of crushed ice. The crude material was extracted with CHCl$_3$, washed subsequently with water and brine. After removal of all the solvents, the solid materials were further purified by thin film chromatography using hexanes: CHCl$_3$ (3:2 v/v) with a few drops of methanol as the eluent to afford a yellow solid. Yield: 1.0 g (31.7%). $^1$H NMR (CDCl$_3$, 25° C., 500 MHz): δ=8.84 (d, 2H, $^3$J=7.5 Hz, Np), 8.38 (d, 2H, $^3$J=7.5 Hz, Np), 4.19 (d, $^3$J=6.0 Hz, 2H, CH$_2$), 2.02 (m, 1H, CH), 1.5-1.2 (m, 40H, CH$_2$), 2.14 ppm (m, 6H, Me); $^{13}$C NMR (125 MHz, CDCl$_3$): δ 186.2, 162.9, 143.8, 132.2, 126.7, 126.2, 122.9, 45.1, 36.6, 31.9, 31.6, 30.0, 29.7, 29.7, 29.6, 29.4, 29.3, 26.4, 22.7, 14.1; HRMS (m/z): [M]$^+$ calcd. for C$_{38}$H$_{53}$NO$_4$, 587.83; found, 587.44.

Part II

Example 2A

Synthesis of Compound/Monomer Br2-BFI

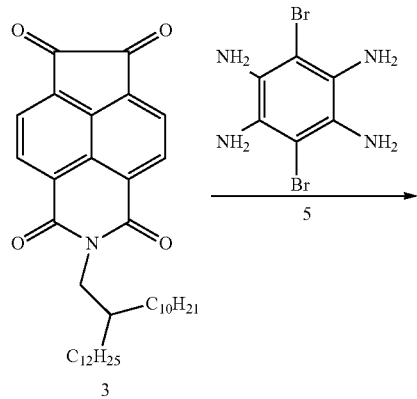

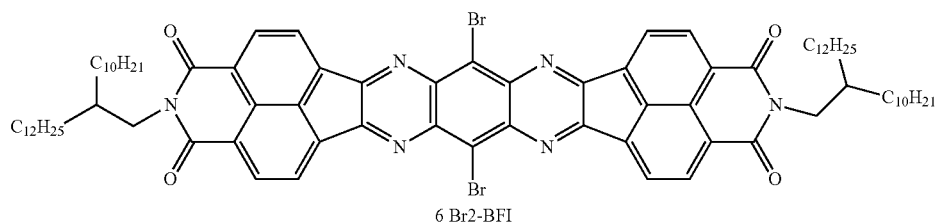
6 Br2-BFI

Compound 6. 3,6-dibromobenzene-1,2,4,5-tetraamine (Compound 5) was prepared according to the reported procedure (Hong, D.-J. et al. Chem. Commun. 2010, 46, (27), 4896). Compound 5 (0.23 g, 0.77 mmole) was dissolved in 15 mL of chlorobenzene followed by adding 1.0 g of compound 3 (1.7 mmole). The mixture was slowly heated to 100° C. and kept stirred for 24 hours. After cooling back to room temperature, the volatile materials were removed under high vacuum. The solid materials left were further purified through preparative thin film chromatography. The product was isolated as an orange red solid. Yield: 0.65 g, 54.6%. $^1$H NMR (CDCl$_3$, 500.046 MHz): δ 8.50 (d, $^3$J=7.0 Hz, 4H, NP), 8.39 (d, $^3$J=7.5 Hz, NP, 4H), 3.91 (d, J=6.5 Hz, 4H, CH$_2$), 1.88 (m, 2H, CH), 1.4-1.2 (m, 40H, CH$_2$), 0.90 (m, 12H, CH$_3$); $^{13}$C NMR (125 MHz, CDCl$_3$): δ 162.9, 155.1, 138.6 136.4, 134.6, 132.5, 129.2, 125.0, 124.9, 124.0, 123.9, 44.8, 34.0, 32.2 (2C), 31.8, 30.3, 30.0, 29.9 9 (2C), 29.6, 26.6, 22.9, 14.4; HRMS (m/z): [M]$^+$ calcd. for C$_{82}$H$_{106}$Br$_2$N$_6$O$_4$, 1399.56; found, 1399.55.

Example 2B

Synthesis of Compound/Monomer Br2-BFI

Compound 8 (1.0 g, 1.7 mmol) was added to 3,6-dibromobenzene-1,2,4,5-tetraamine (0.77 mmol) in acetic acid prepared according to the reported procedure (E. Wang, et al, Org. Lett. 2010, 12, 4470.) The mixture was slowly heated to 100° C. and kept stirred for 24-48 hours. After cooling back to room temperature, the volatile materials were removed under high vacuum. The solid materials left were further purified through preparative thin film chromatography with CHCl$_3$: methanol (50:1 v/v) as the eluent (Rf=0.24). The product was isolated as an orange red solid. Yield: 0.65 g, 54.6%. $^1$H NMR (CDCl$_3$, 25° C., 500 MHz): δ=8.46 (d, 4H, $^3$J=7.0 Hz, Np), 8.35 (d, 4H, $^3$J=7.0 Hz, Np), 3.87 (d, 4H, J=7.0 Hz, CH$_2$), 1.82 (m, 2H, CH), 1.4-1.2 (m, 80H, CH$_2$), 0.86 ppm (m, 12H, CH$_3$); $^{13}$C NMR (125 MHz, CDCl$_3$): δ=162.9, 155.1, 138.6 136.4, 134.6, 132.5, 129.2, 125.0, 124.9, 123.9, 44.8, 34.0, 32.2 (2C), 31.8, 30.3, 30.0, 29.9 9 (2C), 29.6, 26.6, 22.9, 14.4 ppm; HRMS (m/z): [M]$^+$ calcd. for C$_{82}$H$_{106}$Br$_2$N$_6$O$_4$, 1399.56; found, 1399.55; elemental analysis calcd for C$_{82}$H$_{106}$Br$_2$N$_6$O$_4$: C, 70.37%; H, 7.63%; N, 6.00%. found C, 70.35%; H, 7.58%; N, 6.14%.

Example 3A

Synthesis and Characteristics of Compound BFI

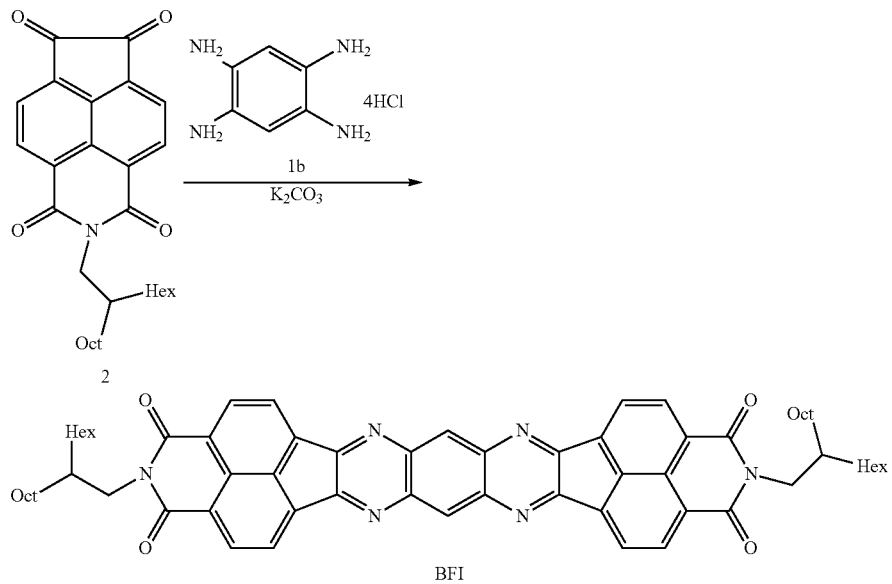

1,2,4,5-benzenetetraamine tetrahydrochloride (compound 1b) was purchased from Aldrich and used as received. Inside a reaction tube, compound 2 (100 mg, 0.21 mmole), 1,2,4,5-benzenetetraamine tetrahydrochloride (compound 1b, 27 mg, 0.095 mmole) and $K_2CO_3$ (26 mg, 0.19 mmole) were suspended in 15 mL of ethanol. The mixture was slowly warmed up to 78° C. and a yellow precipitate formed within 2 hours. The suspension was kept stirring over night to 48 hours at the same temperature. After cooling back to room temperature, the solid was collected by filtration and followed by washing with 3×10 mL of ethanol and 3×10 mL of $CHCl_3$. The crude product was further purified by crystallization from hot chlorobenzene solution. Yield: 69 mg (71%). $^1$H NMR ($CDCl_3$, 500 MHz): δ=8.94 (s, 2H, Ph), 8.70 (d, 2H, 3J=7.0 Hz, Nh), 8.52 (d, 2H, $^3$J=7.5 Hz, Nh), 4.17 (d, 4H, $^3$J=7.5 Hz, CH2), 2.02 (m, 1H, CH), 1.4-1.2 (m, 24H, $CH_2$), 0.9 (m, 6H, Me).

BFI exhibited an intense absorption band with an absorption maximum at $\lambda_{max}$=395 nm in a dilute chlorobenzene solution, which was slightly blue shifted (15 nm) as thin film on the glass substrate. The optical band gap estimated from the absorption edge was 2.46 eV. When excited at 395 nm, BFI emitted bright yellow green lights with three bands at $\lambda_{max}$=483 nm, 516 nm and 552 nm, respectively.

The electron affinity of BFI was evaluated by cyclic voltammetry. BFI showed two quasi-reversible reduction waves at $E_{1/2}$=−1.08 V and −1.2 V vs SCE, respectively. No apparent oxidation was observed during an anodic scan in the range up to 1.2 V vs. SCE. Based on the onsets of reduction waves, the LUMO energy level of BFI was estimated to be −3.60 eV.

The BFI molecules were readily self-assembled into single crystalline 1D nanostructures. The nanowires (NWs) of BFI were also grown from hot chlorobenzene solution (0.5 mg/mL). The solution was heated to reflux and slowly cooled to room temperature without disturbing it. FIGS. 1A and 1B show the transmission electron microscopy (TEM) and selected area electron diffraction (SAED) images (inset) of BFI. The sharp spots in the SAED pattern indicates that the NWs formed through the solution phase method are single-crystalline. The nanocrystals can be prepared in large quantity and high density as shown in the scanning electron microscopy (SEM) images (FIGS. 1C and 1D) suggesting that these NWs are suitable for fabricating solution processed organic NW electronics. According to single crystal x-ray diffraction, BFI has a fairly planar backbone. The BFI molecules adopt a slipped π-π stacking with a close intermolecular distance of 3.26 Å between the neighboring molecules. Between the BFI stacks, the BFI molecules are assembled by strong hydrogen bonding. In these hydrogen bonds, the oxygen on the carbonyl group and the ortho-carbon on the naphthalene ring of the neighboring molecule function as the hydrogen acceptor (A) and donor (D), respectively. The H . . . O distance is measured to be 2.44 Å and the C—H . . . O angle to be 140.1°. The strong π-π stacking and hydrogen bonding are beneficial to the high crystallinity and high charge carrier mobility.

BFI showed excellent thermal properties. Thermal gravimetric analysis (TGA) shows that BFI was thermally stabile up to 400° C. No apparent thermal transition was observed for BFI based on differential scanning calorimetry (DSC) scans in the temperature range of 30 to 300° C. BFI's excellent thermal stability is highly advantageous for applications in durable and robust organic electronics.

Example 3B

Synthesis and Characteristics of Compound BFI

Inside a reaction tube, compound 5 (100 mg, 0.21 mmol), 1,2,4,5-benzenetetraamine tetrahydrochloride (27 mg, 0.095 mmol, bought from Sigma-Aldrich and used as received) and $K_2CO_3$ (26 mg, 0.19 mmol) were suspended in 15 mL of ethanol. The mixture was slowly warmed up to 78° C. and a yellow precipitate formed within 2 hours. The suspension was kept stirring over night at the same temperature. After cooling back to room temperature, the solid was collected by filtration and followed by washing with 3×10 mL of ethanol and 3×10 mL of CHCl₃. The crude product was further purified by crystallization from hot solution in chlorobenzene. Yield: 69 mg (60.3%). $^1$H NMR (CDCl₃, 25° C., 500 MHz): δ=9.19 (s, 2H, Ph), 8.72 (d, 4H, $^3J$=7.0 Hz, Np), 8.56 (d, 4H, $^3J$=7.0 Hz, Np), 4.15 (d, 4H, $^3J$=7.5 Hz, CH₂), 1.96 (m, 2H, CH), 1.4-1.2 (m, 48H, CH₂), 0.85 ppm (m, 12H, Me). $^{13}$C NMR (125 MHz, 25° C., CDCl₃/CF₃COOD): δ 163.9, 155.4, 139.4 136.8, 129.6, 125.2, 125.1, 124.8, 45.6, 37.1, 32.2, 32.1, 31.9, 30.3, 30.0, 29.8, 29.6, 26.7, 26.6, 22.9, 14.3 ppm (2C); HRMS (m/z): [M]⁻ calcd. for C₆₆H₇₆N₆O₄, 1017.35; found, 1017.46.

Example 4

Transistors Based on Compound BFI

Field-effect transistors were fabricated on a heavily n-doped silicon substrate with thermally grown silicon dioxide gate insulator (200 nm; capacitance density, $C_i$=17 nF/cm²). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). BFI was deposited from a solution in trifluoroacetic acid (TFA) with 1-5 vol % of methanesulfonic acid (MSA) or in hot 1,2-dichlorobenzene. The films were immersed in methanol to remove trace of acid solvents and dried overnight under vacuum at room temperature. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(μWCo/2L)(Vg−Vt)2. (Kang, S.-M.; Leblebici, Y. *CMOS Digital Integrated Circuits: Analysis and Design*, McGraw-Hill, New York, 1996.) The electron mobility of 0.046 cm² V⁻¹ s⁻¹ was obtained, with an on/off current ratio of 10⁶. The transistor characteristic curves of an n-channel field-effect transistor based on BFI are shown in FIG. 3.

Example 5

Synthesis and Characteristics of Compound BFI5N

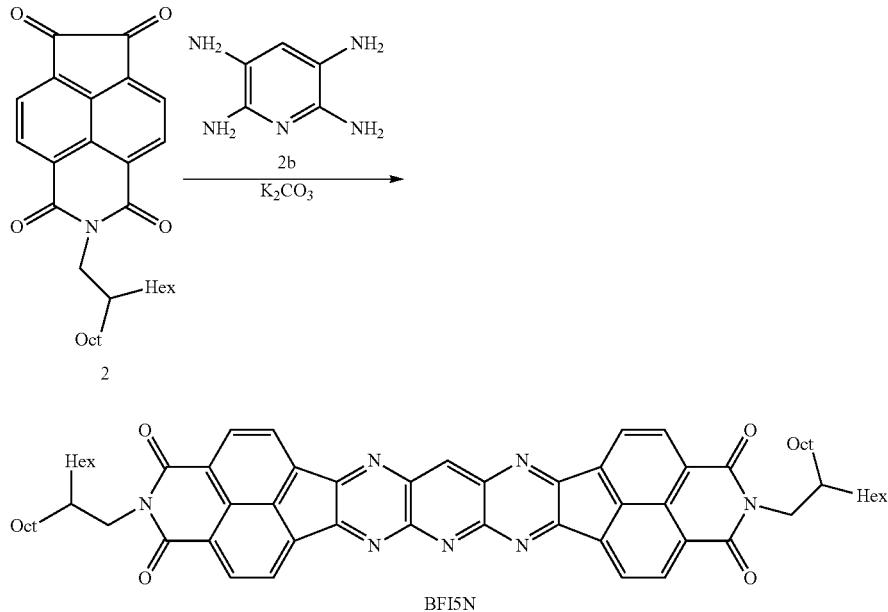

2,3,5,6-tetraaminopyridine (compound 2b) was synthesized according to reported procedures (CN101531632A, example 1). Inside a reaction tube, compound 2 (100 mg, 0.21 mmole) and 2b (26 mg, 0.19 mmole) were suspended in 5 mL of ethanol. The mixture was slowly warmed up to 78° C. Compound 2b (12.3 mg, 0.09 mmole) was added in three portions. The yellow suspension was kept stirring over night at the same temperature. After cooling back to room temperature, the solid was collected by filtration and followed by washing with 3×10 mL of ethanol and 3×10 mL of CHCl₃. The crude product was further purified by crystallization from hot solution in chlorobenzene. Yield: 58 mg (54%). 1H NMR (CDCl₃/CF₃COOD, 500 MHz): δ=10.25 (s, 1H, py), 9.00 (dd, 4H, Nh), 8.92 (d, 2H, 3J=7.5 Hz, Nh), 8.74 (d, 2H, 3J=7.0 Hz, Nh), 4.27 (d, 4H, 3J=7.5 Hz, CH2), 2.04 (m, 1H, CH), 1.4-1.2 (m, 24H, CH2), 0.9 (m, 6H, Me); 13C NMR (CF3COOD, 125.7 MHz): 167.9, 167.8, 166.1, 161.4, 152.3, 147.6, 141.2, 138.0, 136.9, 136.6, 136.0, 135.8, 129.7, 129.1, 128.5, 127.8, 127.7, 48.7, 39.2, 33.8, 33.7, 33.6, 31.8, 31.5, 31.4, 31.2, 28.4, 24.4, 24.4, 14.7, 14.7.

BFI5N exhibited an intense absorption with an absorption maximum (λmax) at 395 nm in a dilute chlorobenzene solution, which was slightly blue shifted (15 nm) as thin film on the glass substrate. The optical band gap estimated from the absorption edge was 2.46 eV. Unlike highly emissive BFI, BFI5N was completely non-luminescent both in dilute solution and as thin film.

The electron affinity of BFI5N was characterized by cyclic voltammetry. BFI5N showed an unresolved irreversible reduction wave at $E_{1/2}$=−1.25 V vs. SCE. No apparent oxidation was observed during an anodic scan in the range up to 1.2 V vs. SCE. The LUMO energy level of BFI5N calculated from the reduction onset was −3.45 eV.

BFI5N showed excellent thermal properties. Thermal gravimetric analysis (TGA) shows that BFI5N was thermally stabile up to 403° C. No apparent thermal transition was observed for BFI5N based on differential scanning calorimetry (DSC) scans in the temperature range of 20 to 300° C. The excellent thermal stability of BFI5N is highly advantageous for durable and robust organic electronics.

Example 6

Transistors Based on Compound BFI5N

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). BFI5N was deposited from a solution in trifluoroacetic acid (TFA) with 1-5 vol % of methanesulfonic acid (MSA) or in hot 1,2-dichlorobenzene. The films were immersed in methanol to remove trace of acid solvents and dried overnight under vacuum at room temperature. The devices were annealed at various temperatures under argon environment. Electrical characteristics of the devices were measured using an HP4145B semiconductor parameter analyzer under nitrogen atmosphere.

Figure 3A:
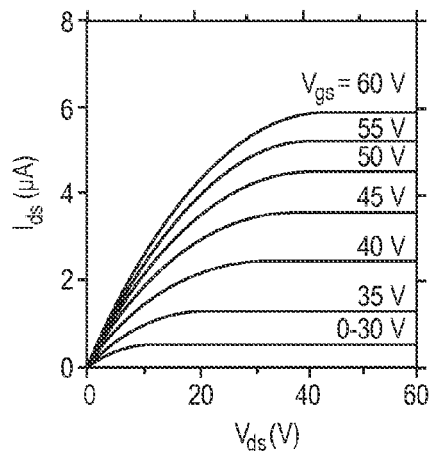
FIG. 3 (A, B) Current-voltage output and transfer curves of the PBFI-T transistors with silver source-drain electrodes on an OTS8-treated substrate after annealing for 10 min at 200° C. A field-effect electron mobility of 03 cm$^2$/Vs was observed in saturation region. (C, D) Output curve family and transfer curves of PBFI-BT transistors with gold electrodes on a BCB-treated substrate after annealing for 10 min at 200° C.
Figure 3B:
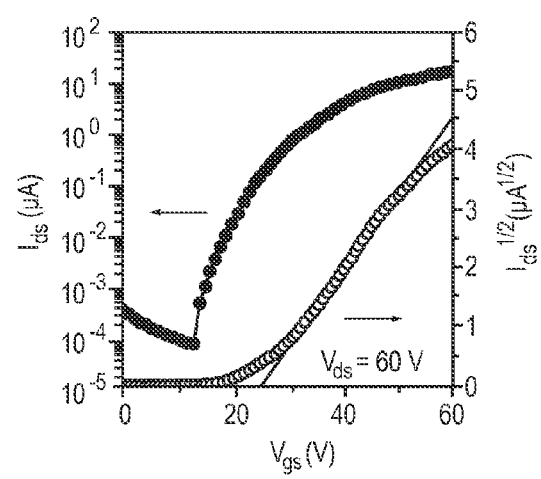
Figure 3C:
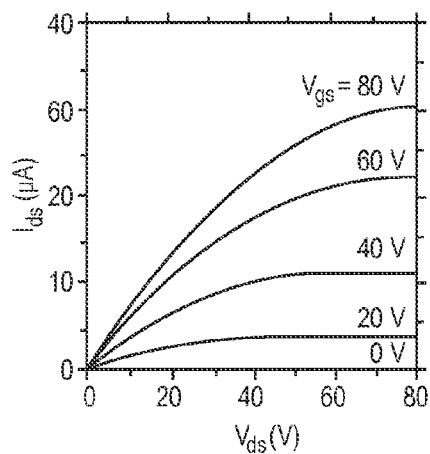
Figure 3D:
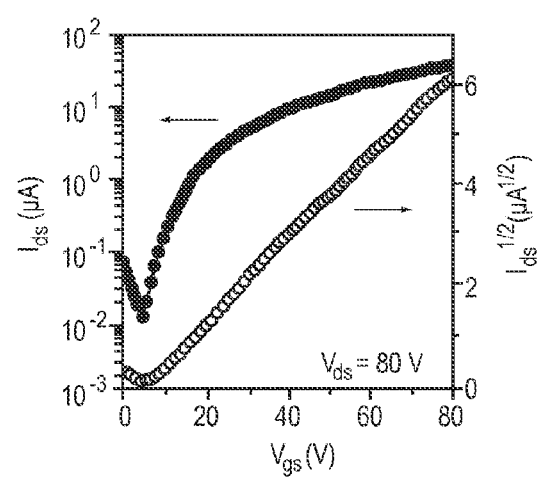

The charge carrier mobilities were calculated from transfer curves using the standard saturation equation of metal-oxide-semiconductor field-effect transistors: Ids=(μWCo/2 L)(Vg−Vt)2. (Kang, S.-M.; Leblebici, Y. *CMOS Digital Integrated Circuits: Analysis and Design*, McGraw-Hill, New York, 1996.) The electron mobility of 0.010 cm$^2$ V$^{-1}$ s$^{-1}$ was obtained for transistors based on BFI5N (FIG. 3b).

Example 7

Synthesis and Characteristics of Compound BFI2N

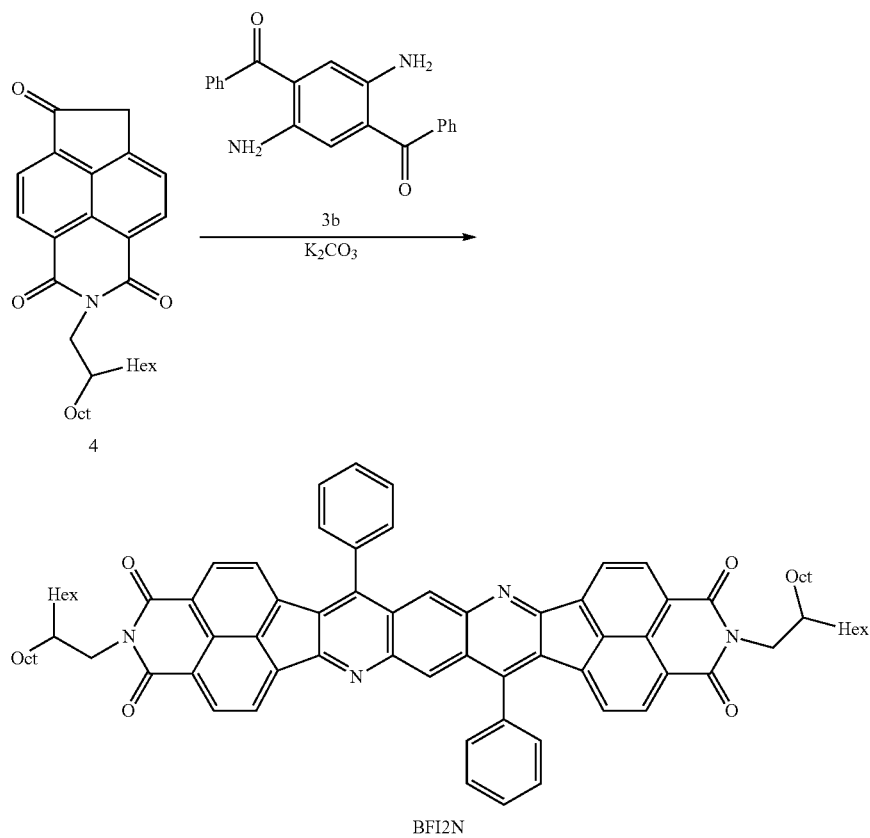

Compound 3b was synthesized according to reported procedure (Liu, S. et al. *Dyes and Pigments*, 81, 2009, 218-223). Inside a reaction tube, compound 4 (100 mg, 0.22 mmole) and diphenyl phosphate (433 mg, 1.74 mmole) and (2,5-diamino-1,4-phenylene)bis(phenylmethanone) (compound 3b, 34 mg, 0.11 mmole) were mixed with 3 mL of toluene. The mixture was slowly warmed up to 110° C. and kept stirring over night. After cooling back to room temperature, the dark red solution was precipitated into 80 mL of methanol and triethylamine mixed solvents (1:1). A red solid formed which was collected and washed with 3×20 mL of methanol. The solid was further purified by column chromatography with CHCl3 as the eluent solvent. Yield: 63 mg (65%). $^1$H NMR (CDCl3, 300.xxx MHz): δ=8.27 (m, 4H), 7.95-7.75 (m, 12H), 7.50 (br, 2H), 6.98 (d, 2H, 3J=7.5 Hz), 4.09 (d, 4H, 3J=7.2 Hz, CH2), 1.90 (m, 2H, CH), 1.4-1.1 (m, 48H, CH2), 0.83 (t, 12H, Me); $^{13}$C NMR (CF3COOD, 125.7 MHz): 163.4, 163.2, 159.8, 144.1, 143.8, 138.4, 138.2, 134.7, 134.2, 132.4, 130.9, 129.9, 129.7, 129.3, 129.1, 128.5, 127.7, 124.6, 123.1, 122.8, 122.1, 120.8, 44.7, 36.9, 32.1, 32.1, 32.0, 31.9, 30.3, 30.0 29.8, 29.6, 26.8, 26.7, 22.9, 14.3.

BFI2N exhibited an intense absorption with an absorption maximum ($\lambda_{max}$) at 395 nm with two relatively weak low-energy absorption bands in a dilute chlorobenzene solution, which became less structured as thin film on the glass substrate. The optical band gap estimated from the absorption edge was 2.20 eV. BFI2N was highly emissive in dilute solution with three emission band at $\lambda_{max}$=615 nm, 558 nm, 520 nm. BFI2N thin film showed a broad structureless red emission centered at $\lambda_{max}$=600 nm.

The electron affinity of BFI2N was characterized by cyclic voltammetry. BFI2N showed an unresolved irreversible reduction wave at $E_{1/2}$=−1.20 V vs. SCE. No apparent oxidation was observed during an anodic scan in the range up to 1.2 V vs. SCE. The LUMO energy level of BFI2N calculated from the reduction onset was −3.55 eV.

BFI2N showed excellent thermal properties. Thermal gravimetric analysis (TGA) shows that BFI2N was thermally stabile up to 446° C. No apparent thermal transition was observed for BFI2N based on differential scanning calorimetry (DSC) scans in the temperature range of 20 to 300° C. The excellent thermal stability of BFI2N is highly advantageous for durable and robust organic electronics.

Example 8

Transistors Based on Compound BFI2N

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). BFI2N was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(μWCo/2 L)(Vg−Vt)$^2$. (Kang, S.-M.; Leblebici, Y. *CMOS Digital Integrated Circuits: Analysis and Design*, McGraw-Hill, New York, 1996.) The electron mobility of 1.4×10$^{-4}$ cm$^2$ V$^{-1}$ s$^{-1}$ was obtained for transistors based on BFI2N (FIG. 3b).

Example 9A

Synthesis and Characteristics of Compound T2-BFI

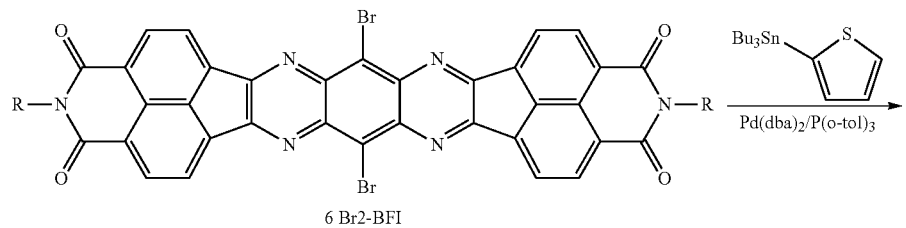

6 Br2-BFI

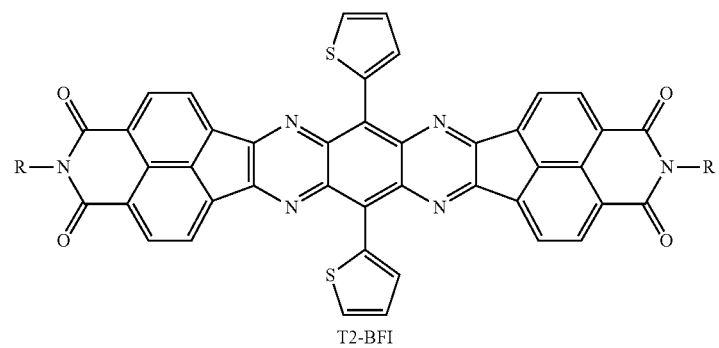

T2-BFI

R = 2-decyltetradecyl

Under protection of argon, compound 6 (200 mg, 0.14 mmole), tributylstannannylthiophene (128 mg, 0.34 mmole), Pd(dba)$_2$ (3 mg) and P(°tol)$_3$ (6 mg) were charged into a reaction tube and dissolved in 10 mL of degassed toluene. The solution was slowly warmed up to 110° C. and kept stirring for 2 days. After cooling back to room temperature, the volatile materials were removed under high vacuum. The solids left were further purified through column chromatography with chloroform and methanol as the eluent solvents. The pure product was isolated as a blue solid. Yield: 135 mg, 67%. $^1$H NMR (CDCl3, 500 MHz): δ=8.43 (d, $^3$J=7.0 Hz, 4H, Np), 8.28 (dd, 2H, Th), 8.12 (d, $^3$J=7.0 Hz, 4H, Np), 7.82 (dd, 2H, Th), 7.36 (q, 2H, Th), 3.77 (d, 4H, CH$_2$), 1.83 (m, 1H, CH), 1.4-1.2 (m, 80H, CH$_2$). 0.83 (m, 12H, Me); $^{13}$C NMR (CDCl$_3$, 500 MHz): 163.1, 152.7, 136.8, 136.2, 135.7, 135.6, 133.7, 132.5, 131.7, 131.1, 126.4, 125.0, 124.3, 123.2, 44.6, 37.0, 32.2, 31.8, 30.3, 29.9, 26.7, 22.9.

T2-BFI exhibited two absorption bands in dilute chloroform solution, one intense absorption with an absorption maximum ($\lambda_{max}$) at 410 nm which is due to the π-π* transition of the traazabenzodifluoranthene diimide moiety, and a weak low energy absorption at $\pi_{max}$=550 nm which mainly arises from charge transfer from the central electron donating dithienylbenzene moiety to the naphthalene imide group. The low energy band was red-shifted and relatively more intense going from dilute solution to thin film due to more efficient charge transfer and stronger intermolecular interaction in the solid state. The optical band gap estimated from the absorption edge was 1.55 eV.

The electron affinity of T2-BFI was characterized by cyclic voltammetry. T2-BFI showed a two quasi-reversible reduction wave at $E_{1/2}$=−1.10 V and −1.35 V vs. SCE, respectively. No apparent oxidation was observed during an anodic scan in the range up to 1.3 V vs. SCE. The LUMO energy level of T2-BFI calculated from the reduction onset was −3.70 eV.

T2-BFI showed excellent thermal properties. Thermal gravimetric analysis (TGA) shows that T2-BFI was thermally stabile up to 400° C. No apparent thermal transition was observed for T2-BFI based on differential scanning calorimetry (DSC) scans in the temperature range of 30 to 300° C. The excellent thermal stability of T2-BFI is highly advantageous for applications in durable and robust organic electronics.

Example 9B

Synthesis and Characteristics of Compound T2-BFI

Under protection of argon, Br2-BFI (200 mg, 0.14 mmol), tributylstannannylthiophene (128 mg, 0.34 mmol), Pd(dba)$_2$ (3 mg) and P(o-tol)$_3$ (6 mg) were charged into a reaction tube and dissolved in 10 mL of degassed toluene. The solution was slowly warmed up to 110° C. and kept stirring for 2 days. After cooling back to room temperature, the volatile materials were removed under high vacuum. The solids left were further purified through column chromatography with chloroform and methanol (200:1 v/v) as the eluent solvents (Rf=0.28). The pure product was isolated as a blue solid. Yield: 135 mg, 67%. $^1$H NMR (CDCl$_3$, 25° C., 500 MHz): δ=8.43 (d, 4H, $^3$J=7.0 Hz, Np), 8.28 (d, 2H, $^3$J=3.5 Hz, Th), 8.12 (d, 4H, $^3$J=7.0 Hz, Np), 7.83 (d, 2H, $^3$J=5.0 Hz, Th), 7.36 (q, 2H, Th), 3.77 (d, 4H, $^3$J=4.0 Hz, CH$_2$), 1.83 (m, 2H, CH), 1.4-1.2 (m, 80H, CH$_2$). 0.83 ppm (m, 12H, Me); $^{13}$C NMR (CDCl$_3$, 25° C., 500 MHz): 163.1, 152.7, 136.8, 136.2, 135.7, 135.6, 133.7, 132.5, 131.7, 131.1, 126.4, 125.0, 124.3, 123.2, 44.6, 37.0, 32.2, 31.8, 30.3, 29.9, 26.7, 22.9, 14.4 ppm; HRMS (m/z): [M]$^+$ calcd. for C$_{90}$H$_{112}$N$_6$O$_4$S$_2$, 1406.02; found, 1405.71; elemental analysis calcd for C$_{90}$H$_{112}$N$_6$O$_4$S$_2$: C, 76.88%; H, 8.03%; N, 5.98%. found C, 76.70%; H, 7.99%; N, 5.97%.

Example 10

Transistors Based on Compound T2-BFI

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). T2-BFI was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(μWCo/2 L)(Vg−Vt)2. (Kang, S.-M.; Leblebici, Y. *CMOS Digital Integrated Circuits: Analysis and Design*, McGraw-Hill, New York, 1996.) The electron mobility of 0.12 cm$^2$ V$^{-1}$ s$^{-1}$ was obtained for transistors based on T2-BFI (*Angew. Chem. Int. Ed.* 2013, 52, 5513-5517).

Example 11

Solar Cells based on T2-BFI

Solar cells with device structure of ITO/PEDOT:PSS/active layer/LiF/Al were fabricated. ITO substrates (10Ω/□, Shanghai B. Tree Tech. Consult Co., Ltd, Shanghai, China) were cleaned sequentially with acetone, deionized water and isopropyl alcohol in an ultrasonic bath, and blown with nitrogen until dried. A 40 nm PEDOT:PSS (Clevios P VP AI 4083) layer was spin-coated on top of the ITO and dried at 150° C. for 10 min under vacuum. The active layer was then spin-coated from poly[(4,4'-bis(3-(2-ethyl-hexyl)dithieno[3,2-b:2',3'-d]silole)-2,6-diyl-alt-(2,5-bis(3-(2-ethyl-hexyl) thiophen-2yl)thiazolo[5,4-d]thiazole)] (PSEHTT):T2-BFI (1:4 wt/wt) blend solution to make a thin film of ~90 nm thickness and thermally annealed at 150° C. for 10 min in a glovebox. The substrates were then loaded in a thermal evaporator (BOC Edwards, 306) to deposit a cathode composed of 1.0 nm LiF and 90 nm Al under high vacuum (8×10$^{-7}$ Torr). Five solar cells, each with an active area of 4 mm$^2$, were fabricated per ITO substrate. PSEHTT was synthesized according to CN102782011A, EP2493960A1, US20120273732, and Subramaniyan et al., *Adv. Energy Mater.* 2011, 1, 854-860.

Figure 7A:
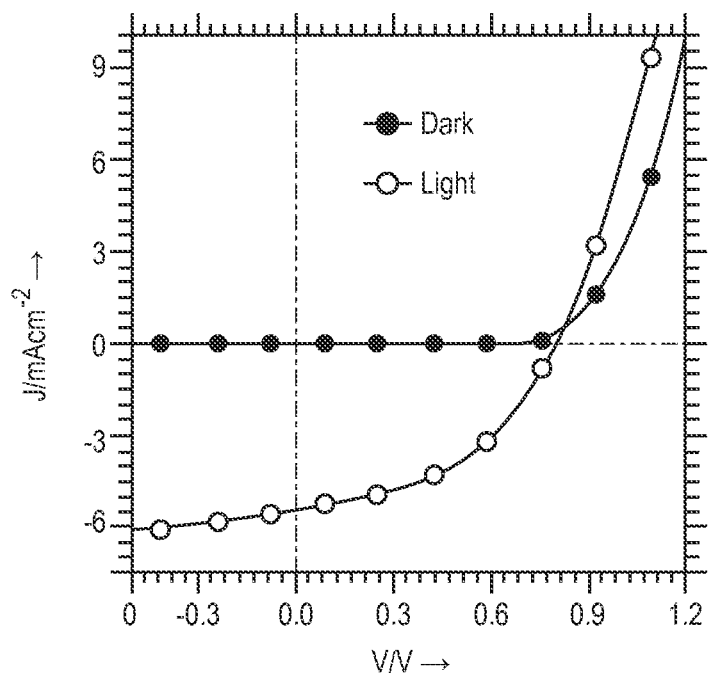
FIG. 7 shows: a) J-V characteristics of PSEHTT:T2-BFI (1:4 wt/wt) blend solar cell and b) the corresponding EQE spectrum.
Figure 7B:
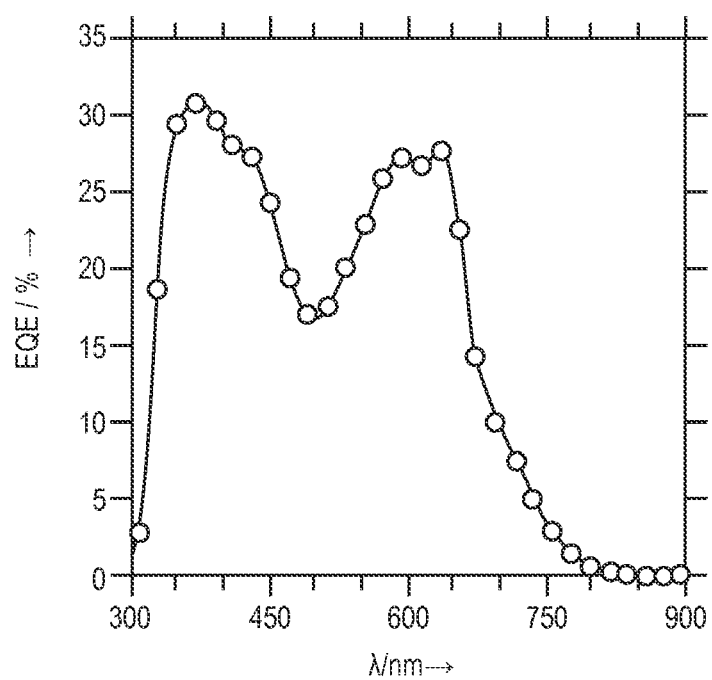

The current density-voltage (J-V, shown in FIG. 7a) curves of solar cells were measured using a HP4155A semiconductor parameter analyzer under laboratory ambient air conditions. An AM1.5 illumination at 100 mW/cm$^2$ was provided by a filtered Xe lamp and calibrated by using an NREL-calibrated Si diode. The external quantum efficiency (EQE, shown in FIG. 7b) was measured using a QEX10 solar cell quantum efficiency measurement system (PV Measurements, Inc.) and was calibrated with a NREL-certified Si diode before measurement. The resulting photovoltaic parameters include an open circuit voltage ($V_{oc}$) of 0.79 V, a short-circuit current density ($J_{sc}$) of 5.14 mAcm$^{-2}$, and a fill factor (FF) of 0.44. A maximum power conversion efficiency of 1.80% (average of 1.74±0.06%) was achieved (*Angew. Chem. Int. Ed.* 2013, 52, 5513-5517).

Example 12A

Synthesis and Characteristics of Compound TM2-BFI

T2-BFI due to the electron donating effect of the methyl groups. As a thin film, the low energy absorption, which was relatively more intense than in solution, was strongly red shifted. The optical band gap estimated from the absorption edge was 1.60 eV.

The electron affinity of TM2-BFI was characterized by cyclic voltammetry. TM2-BFI showed an unresolved quasi-reversible reduction wave at $E_{1/2}=-1.25$ V vs. SCE. No apparent oxidation was observed during an anodic scan in the range up to 1.2 V vs. SCE. The LUMO energy level of TM2-BFI calculated from the reduction onset was −3.59 eV.

TM2-BFI showed excellent thermal properties. Thermal gravimetric analysis (TGA) shows that TM2-BFI was thermally stabile up to 400° C. No apparent thermal transition was observed for TM2-BFI based on differential scanning calorimetry (DSC) scans in the temperature range of 20 to

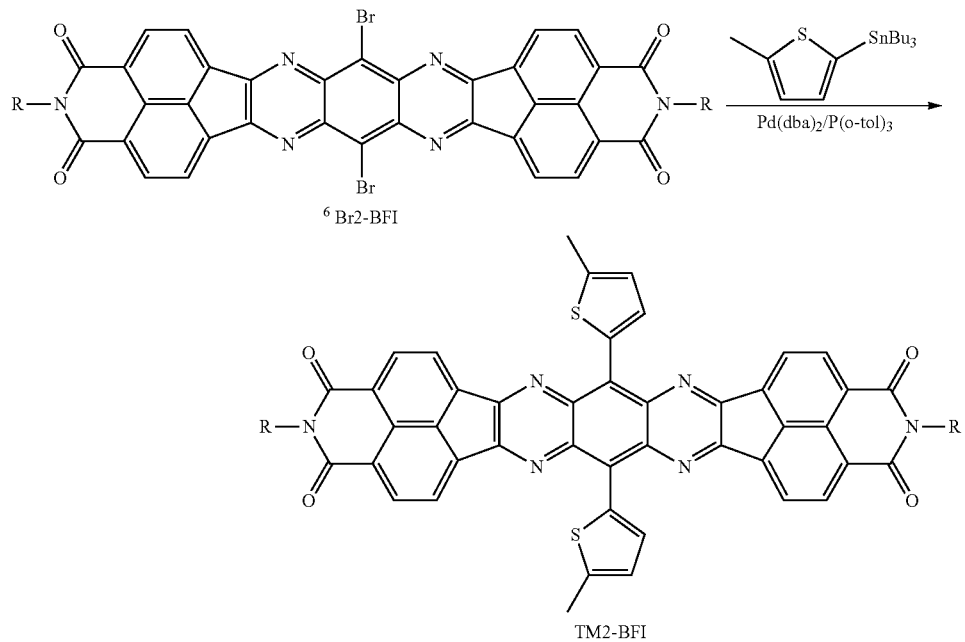

R = 2-decyltetradecyl

Under protection of argon, compound 6 (200 mg, 0.14 mmole), trimethyl(5-methylthiophen-2-yl)stannane (74 mg, 0.28 mmole), Pd(dba)$_2$ (3 mg) and P(°tol)$_3$ 96 mg) were charged into a reaction tube and dissolved in 10 mL of degassed toluene. The solution was slowly warmed up to 110° C. and kept stirring for 2 days. After cooling back to room temperature, the volatile materials were removed under high vacuum. The solids left were further purified through column chromatography with chloroform and methanol as the eluent solvents. The pure product was isolated as a blue solid. Yield: 147 mg, 71%. $^1$H NMR (CDCl$_3$, 500 MHz): δ=8.22 (d, $^3J$=6.0 Hz, 4H, Np), 8.13 (d, $^3J$=3.0 Hz, d, 2H, Th), 7.84 (dd, 4H, Np), 6.87 (d, $^3J$=2.0 Hz, 2H, Th), 3.42 (br, 4H, CH$_2$), 2.73 (s, 6H, ThMe), 1.68 (br, 2H, CH), 1.4-1.0 (m, 48H, CH$_2$), 0.90 (t, 12H, Me).

TM2-BFI exhibited two absorption bands in dilute chloroform solution similar to T2-BFI, one intense absorption with an absorption maximum ($λ_{max}$) at 411 nm which is due to the π-π* transition of the traazabenzodifluoranthene diimide moiety, and a weak low energy absorption at $λ_{max}$=585 nm which mainly arises from charge transfer from the central electron donating dithienylbenzene moiety to the naphthalene imide group. Comparably, the low energy absorption band was strongly red-shifted relative to that of 300° C. The excellent thermal stability of TM2-BFI is highly advantageous for applications in durable and robust organic electronics.

Example 12B

Synthesis and Characteristics of Compound TM2-BFI

Under protection of argon, Br2-BFI (200 mg, 0.14 mmol), trimethyl(5-methylthiophen-2-yl)stannane (74 mg, 0.28 mmol), Pd(dba)$_2$ (3 mg) and P(o-tol)$_3$ (6 mg) were charged into a reaction tube and dissolved in 10 mL of degassed toluene. The solution was slowly warmed up to 110° C. and kept stirring for 2 days. After cooling back to room temperature, the volatile materials were removed under high vacuum. The solids left were further purified through column chromatography with chloroform and methanol (400:1 v/v) as the eluent solvents (Rf=0.29). The pure product was isolated as a blue solid. Yield: 147 mg, 71%. $^1$H NMR (CDCl$_3$, 25° C., 500 MHz): δ=8.11 (d, 4H, $^3J$=6.0 Hz, Np), 8.06 (d, 2H, $^3J$=3.0 Hz, Th), 7.71 (d, 4H, $^3J$=6.0 Hz, Np), 6.78 (d, 2H, $^3J$=2.0 Hz, Th), 3.28 (br, 4H, CH$_2$), 2.65 (s, 6H, Me), 1.59 (m, 2H, CH), 1.4-1.0 (m, 80H, CH$_2$), 0.85 ppm (m, 12H, Me). $^{13}$C NMR (CDCl$_3$, 25° C., 500 MHz): 162.8, 151.5, 146.3, 136.5, 135.8, 135.6, 135.4, 132.1, 131.9, 130.3, 125.0, 124.5, 123.7, 122.7, 44.1, 36.9, 32.2, 31.7, 30.3, 30.0, 29.9, 29.6, 26.6, 22.9, 15.7, 14.4 ppm; HRMS (m/z): [M]$^+$ calcd. for C$_{92}$H$_{116}$N$_6$O$_4$S$_2$, 1434.07; found, 1433.81; elemental analysis calcd for C$_{92}$H$_{116}$N$_6$O$_4$S$_2$: C, 77.05%; H, 8.15%; N, 5.86%. found C, 77.23%; H, 8.16%; N, 5.91%.

Example 13

Transistors Based on Compound TM2-BFI

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). TM2-BFI was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(μWCo/2 L)(Vg-Vt)2. (Kang, S.-M.; Leblebici, Y. *CMOS Digital Integrated Circuits: Analysis and Design*, McGraw-Hill, New York, 1996.) The electron mobility of 0.028 cm$^2$ V$^{-1}$ s$^{-1}$ and hole mobility of 0.00036 cm$^2$ V$^{-1}$ s$^{-1}$ were obtained for transistors based on TM2-BFI.

Example 14A

Synthesis and Characteristics of Compound CN2-BFI

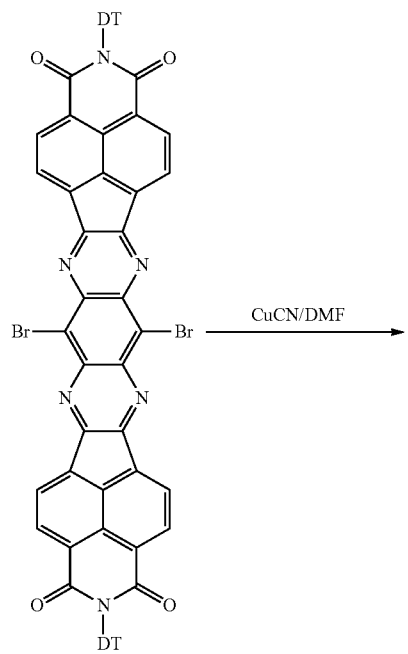

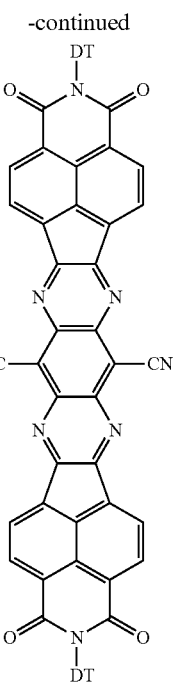

DT = 2-decyltetradecyl

Under protection of argon, compound 6 (200 mg, 0.14 mmole), CuCN (62.3 mg, 0.7 mmol) were charged into a reaction tube and suspended in 20 mL of degassed DMF. The mixture was slowly warmed up to 110° C. to 130° C. and kept stirring for 2 days. After cooling back to room temperature, the volatile materials were removed under high vacuum. The solids left were further purified through column chromatography with chloroform and methanol as the eluent solvents. The pure product was isolated as a yellow solid. Yield: 83 mg, 46%. $^1$H NMR (CDCl$_3$, 500 MHz): δ=8.77 (d, $^3$J=7.0 Hz, 4H, Np), 8.70 (d, $^3$J=7.0 Hz,Np), 4.15 (d, $^3$J=7.5 Hz, 4H, CH$_2$), 2.0 (Br, 12H, CH), 1.45-1.0 (m, 48H, CH$_2$), 0.90 (t, 12H, Me).

CN2-BFI exhibited two absorption bands in dilute chloroform solution similar to BFI. The optical band gap estimated from the absorption edge was 2.50 eV.

The electron affinity of CN2-BFI was characterized by cyclic voltammetry. CN2-BFI showed an quasi-reversible reduction wave at $E_{1/2}$=−0.35 V vs. SCE. No apparent oxidation was observed during an anodic scan in the range up to 1.2 V vs. SCE. The LUMO energy level of CN2-BFI calculated from the reduction onset was −4.3 eV.

CN2-BFI showed excellent thermal properties. Thermal gravimetric analysis (TGA) shows that CN2-BFI was thermally stabile up to 420° C. No apparent thermal transition was observed for CN2-BFI based on differential scanning calorimetry (DSC) scans in the temperature range of 20 to 300° C. The excellent thermal stability of CN2-BFI is highly advantageous for applications in durable and robust organic electronics.

Example 14B

Synthesis and Characteristics of Compound CN2-BFI

Under protection of argon, Br2-BFI (200 mg, 0.14 mmol), CuCN (62.3 mg, 0.7 mmol) were charged into a reaction tube and suspended in 20 mL of degassed DMF. The mixture was slowly warmed up to 110° C. to 130° C. and kept stirring for 2 days. After cooling back to room temperature, the volatile materials were removed under high vacuum. The solids left were further purified through column chromatography with chloroform and methanol (50:1 v/v) as the eluent solvents (Rf=0.34). The pure product was isolated as a yellow solid. Yield: 83 mg, 46%. $^1$H NMR (CDCl$_3$, 25° C., 500 MHz): δ=8.74 (d, $^3$J=7.5 Hz, 4H, Np), 8.66 (d, 4H, $^3$J=7.5 Hz, Np), 4.11 (d, $^3$J=7.0 Hz, 4H, CH$_2$), 1.97 (br, 2H, CH), 1.45-1.0 (m, 80H, CH$_2$), 0.86 ppm (t, 12H, Me); $^{13}$C NMR (CDCl$_3$, 25° C., 500 MHz): 163.1, 157.7, 141.4, 137.6, 134.0, 132.9, 126.2, 125.3, 117.0, 112.9, 45.2, 37.0, 32.2, 31.9, 30.3, 29.0, 29.6, 26.7, 22.9, 14.4 ppm; HRMS (m/z): [M]$^+$ calcd. for C$_{84}$H$_{106}$N$_8$O$_4$, 1290.83; found, 1290.88; elemental analysis calcd for C$_{84}$H$_{106}$N$_8$O$_4$: C, 78.10%; H, 8.27%; N, 8.67%. found C, 78.37%; H, 8.59%; N, 8.02%.

Part III

Example 15

Synthesis and Characteristics of Polymer PBFI-T

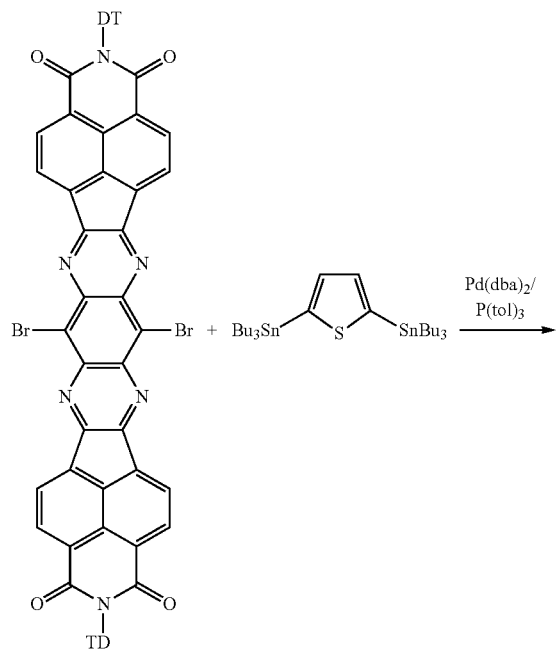

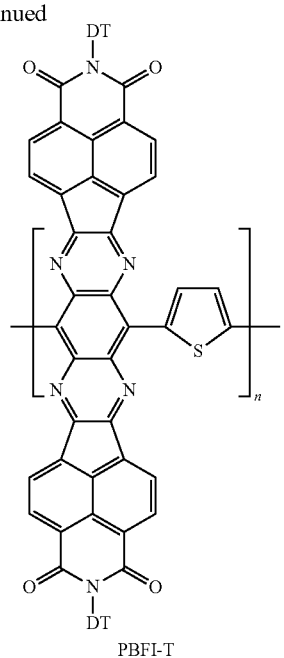

PBFI-T

DT = 2-decyltetradecyl

Compound 6 (Br2-BFI) (100 mg, 0.07 mmole) and 2,5-bis(tributylstannyl)thiophene (47.3 mg, 0.07 mmole) were dissolved in 12 mL of anhydrous toluene and purged with Ar for 10 min. A solution of Pd(dba)$_2$ (3 mg) and P(o-tol)$_3$ (6 mg) was added to the monomer solution. Pd(bda)$_2$, P(o-tol)$_3$ and 2,5-bis(tributylstannyl)thiophene were purchased from Aldrich and used as received.

The mixture was slowly heated to 110° C. and kept stirring at the temperature for 3 days. After cooling back to room temperature, the volatile materials were evaporated and the solids were dissolved in 6 mL of toluene and precipitated into 100 mL of methanol and concentric HCl mixed solvents (20 v:1 v). The green solid was collected by filtration and further purified by successive Soxhlet extraction with methanol, acetone and hexanes. Yield: (75 mg, 79.5%). GPC (at 60° C. in Chlorobenzene, against polystyrene standards) Mw=175,000, PDI=3.68.

Polymer PBFI-T exhibited good solubility in common organic solvent including chloroform, dichloromethane, chlorobenzene, dichlorobenzene, toluene, etc. As a result, it is suitable for solution processing (e.g., drop casting, spin coating, etc.) of thin films.

Polymer PBFI-T exhibited two absorption bands in a dilute chloroform solution: one intense high energy absorption at around $\lambda_{max}$=378 nm and a relatively weak low energy absorption band at $\lambda_{max}$=700 nm. There was no significant change for the high energy absorption band from the dilute solution to the thin films, but the low energy absorption was strongly red shifted due to more efficient intra- and inter-molecular charge transfer and inter-chain interaction. The optical band gap estimated from the absorption edge was 1.24 eV.

The electron affinity of PBFI-T was evaluated by cyclic voltammetry. BFI showed an unresolved quasi-reversible reduction waves at $E_{1/2}$=−1.10 V vs SCE. No apparent oxidation was observed during an anodic scan up to 1.2 V vs. SCE. Based on the onsets of reduction waves, the LUMO energy level of PBFI-T was estimated to be −3.80 eV.

The thermal behavior of BFI was investigated by thermogravimetric analysis (TGA) and differential scanning calorimetry (DSC). No apparent thermal transition was observed based on DSC scans in the temperature range of 30 to 300° C. TGA shows that BFI was thermally stabile up to 450° C. The excellent thermal stability of PBFI-T is highly advantageous for fabricating durable and robust organic electronics.

Figure 2A:
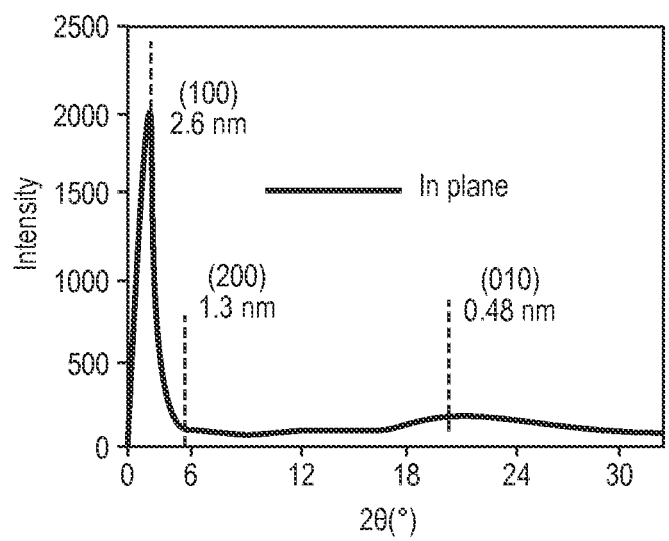
FIG. 2 shows XRD patterns of the thin film of an exemplary polymer described herein (PBFI-T), drop-casted on a glass substrate after annealing at 250° C. for 10 min. The plots of intensity vs 2θ were collected in a selected area; the incident angle between the input beam and the sample was fixed at 3°; the substrate is fixed at 90° (A) and the incident angle between the input beam and the sample was fixed at 5°; the substrate is fixed at 90° and 54.5° to give a in plane (green line) and out of plane (blue line, (B)) signals, respectively.
Figure 2B:
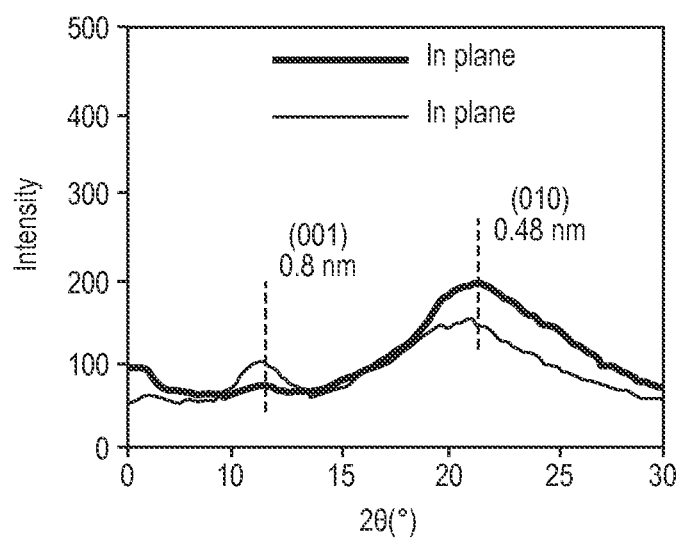

The x-ray diffraction patterns of a thin film of PBFI-T drop-casted on the glass substrate show strong first Bragg reflection indexed to the (100) plane and its weak second order (200) reflection at 3.35° and 6.5°, respectively indicative an edge-on-edge lamella packing (FIG. 2).

Example 16

Transistors Based on Polymer PBFI-T

A heavily n-doped silicon substrate with a thermally grown silicon dioxide layer (200 nm; capacitance density, $C_i$=17 nF/cm$^2$) acted as a gate electrode and a gate insulator, respectively. The substrates were cleaned by ultrasonication in acetone and isopropyl alcohol (30 min each) and dried by a flow of nitrogen gas. The surface of a silicon dioxide substrate was further cleaned by air-plasma (4 min) and further hydrophobically modified by either a monolayer of octyltrichlorosilane (OTS8), or a thin film of polymer insulators such as an amorphous fluoro-polymer (CYTOP) or cross-linked benzocyclobutene (BCB). A thin film of PBFI-T was deposited onto the modified substrate by simple spin-coating from a solution in dichloromethane (DCM) with a 10 vol % of 1,2-dichlorobenzene (ODCB). The thin films were annealed at various temperatures for 10 min on a hot-plate under argon environment. Source-drain electrodes (40 nm) were deposited onto the polymer films by vacuum thermal evaporation of gold or silver through a shadow mask, defining a channel width (W) of 1000 μm and a length (L) of 100 μm. Current-voltage (I-V) characteristics of the transistors were measured under nitrogen atmosphere by using a Signatone probe station and an HP4145B semiconductor parameter analyzer controlled by locally written LabView codes through a GPIB interface.

Figure 4:
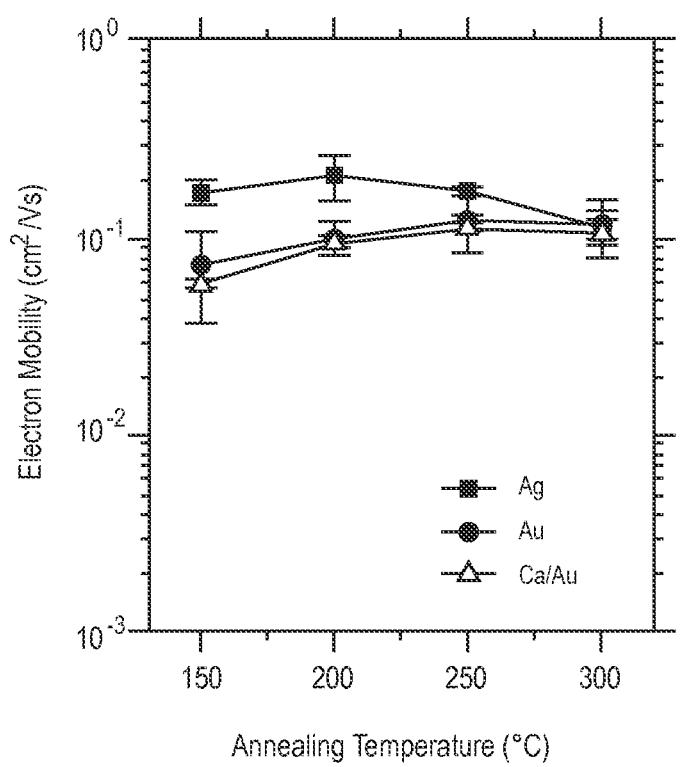
FIG. 4 shows annealing temperature dependence of electron mobility of PBFI-T transistors with various electrodes: silver (black square), gold (wine circle), and calcium capped with gold (green triangle).

The charge carrier mobilities were calculated from transfer curves using the standard saturation equation of metal-oxide-semiconductor field-effect transistors: Ids=(μWCo/2 L)(Vg−Vt)2. (Kang, S.-M.; Leblebici, Y. *CMOS Digital Integrated Circuits: Analysis and Design*, McGraw-Hill, New York, 1996.) The electron mobility of 0.3 cm$^2$ V$^{-1}$ s$^{-1}$ was obtained (The average saturation mobility of the devices with 100 nm-thick silver electrodes was 0.18±0.04 cm$^2$/Vs.), with an on/off current ratio of 10$^5$. The transistor characteristic curves of an n-channel field-effect transistor based on PBFI-T are shown in FIGS. 3A and 3B. The electron mobility was slightly dependent on the annealing temperature (150-300° C.) and the electrode metal (FIG. 4). Mobility was higher than, for example, mobilities reported in Examples 8 and 10.

Figure 5:
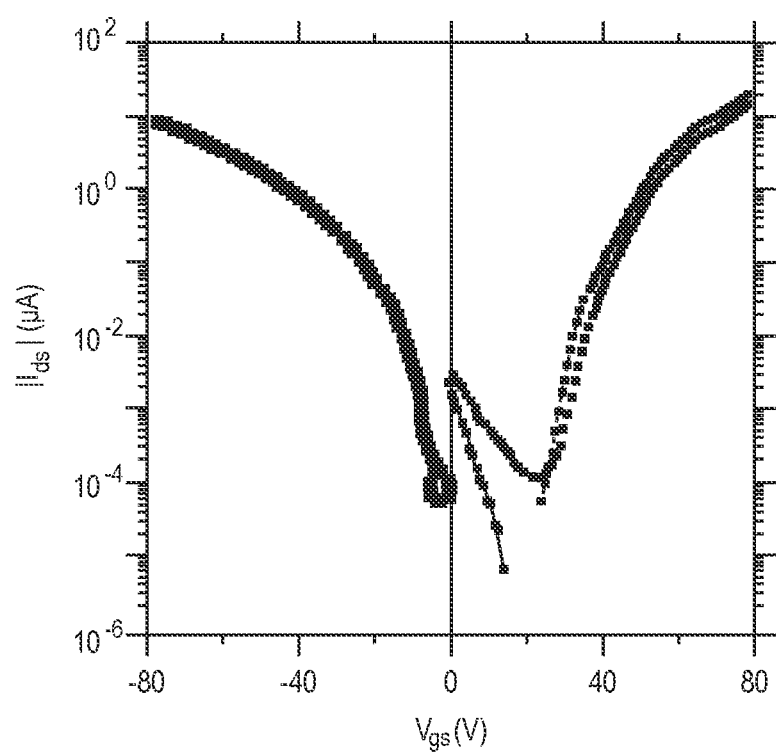
FIG. 5 shows transfer curves of constituent polymer transistors in polymer complementary inverters based on PBFI-T (n-channel) and PSOxTT (p-channel) transistors.
Figure 6A:
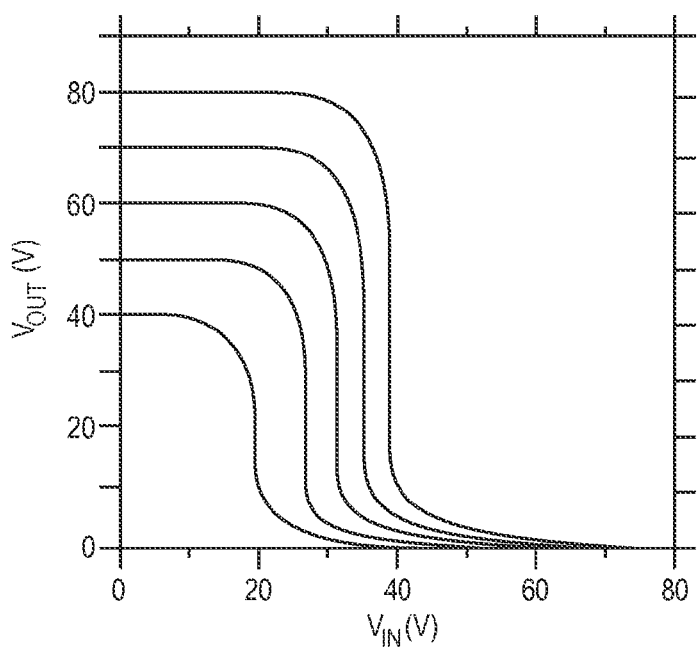
FIG. 6 shows static switching characteristics of the polymer complementary inverters based on PBFI-T (n-channel) and PSOxTT (p-channel) transistors: Output voltage (A), gain (B) and current (C) as a function of input voltage (VIN) with various power supply voltages (VDD).
Figure 6B:
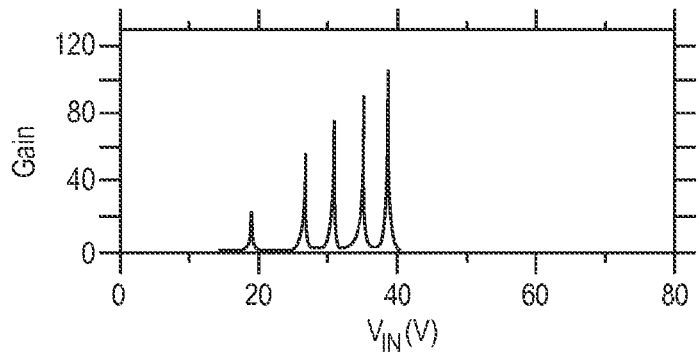
Figure 6C:
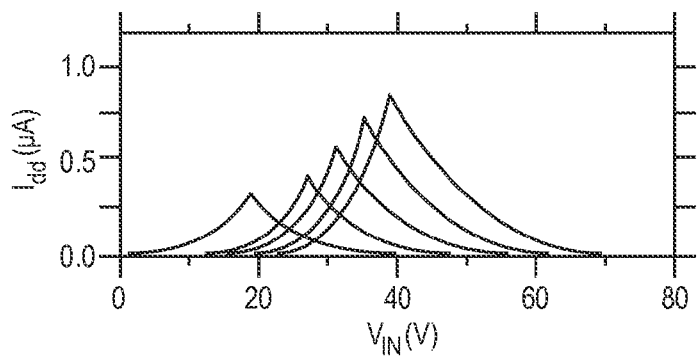

Complementary Invertors using PBFI-T as the n-channel component. Complementary inverters were fabricated by connecting n-channel PBFI-T OFETs with p-channel PSOxTT (see WO 2011/051292) OFETs. PSOxTT thin film was deposited by spin-coating from a solution in 1,2-dichlorobenzene (4-8 mg/mL) onto an OTS8-treated substrate. A voltage sweeping step was set to 0.1 V for the complementary inverter characterization. The current-voltage curves of constituent PBFI-T and PSOxTT OFETs (FIG. 5) showed comparable on-current and off-current, suggesting the operation of the inverter would be symmetric. By having same device architectures (i.e., 200 nm-thick SiO$_2$ with OTS8 and gold electrodes with W/L=10) for both transistors, the complementary inverters showed ideal switching characteristics with trip voltage at the half of supply voltage (V$_{DD}$) and voltage gain of 107 when V$_{DD}$=80 V (FIG. 6).

Example 17

Synthesis and Characteristics of Polymer PBFI-BT

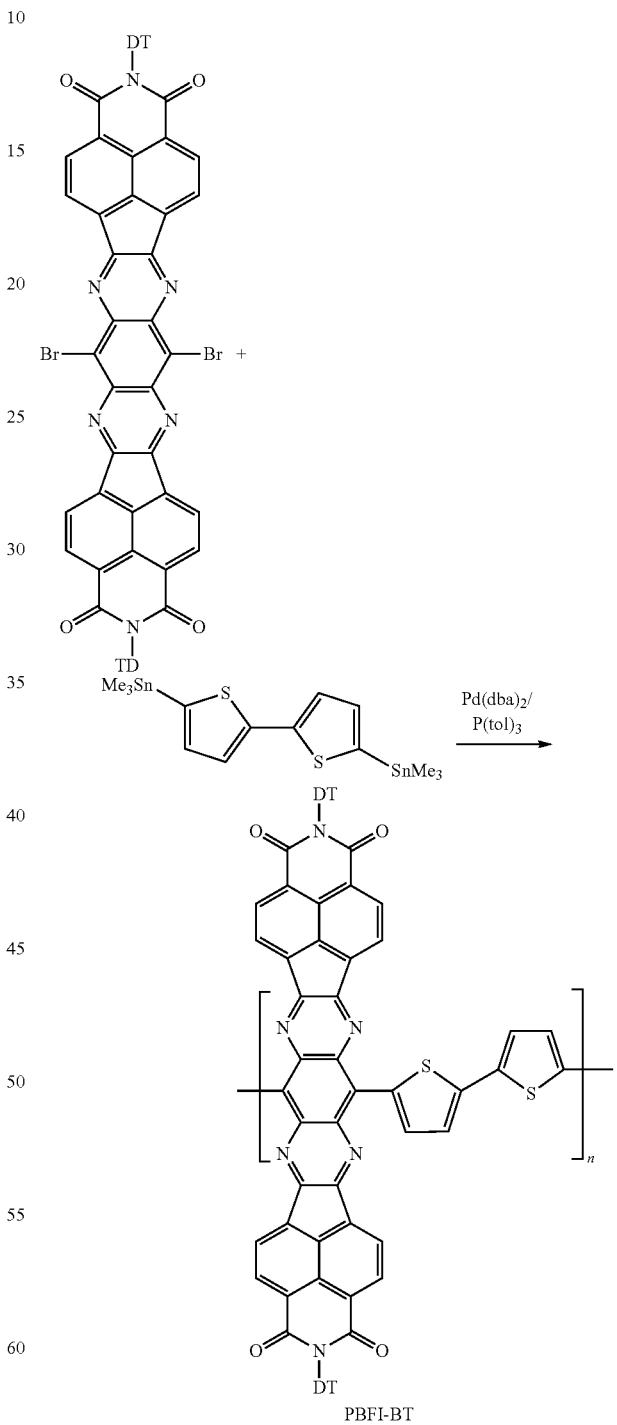

DT = 2-decyltetradecyl

PBFI-BT was synthesized and purified similarly to PBFI-T by using compound 6 (Br2-BFI) (200 mg, 0.14 mmol), 2,2'-bis(trimethylstannyl)-4,4'-bithiophene (69 mg, 0.14 mmol), 30 mL of toluene, Pd(dba)$_2$ (6 mg) and P(o-tol)$_3$ (12 mg). Yield: (141, 71.1%). Pd(bda)$_2$, P(o-tol)$_3$ and 2,2'-bis(trimethylstannyl)-4,4'-bithiophene were purchased from Aldrich and used as received.

PBFI-BT exhibited similar absorption as PBFI-T, and showed one intense high energy absorption band and one broad low energy absorption band. The low energy band of PBFI-BT was more strongly red-shifted compare to that of PBFI-T and showed at about $\lambda_{max}$=1000 nm for dilute chloroform solution and at about 1100 nm for the thin film. The optical band gap of PBFI-BT was estimated to be 0.95 eV.

PBFI-BT showed a quasi-reversible reduction at $E_{1/2}$=−1.08 V and a relatively weak oxidation wave at $E_p$=0.8 V. The HOMO and LUMO energy levels estimated from the oxidation and reduction onsets were −5.16 eV and −3.70 eV, respectively.

PBFI-BT also exhibited good thermal stability. No thermal transition up to 300° C. was observed during a DSC scan. TGA showed that PBFI-BT was thermally stable up to 450° C.

Example 18

Transistors Based on Polymer PBFI-BT

A heavily n-doped silicon substrate with a thermally grown silicon dioxide layer (200 nm; capacitance density, $C_i$=17 nF/cm$^2$) acted as a gate electrode and a gate insulator, respectively. The substrates were cleaned by ultrasonication in acetone and isopropyl alcohol (30 min each) and dried by a flow of nitrogen gas. The surface of a silicon dioxide substrate was further cleaned by air-plasma (4 min) and treated with octyltrichlorosilane (OTS8) by spin-coating from a chloroform solution (4 mM). The polymer semiconductor was deposited onto the substrate by drop casting from a suspension (10 mg/mL) in dichloromethane with 5-10 vol % of 1,2-dichlorobenzene. The thin films were annealed at various temperatures for 10 minutes on a hot-plate under argon environment. Source-drain electrodes (40 nm) were deposited onto the polymer films by vacuum thermal evaporation of gold or silver through a shadow mask, defining a channel width (W) of 1000 μm and a length (L) of 100 μm. Current-voltage (I-V) characteristics of the transistors were measured under nitrogen atmosphere by using a Signatone probe station and an HP4145B semiconductor parameter analyzer controlled by locally written LabView codes through a GPIB interface.

The charge carrier mobilities were calculated from transfer curves using the standard saturation equation of metal-oxide-semiconductor field-effect transistors: Ids=(μWCo/2 L)(Vg−Vt)2. (Kang, S.-M.; Leblebici, Y. *CMOS Digital Integrated Circuits: Analysis and Design*, McGraw-Hill, New York, 1996.) The electron mobility of 0.09 cm$^2$ V$^{-1}$ s$^{-1}$ was obtained, with an on/off current ratio of 10$^5$. The transistor characteristic curves of an ambipolar field-effect transistor based on PBFI-BT are shown in FIGS. 5C and 5D.

Example 19

Synthesis and Characteristics of Polymer PBFI-BDT

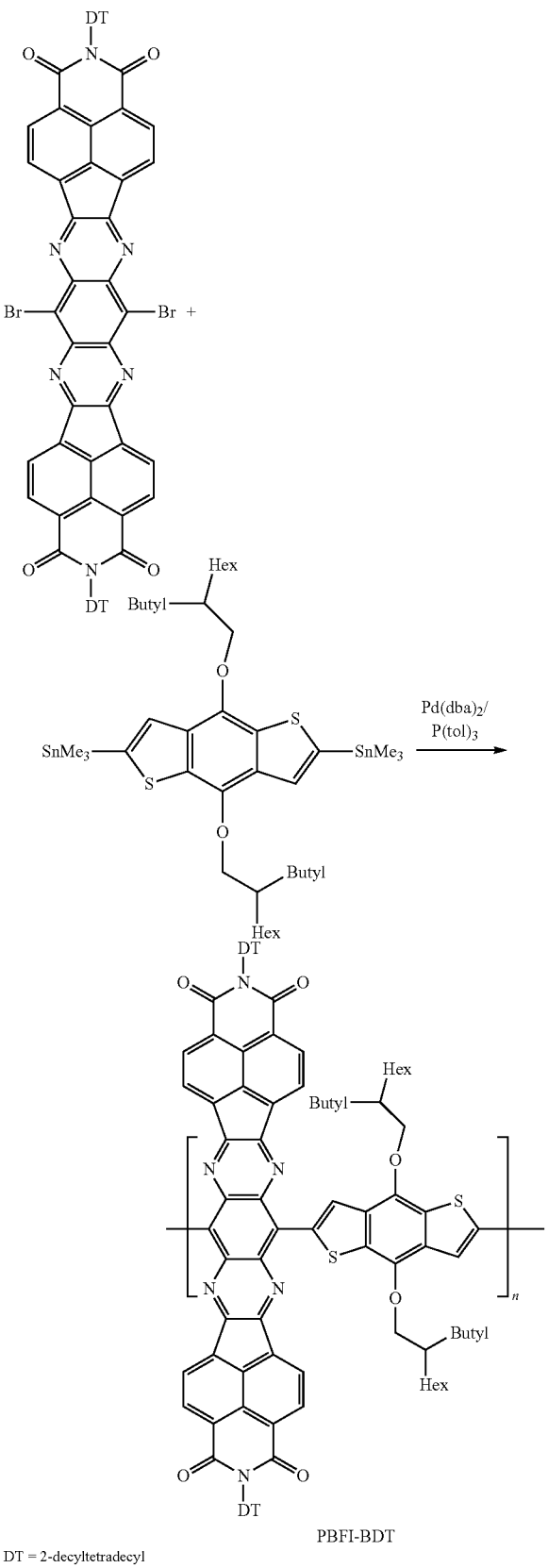

DT = 2-decyltetradecyl

PBFI-BDT

PBFI-BDT was synthesized and purified similarly to PBFI-T by using Compound 6 (Br2-BFI) (200 mg, 0.14 mmol), 2,2'-bis(trimethylstannyl)-4,8-di(2-butyloctyloxy)benzo[1,2-b;d,4-b]dithiophene (126 mg, 0.14 mmol), 30 mL of toluene, Pd(dba)$_2$ (6 mg) and P(o-tol)$_3$ (12 mg). Yield: (157, 62.3%). Pd(bda)$_2$ and P(o-tol)$_3$ were purchased from Aldrich and used as received. 2,2'-bis(trimethylstannyl)-4,8-di(2-butyloctyloxy)benzo[1,2-b;d,4-b]dithiophene was prepared according to reported procedures (Hundt et al., Org. Lett. 2009, 11, (19), 4422-4425.). GPC (at 60° C. in Chlorobenzene, against polystyrene standards) Mw=175,000, PDI=4.34.

PBFI-BDT exhibited good solubility in common organic solvents such as chloroform, dichloromethane, chlorobenzene, dichlorobenzene, toluene, etc. As a result, it is suitable for solution processing (e.g., spin coating, drop casting, etc.) of thin films.

PBFI-BDT exhibited similar absorption as PBFI-T and PBFI-BT, and showed an intense high energy absorption band at $\lambda_{max}$=390 nm and unresolved broad low energy absorption ranging from 550 nm to 1150 nm. The optical band gap calculated from the absorption edge was 0.92 eV.

PBFI-BDT exhibited good thermal stability. No apparent thermal transition was observed during a DSC scan in a temperature range from 30° C. to 300° C. TGA showed that PBFI-BDT was thermally stable up to 440° C.

Example 20

Transistors Based on Polymer PBFI-BDT

Field-effect transistors were fabricated on a heavily n-doped silicon substrate with thermally grown silicon dioxide gate insulator (200 nm; capacitance density, $C_i$=17 nF/cm$^2$). Photolithographically defined gold patterns (40 nm) with chromium adhesive layer (2 nm) acted as the source and drain electrodes in the bottom-contact/bottom-gate transistors, forming the channel width (W) of 800 μm and length (L) of 40 μm (W/L=20). The substrates were cleaned by ultrasonication with acetone and isopropyl alcohol and dried by flow of nitrogen. The surface of a silicon dioxide substrate was further cleaned by plasma and treated with octyltrichlorosilane (OTS8) to form a hydrophobic self-assembled monolayer (SAM). PBFI-BDT was deposited onto the substrate by spin-coating from a solution in chloroform. The devices were annealed at various temperatures under argon environment. Electrical characteristics of the devices were measured using an HP4145B semiconductor parameter analyzer under nitrogen atmosphere.

The charge carrier mobilities were calculated from transfer curves using the standard saturation equation of metal-oxide-semiconductor field-effect transistors: Ids=(μWCo/2 L)(Vg−Vt)$^2$. (Kang, S.-M.; Leblebici, Y. CMOS Digital Integrated Circuits: Analysis and Design, McGraw-Hill, New York, 1996.) An electron mobility of 1.3×10$^{-3}$ cm$^2$ V$^{-1}$ s$^{-1}$ and a hole mobility of 1.5×10$^{-4}$ cm$^2$ V$^{-1}$ s$^{-1}$ were obtained for transistors based on PBFI-BDT.

Example 21

Synthesis and Characteristics of Polymer PBFI-Se

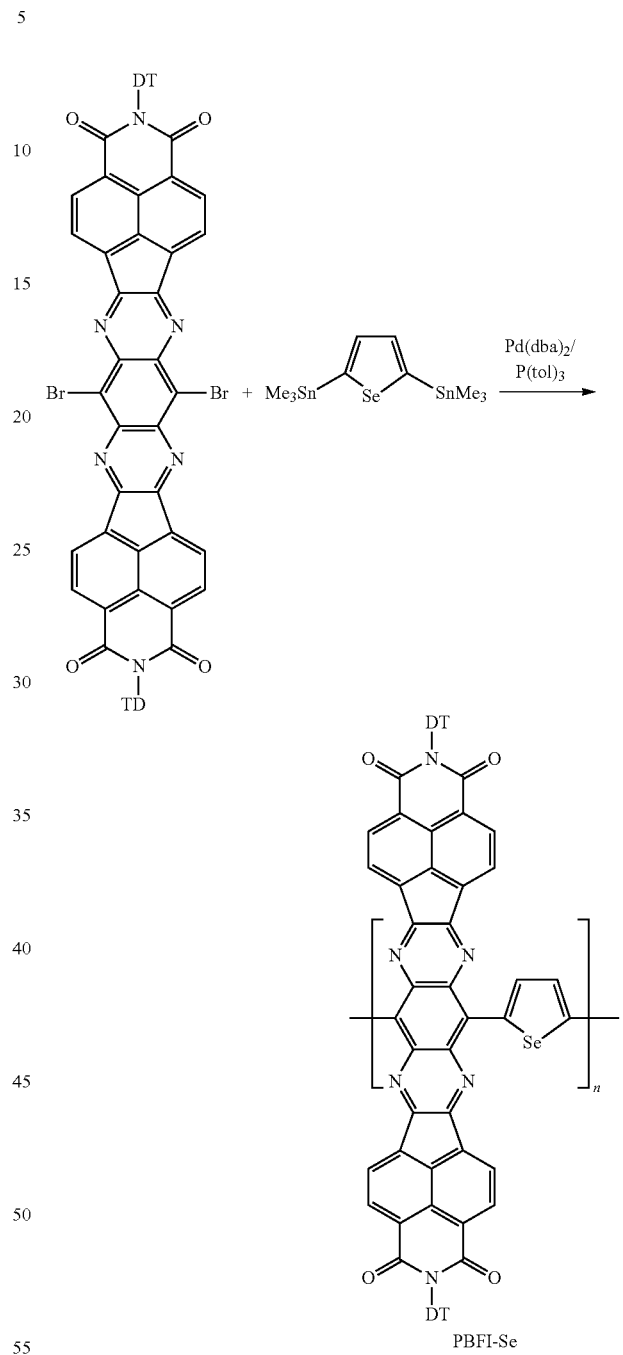

DT = 2-decyltetradecyl

PBFI-Se was synthesized and purified similarly to PBFI-T by using compound 6 (Br2-BFI) (200 mg, 0.14 mmole) and 2,5-bis(trimethylstannyl)selenophene (65 mg, 0.14 mmole) Yield: (126 mg, 64.4%). Pd(bda)$_2$ and P(o-tol)$_3$ were purchased from Aldrich and used as received. 2,5-bis(trimethylstannyl)selenophene was synthesized according to reported procedures (Chen, C.-H.; et al, Macromolecules 2009, 43, (2), 697-708.). GPC (at 60° C. in Chlorobenzene, against polystyrene standards) Mw=104,000, PDI=3.55.

PBFI-Se exhibited good solubility in common organic solvent including chloroform, dichloromethane, chlorobenzene, dichlorobenzene, toluene, etc. As a result, it is suitable for solution processing (e.g., drop casting, spin coating, etc.) of thin films.

PBFI-Se exhibited similar absorption as PBFI-T both in a dilute chloroform solution and as thin films: one intense high energy absorption at around $\lambda_{max}$=378 nm and a relatively weak low energy absorption band at $\lambda_{max}$=900 nm. There was no significant change for the high energy absorption band from the dilute solution to the thin films, but the low energy absorption was strongly red shifted due to more efficient intra- and inter-molecular charge transfer and interchain interaction. The optical band gap estimated from the absorption edge was 1.08 eV.

The thermal behavior of PBFI-Se was investigated by thermogravimetric analysis (TGA) and differential scanning calorimetry (DSC). No apparent thermal transition was observed based on DSC scans in the temperature range of 30 to 300° C. TGA shows that PBFI-Se was thermally stabile up to 430° C. The excellent thermal stability of PBFI-Se is highly advantageous for fabricating durable and robust organic electronics.

Example 22

Transistors Based on Polymer PBFI-Se

A heavily n-doped silicon substrate with a thermally grown silicon dioxide layer (200 nm; capacitance density, $C_i$=17 nF/cm²) acted as a gate electrode and a gate insulator, respectively. The substrates were cleaned by ultrasonication in acetone and isopropyl alcohol (30 min each) and dried by a flow of nitrogen gas. The surface of a silicon dioxide substrate was further cleaned by air-plasma (4 min) and treated with octyltrichlorosilane (OTS8) by spin-coating from a chloroform solution (4 mM). The polymer semiconductor was deposited onto the substrate by spin-coating at 3 krpm for 60 s from a solution (10 mg/mL) in dichloromethane with 5-10 vol % of 1,2-dichlorobenzene. The thin films were annealed at various temperatures for 10 min on a hot-plate under argon environment. Source-drain electrodes (40 nm) were deposited onto the polymer films by vacuum thermal evaporation of gold or silver through a shadow mask, defining a channel width (W) of 1000 μm and a length (L) of 100 μm. Current-voltage (I-V) characteristics of the transistors were measured under nitrogen atmosphere by using a Signatone probe station and an HP4145B semiconductor parameter analyzer controlled by locally written LabView codes through a GPIB interface.

The charge carrier mobilities were calculated from transfer curves using the standard saturation equation of metal-oxide-semiconductor field-effect transistors: Ids=(μWCo/2 L)(Vg−Vt)2. (Kang, S.-M.; Leblebici, Y. CMOS Digital Integrated Circuits: Analysis and Design, McGraw-Hill, New York, 1996.) The electron mobility of 0.0053 cm² V⁻¹ s⁻¹ was observed, with an on/off current ratio of 10⁵.

Example 23

Synthesis and Characteristics of Polymer PBFI-TT

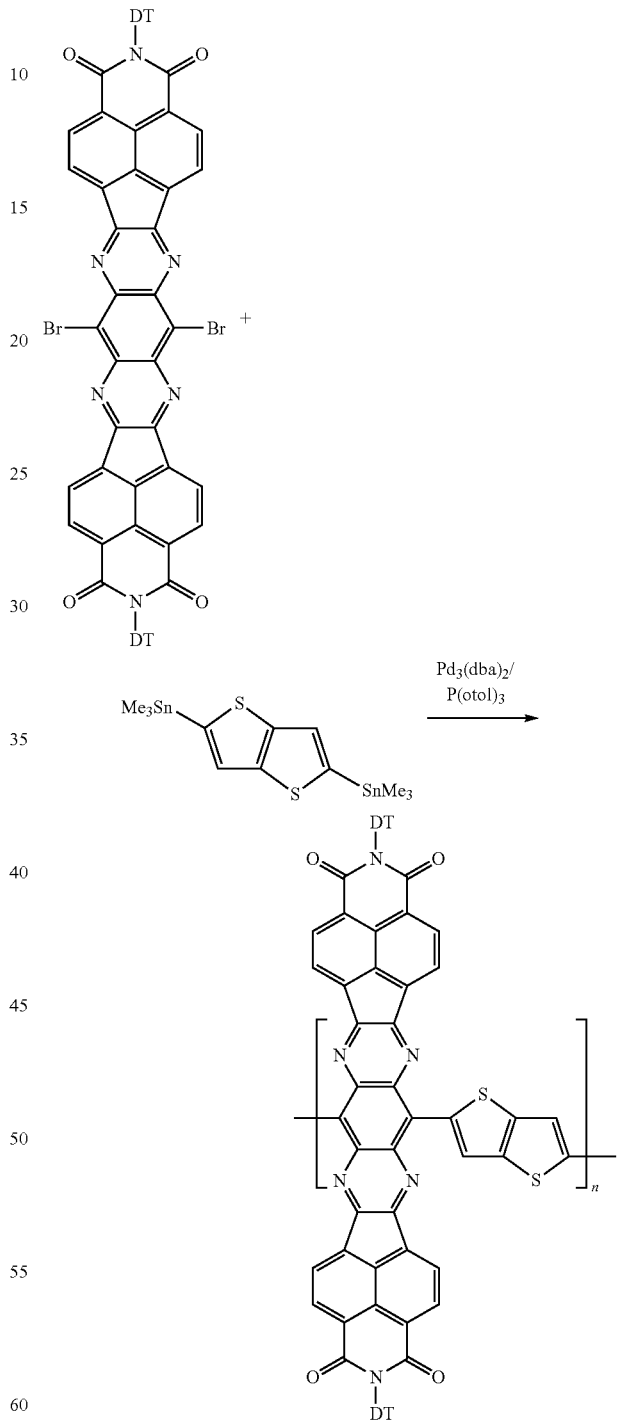

DT = 2-decyltetradecyl

PBFI-TT was synthesized and purified similarly to PBFI-T by using compound 6 (Br2-BFI) (100 mg, 0.07 mmole) and 2,5-bis(trimethylstannyl)thieno[3,2-b]thiophene (32.5 mg, 0.07 mmole) Yield: (68 mg, 75%). GPC (at 60° C. in Chlorobenzene, against polystyrene standards) Mw=136,000, PDI=12.8.

PBFI-TT exhibited good solubility in common organic solvent including chloroform, dichloromethane, chlorobenzene, dichlorobenzene, toluene, etc. As a result, it is suitable for solution processing (e.g., drop casting, spin coating, etc.) of thin films.

PBFI-TT exhibited similar absorption as PBFI-T both in a dilute chloroform solution and as thin films: one intense high energy absorption at around $\lambda_{max}$=388 nm and a relatively weak low energy absorption band at $\lambda_{max}$=700 nm. The optical band gap estimated from the absorption edge was 1.19 eV.

The thermal behavior of PBFI-Se was investigated by thermogravimetric analysis (TGA) and differential scanning calorimetry (DSC). No apparent thermal transition was observed based on DSC scans in the temperature range of 30 to 300° C. TGA shows that PBFI-Se was thermally stabile up to 438° C. The excellent thermal stability of PBFI-TT is highly advantageous for fabricating durable and robust organic electronics.

Example 24

Transistors Based on Polymer PBFI-TT

A heavily n-doped silicon substrate with a thermally grown silicon dioxide layer (200 nm; capacitance density, $C_i$=17 nF/cm$^2$) acted as a gate electrode and a gate insulator, respectively. The substrates were cleaned by ultrasonication in acetone and isopropyl alcohol (30 min each) and dried by a flow of nitrogen gas. The surface of a silicon dioxide substrate was further cleaned by air-plasma (4 min) and treated with octyltrichlorosilane (OTS8) by spin-coating from a chloroform solution (4 mM). The polymer semiconductor was deposited onto the substrate by spin-coating at 3 krpm for 60 s from a solution (10 mg/mL) in dichloromethane with 5-10 vol % of 1,2-dichlorobenzene. The thin films were annealed at various temperatures for 10 min on a hot-plate under argon environment. Source-drain electrodes (40 nm) were deposited onto the polymer films by vacuum thermal evaporation of gold or silver through a shadow mask, defining a channel width (W) of 1000 μm and a length (L) of 100 μm. Current-voltage (I-V) characteristics of the transistors were measured under nitrogen atmosphere by using a Signatone probe station and an HP4145B semiconductor parameter analyzer controlled by locally written LabView codes through a GPIB interface.

The charge carrier mobilities were calculated from transfer curves using the standard saturation equation of metal-oxide-semiconductor field-effect transistors: Ids=(μWCo/2 L)(Vg–Vt)2. (Kang, S.-M.; Leblebici, Y. *CMOS Digital Integrated Circuits: Analysis and Design*, McGraw-Hill, New York, 1996.) The electron mobility of 0.037 cm$^2$ V$^{-1}$ s$^{-1}$ was observed, with an on/off current ratio of 10$^5$.

Example 25

Synthesis and Characteristics of Polymer PBFI-BTDD

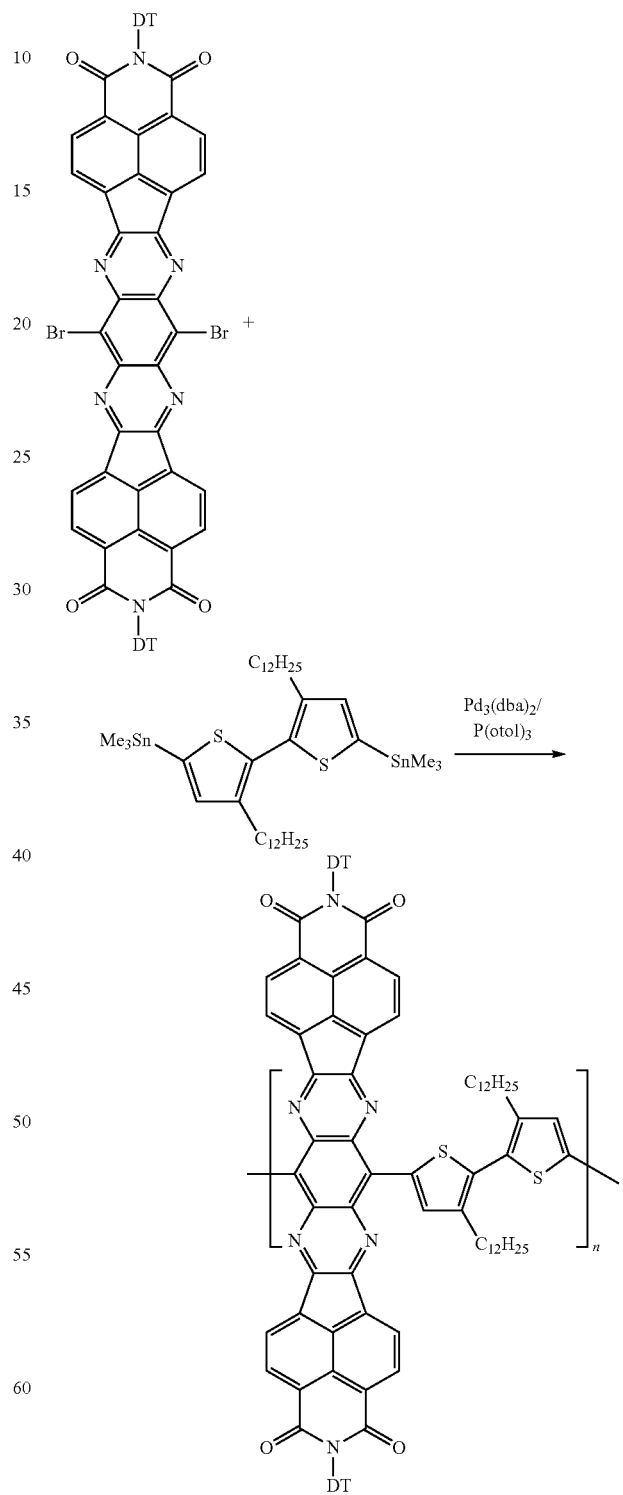

DT = 2-decyltetradecyl

PBFI-BTDD was synthesized and purified similarly to PBFI-BTDD by using compound 6 (Br2-BFI) (100 mg, 0.07 mmole) and (3,3'-didodecyl-2,2'-bithiophene-5,5'-diyl)bis(trimethylstannane) (116.2 mg, 0.14 mmole) Yield: (167 mg, 68.4%). GPC (at 60° C. in Chlorobenzene, against polystyrene standards) Mw=73,000, PDI=2.08.

PBFI-BTDD exhibited good solubility in common organic solvent including chloroform, dichloromethane, chlorobenzene, dichlorobenzene, toluene, etc. As a result, it is suitable for solution processing (e.g., drop casting, spin coating, etc.) of thin films.

The thermal behavior of PBFI-BTDD was investigated by thermogravimetric analysis (TGA) and differential scanning calorimetry (DSC). No apparent thermal transition was observed based on DSC scans in the temperature range of 30 to 300° C. TGA shows that PBFI-BTDD was thermally stabile up to 437° C. The excellent thermal stability of PBFI-BTDD is highly advantageous for fabricating durable and robust organic electronics.

Example 26

Transistors Based on Polymer PBFI-BTDD

A heavily n-doped silicon substrate with a thermally grown silicon dioxide layer (200 nm; capacitance density, $C_i$=17 nF/cm$^2$) acted as a gate electrode and a gate insulator, respectively. The substrates were cleaned by ultrasonication in acetone and isopropyl alcohol (30 min each) and dried by a flow of nitrogen gas. The surface of a silicon dioxide substrate was further cleaned by air-plasma (4 min) and treated with octyltrichlorosilane (OTS8) by spin-coating from a chloroform solution (4 mM). The polymer semiconductor was deposited onto the substrate by spin-coating at 3 krpm for 60 s from a solution (10 mg/mL) in dichloromethane with 5-10 vol % of 1,2-dichlorobenzene. The thin films were annealed at various temperatures for 10 min on a hot-plate under argon environment. Source-drain electrodes (40 nm) were deposited onto the polymer films by vacuum thermal evaporation of gold or silver through a shadow mask, defining a channel width (W) of 1000 µm and a length (L) of 100 µm. Current-voltage (I-V) characteristics of the transistors were measured under nitrogen atmosphere by using a Signatone probe station and an HP4145B semiconductor parameter analyzer controlled by locally written LabView codes through a GPIB interface.

The charge carrier mobilities were calculated from transfer curves using the standard saturation equation of metal-oxide-semiconductor field-effect transistors: Ids=(µWCo/2 L)(Vg−Vt)2. (Kang, S.-M.; Leblebici, Y. *CMOS Digital Integrated Circuits: Analysis and Design*, McGraw-Hill, New York, 1996.) The electron mobility of 0.024 cm$^2$ V$^{-1}$ s$^{-1}$ and a hole mobility of 0.00072 cm$^2$/Vs were obtained

Part IV

Example 27

Synthesis of Monomer ABPI-Br2

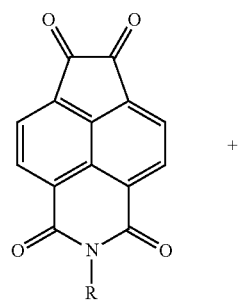

+

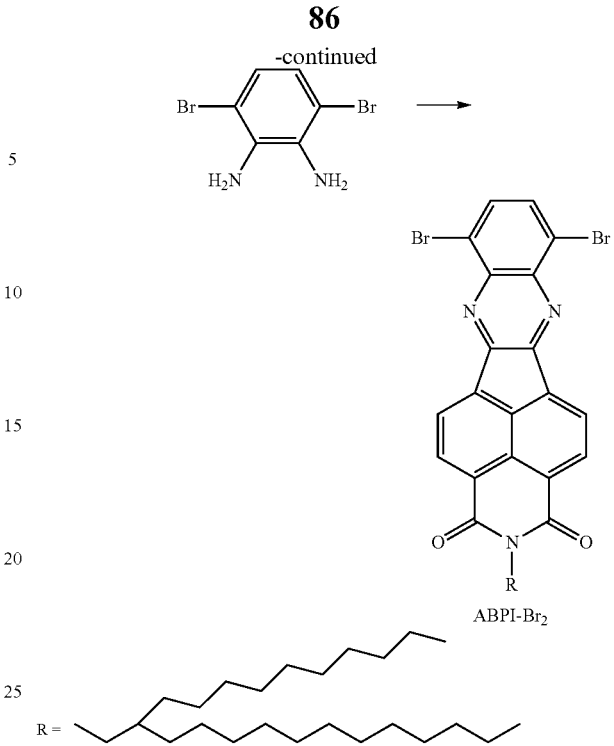

At 0° C., NaBH$_4$ (1.6 g, 43.2 mmole) was added in portions to the suspension of 4,7-dibromobenzo[c][1,2,5]thiadiazole (1.0 g, 3.4 mmole, purchased from Sigma-Aldrich) in ethanol. The mixture was allowed to warm up to room temperature. After stirring over night, the reaction was quenched with water. The organic phase was extracted with ether and followed with a standard aqueous work up. The volatile materials were removed in vacuo and the product was isolated as a white solid. Without further purification, the crude material was used in the next step. Yield: 750 mg (82.9%).

Inside a reaction tube, 3,6-dibromobenzene-1,2-diamine (112 mg, 0.42 mmole) and 2-(2-decyltetradecyl)-1H-indeno[6,7,1-def]isoquinoline-1,3,6,7(2H)-tetraone (200 mg, 0.42 mmole, synthesized according to Example 1) were suspended in 5 mL of ethanol. The mixture was heated to reflux and kept stirring at the temperature for 48 hours. After cooling back to room temperature, the yellow precipitate was collected by filtration. The crude materials were purified by column chromatography on silica gel with using hexanes and CHCl$_3$ mixed solvents as the eluent. Yield: 254 mg (85.8%). $^1$H NMR (CDCl3, 500 MHz): δ=8.75 (d, 2H, 3J=7.0 Hz, Nh), 8.65 (d, 2H, 3J=7.0 Hz, Nh), 8.00 (s, 2H, Ph), 4.18 (d, 2H, 3J=7.0 Hz, CH2), 2.02 (m, 1H, CH), 1.5-1.3 (m, 40H, CH2), 0.87 (m, 6H, Me). HRMS (m/z): [M]$^+$ calcd. for C$_{44}$H$_{55}$Br$_2$N$_3$O$_2$, 817.73; found, 818.23.

Example 28

Synthesis of Compound ATPI1

Tri-o-tolylphosphine, bis(dibenzylideneacetone) palladium (0) (Pd(dba)$_2$), 4,7-dibromobenzo[c][1,2,5]thiadiazole and 2,5-dibromo-3,4-dinitrothiophene were purchased from Aldrich and used as received. 3',4'-dinitro-3,3'''-dioctyl-2,2':5',2''-terthiophene (Beaupre, S. *Chem. Mater.* 2009, 21, 1504-1513), 2-hexyl-1-decylamine (Guo, X.; et al, *Org. Lett.* 2008, 10, (23), 5333-5336) and 1,4-dibromobenzene- 2,3-diamine (Hong, D.-J.; et al, *Chem. Commun.* 2010, 46, (27), 4896-4898) were synthesized according to reported procedures.

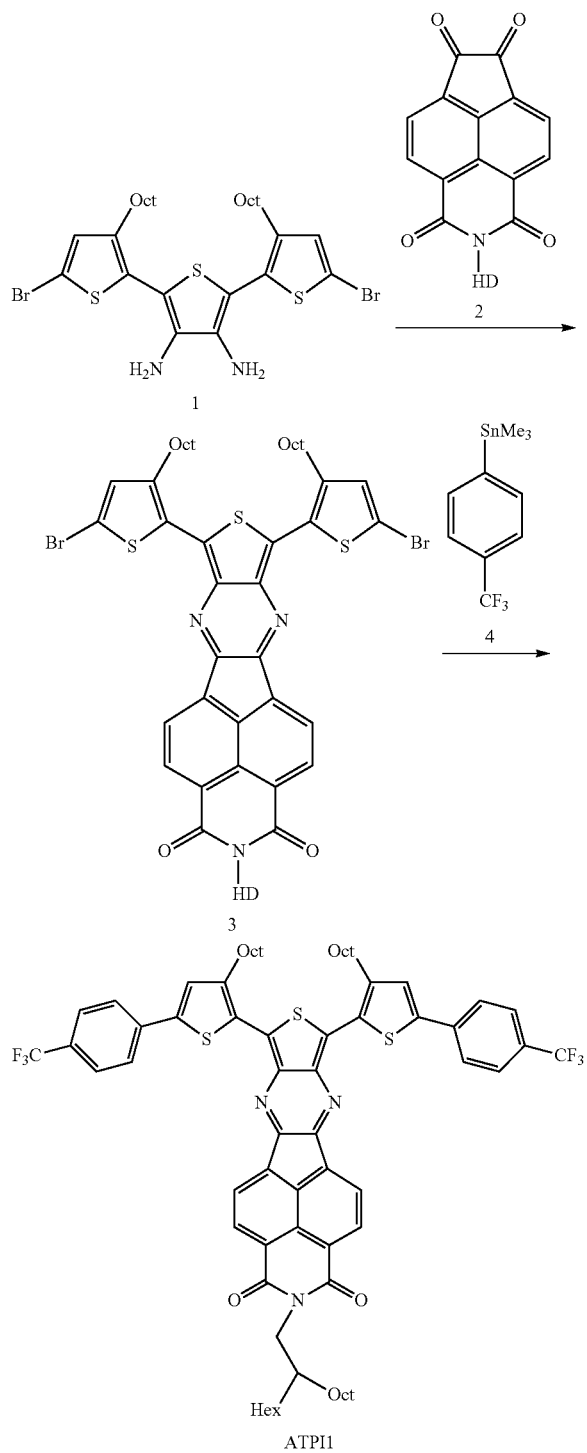

5,5"-dibromo-3',4'-dinitro-3,3"-dioctyl-2,2':5',2"-terthiophene. At room temperature, 3',4'-dinitro-3,3"-dioctyl-2,2':5',2"-terthiophene (562 mg, 1.0 mmole) was suspended in CHCl₃ and trifluoroacetic acid mixed solvents. N-bromosuccinimide (400 mg, 2.25 mmole) was added in portions. The mixture was kept stirring over night and slowly warmed up to 45 to 50° C. After stirring for additional 12 hours, the reaction was quenched by water followed by a standard aqueous work-up. The crude materials were purified by column chromatography on silica gel with using hexanes and ethyl acetate mixed solvents as the eluent. Yield: 342 mg (47.6%). $^1$H NMR (CDCl₃, 500.046 MHz): δ=7.02 (s, 2H, Th), 2.54 (t, 4H, CH₂), 1.58 (m, 4H, CH₂), 1.4-1.2 (t, 20H, CH₂), 0.9 (m, 6H, Me).

Compound 1 (3',4'-diamino-5,5"-dibromo-3,3"-dioctyl-2,2':5',2"-terthiophene). 5,5"-dibromo-3',4'-dinitro-3,3"-dioctyl-2,2':5',2"-terthiophene (180 mg, 0.25 mmole) was suspended in 6 mL of ethanol and 5.5 mL of HCl mixture under argon. To the mixture, Sn (1.28 g, 10.7 mmole) was added in portions. After stirring at room temperature over night, the mixture was neutralized with KOH (25%). The organic phase was extracted with ethyl acetate. The crude materials were directly used in the next step without further purification.

Compound 3. Inside a reaction tube, Compound 1 (147 mg, 0.22 mmole) and Compound 2 (105 mg, 0.22 mmole, synthesized according to Example 1) were suspended in 5 mL of ethanol. The mixture was heated to reflux and kept stirring at the temperature for 48 hours. After cooling back to room temperature, the blue precipitate was collected by filtration and further purified through column chromatography on silica gel. Yield: 172 mg (70%). $^1$H NMR (CDCl₃, 300 MHz): δ=9.50 (d, 2H, $^3$J=7.0 Hz, Np), 8.04 (d, 2H, $^3$J=7.0 Hz, Np), 6.68 (s, 2H, Th), 4.14 (q, 2H, CH₂), 2.58 (t, 4H, CH₂), 2.01 (m, 1H, CH), 1.61 (m, 4H, CH₂), 1.5-1.2 (m, 44H, CH₂), 1.0-0.8 (m, 12H, Me).

ATPI1. Compound 3 (110 mg, 0.1 mmole), trimethyl(4-trifluoromethyl)phenylstannane (74 mg, 0.24 mmole) and tetrakis(triphenylphosphine)palladium(0) (4.6 mg, 0.004 mmole) were dissolved in degassed toluene. The solution was heated to 100 to 110° C. and kept stirring for 24 hours. After cooling back to room temperature, the volatile materials were removed in vacuo. The solid residue was further purified by column chromatography on silica gel with hexanes and CHCl₃ mixed solvents as the eluent. The pure product was isolated as a green solid. Yield: 76 mg (61.7%). $^1$H NMR (CDCl₃, 500 MHz): δ=8.35 (d, 2H, $^3$J=7.0 Hz, Np), 7.91 (d, 2H, $^3$J=7.0 Hz, Np), 7.61 (d, 4H, $^3$J=8.0 Hz, Ph), 7.52 (d, 4H, $^3$J=8.0 Hz, Ph), 6.91 (s, 2H, Th), 3.93 (d, 2H, $^3$J=7.0 Hz, CH₂), 2.46 (br, 4H, CH), 1.92 (m, 1H, CH), 1.5-1.2 (m, 48H, CH₂), 1.0-0.8 (m, 12H, Me); $^{13}$C NMR (CDCl₃, 125.7 MHz): 163.4, 151.9, 142.9, 142.3, 137.1, 136.8, 136.2, 136.1, 132.0, 129.0, 127.1, 126.1, 126.1, 126.0, 126.0, 125.1, 123.7, 121.3, 32.2, 32.1, 32.1, 31.9, 31.7, 30.5, 30.4, 30.1, 30.0, 29.9, 29.9, 29.7, 29.6, 26.7, 26.6, 22.9, 14.3, 14.3;

Example 29

Synthesis of Compound ATPI2

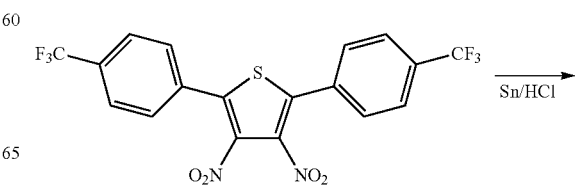

89

-continued

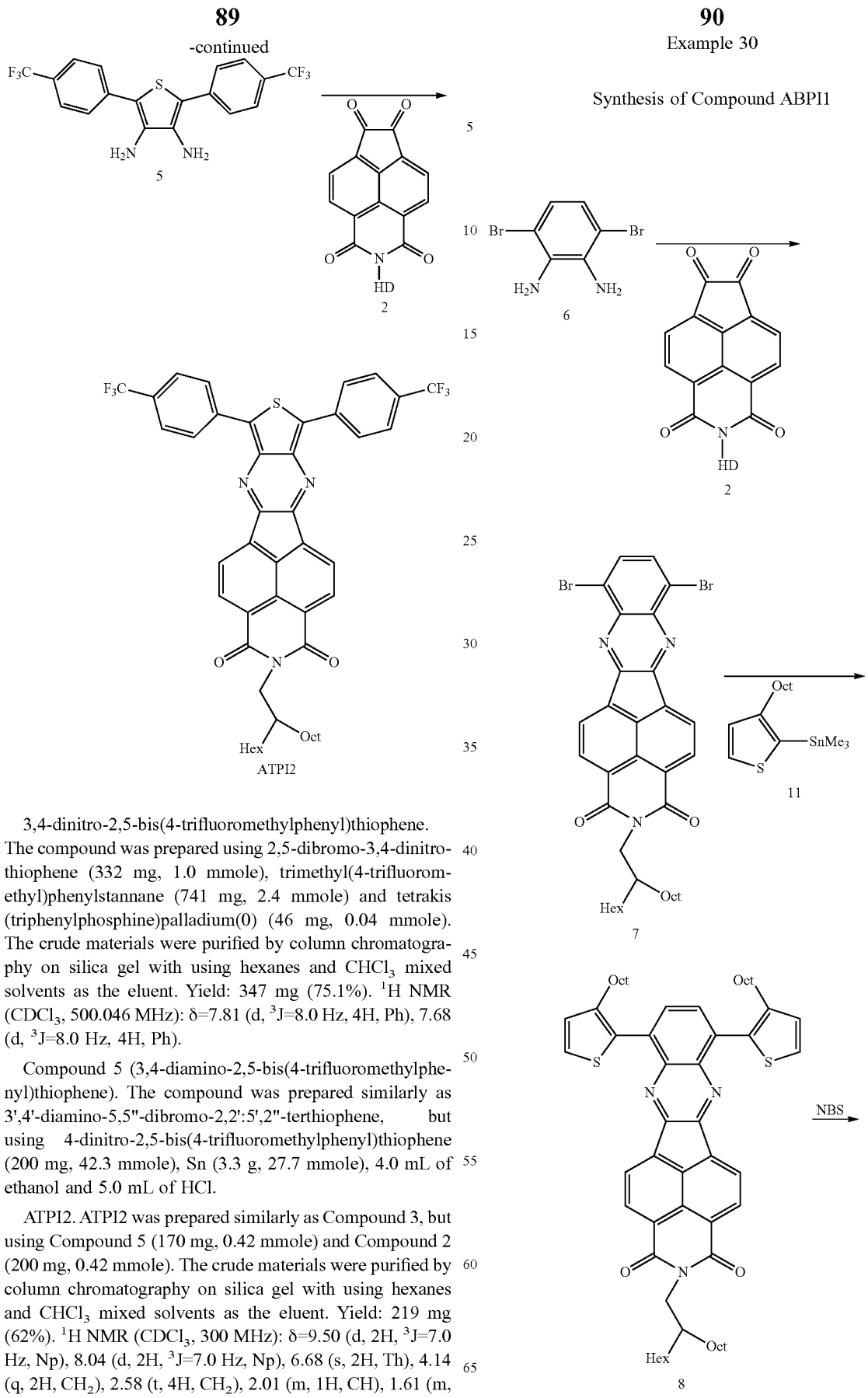

ATPI2

3,4-dinitro-2,5-bis(4-trifluoromethylphenyl)thiophene. The compound was prepared using 2,5-dibromo-3,4-dinitrothiophene (332 mg, 1.0 mmole), trimethyl(4-trifluoromethyl)phenylstannane (741 mg, 2.4 mmole) and tetrakis(triphenylphosphine)palladium(0) (46 mg, 0.04 mmole). The crude materials were purified by column chromatography on silica gel with using hexanes and $CHCl_3$ mixed solvents as the eluent. Yield: 347 mg (75.1%). $^1$H NMR ($CDCl_3$, 500.046 MHz): δ=7.81 (d, $^3J$=8.0 Hz, 4H, Ph), 7.68 (d, $^3J$=8.0 Hz, 4H, Ph).

Compound 5 (3,4-diamino-2,5-bis(4-trifluoromethylphenyl)thiophene). The compound was prepared similarly as 3',4'-diamino-5,5"-dibromo-2,2':5',2"-terthiophene, but using 4-dinitro-2,5-bis(4-trifluoromethylphenyl)thiophene (200 mg, 42.3 mmole), Sn (3.3 g, 27.7 mmole), 4.0 mL of ethanol and 5.0 mL of HCl.

ATPI2. ATPI2 was prepared similarly as Compound 3, but using Compound 5 (170 mg, 0.42 mmole) and Compound 2 (200 mg, 0.42 mmole). The crude materials were purified by column chromatography on silica gel with using hexanes and $CHCl_3$ mixed solvents as the eluent. Yield: 219 mg (62%). $^1$H NMR ($CDCl_3$, 300 MHz): δ=9.50 (d, 2H, $^3J$=7.0 Hz, Np), 8.04 (d, 2H, $^3J$=7.0 Hz, Np), 6.68 (s, 2H, Th), 4.14 (q, 2H, $CH_2$), 2.58 (t, 4H, $CH_2$), 2.01 (m, 1H, CH), 1.61 (m, 4H, $CH_2$), 1.5-1.2 (m, 44H, $CH_2$), 1.0-0.8 (m, 12H, Me).

90

Example 30

Synthesis of Compound ABPI1

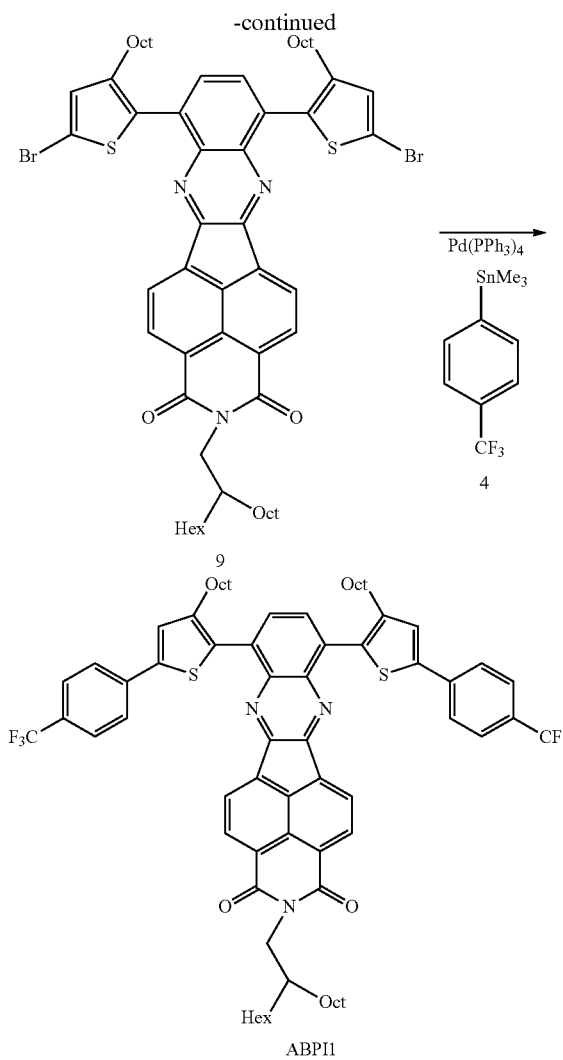

further purified through column chromatography on silica gel. The product was isolated as a red solid. Yield: 123 mg (87.6%). $^1$H NMR (CDCl$_3$, 500 MHz): δ=8.70 (d, 2H, $^3$J=7.0 Hz, Np), 8.49 (d, 2H, $^3$J=8.0 Hz, Np), 7.82 (s, 2H, Ph), 7.14 (s, 2H, Th), 4.16 (d, 2H, $^3$J=7.5 Hz, CH$_2$), 2.58 (t, 4H, CH$_2$), 2.04 (m, 1H, CH), 1.68 (m, 4H, CH$_2$), 1.5-1.3 (m, 44H, CH$_2$), 0.87 (t, 6H, Me), 0.77 (t, 6H, Me).

ABPI1. ABPI1 was prepared similarly as ATPI1, but using Compound 9 (123 mg, 0.11 mmole), trimethyl(4-trimethyl)phenylstannane (83 mg, 0.27 mmole) and tetrakis(triphenylphosphine)palladium(0) (5.0 mg, 0.004 mmole). The crude materials were purified by column chromatography on silica gel with using hexanes and CHCl$_3$ mixed solvents as the eluent. Yield: 347 mg (75.1%). $^1$H NMR (CDCl$_3$, 500.046 MHz): δ=8.69 (d, $^3$J=7.0 Hz, 2H, Np), 8.47 (d, $^3$J=7.0 Hz, 2H, Np), 7.94 (s, 2H, Ph), 7.84 (d, $^3$J=7.0 Hz, 4H, Ph), 7.71 (d, $^3$J=8.0 Hz, 4H, Ph), 7.51 (s, 2H, Th), 4.16 (d, $^3$J=7.5 Hz, 2H, CH$_2$), 2.66 (t, $^3$J=7.5 Hz, 4H, CH$_2$), 2.01 (m, 1H, CH), 1.79 (m, 4H, CH$_2$), 1.5-1.1 (m, 44H, CH$_2$), 0.86 (t, $^3$J=7.0 Hz, 6H, CH$_3$), 0.86 (t, $^3$J=7.0 Hz, 6H, CH$_3$); $^{13}$C NMR (CDCl$_3$, 125.7 MHz): 164.2, 154.2, 143.7, 142.8, 140.5, 138.3, 137.4, 135.8, 135.0, 134.4, 132.9, 132.6, 129.7, 129.5, 126.8, 126.4, 126.1, 125.7, 124.9, 123.7, 45.2, 37.3, 32.3, 32.3, 32.2, 32.2, 31.0, 30.5, 30.3, 30.2, 30.0, 30.0, 29.7, 29.6, 26.9, 23.1, 23.0, 14.5, 14.5.

Example 31

Synthesis of Compound ABPI2

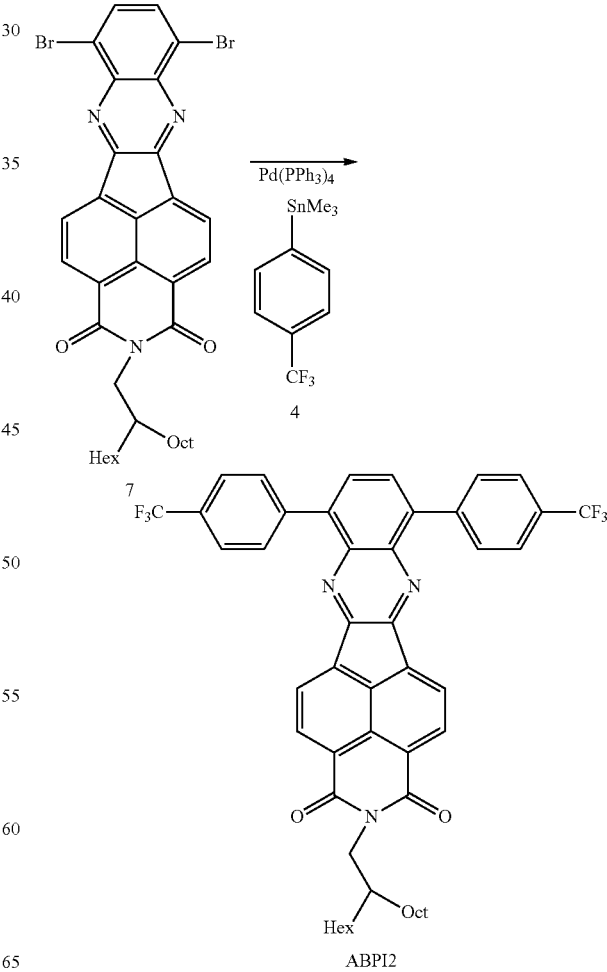

Compound 6 and Compound 7 were synthesized according to Example 27.

Compound 8. Under argon protection, Compound 7 (140 mg, 0.20 mmole), trimethyl(3-octyl)thienylstannane (171 mg, 0.47 mmole), Pd(dba)$_2$ (2.3 mg, 0.004 mmole) and P(o-tol)$_3$ (4.6 mg, 0.016 mmole) were dissolved in 7 mL of toluene and transferred into a reaction tube. The solution was heated to 100 to 110° C. and kept stirring for 48 hours. After cooling back to room temperature, the volatile materials were removed in vacuo. The solid residue was further purified by column chromatography on silica gel. Yield: 120 mg (64.1%). $^1$H NMR (CDCl$_3$, 300.xxx MHz): δ=8.67 (d, 2H, $^3$J=7.0 Hz, Np), 8.44 (d, 2H, $^3$J=7.0 Hz, Np), 7.87 (s, 2H, Ph), 7.52 (d, 2H, $^3$J=5.0 Hz, Th), 7.20 (d, 2H, $^3$J=5.0 Hz, Th), 4.17 (d, 4H, $^3$J=7.2 Hz, CH$_2$), 2.63 (t, 4H, CH$_2$), 2.02 (m, 1H, CH), 1.72 (m, 4H, CH$_2$), 1.6-1.0 (m, 44H, CH$_2$), 0.86 (t, 6H, Me), 0.77 (t, 6H, Me).

Compound 9. At room temperature, N-bromosuccinimide (60 mg, 0.34 mmole) was slowly added to a solution of Compound 8 (120 mg, 0.13 mmole) in CHCl$_3$. The solution was kept stirring over night and then heated to 50° C. for additional 12 hours. When TLC showed that almost all the starting materials were consumed, the reaction mixture was cooled back to room temperature and quenched with water. After a standard aqueous work up, the crude materials were ABPI2. ABPI2 was prepared similarly as ATPI1, but using Compound 7 (110 mg, 0.16 mmole), trimethyl(4-trimethyl)phenylstannane (115 mg, 0.37 mmole) and tetrakis (triphenylphosphine)palladium(0) (7.2 mg, 0.06 mmole). The crude materials were purified by column chromatography on silica gel. Yield: 96 mg (73.6%). $^1$H NMR (CDCl$_3$, 500.046 MHz): δ=8.69 (d, $^3$J=7.5 Hz, 2H, Ph), 8.42 (d, $^3$J=7.5 Hz, 2H, Ph), 7.98 (d, $^3$J=8.5 Hz, 4H, Np), 7.96 (s, 2H, Ph), 7.89 (d, $^3$J=8.5 Hz, 4H, Np), 4.17 (d, $^3$J=7.0 Hz, 2H, CH$_2$), 2.01 (m, 1H, CH), 1.5-1.2 (m, 24H, CH$_2$), 0.9-0.8 (m, 6H, CH$_3$); $^{13}$C NMR (CDCl$_3$, 125.7 MHz): 164.1, 154.2, 142.1, 140.8, 139.6, 137.6, 135.7, 132.9, 131.7, 131.3, 125.7, 125.5, 125.0, 123.5, 45.2, 37.3, 32.3, 32.3, 32.2, 30.5, 30.2, 30.0, 29.7, 27.0, 23.1, 14.5.

Example 32

Characterization of ATPI1, ATPI2, ABPI1 and ABPI2

ATPI1, ATPI2, ABPI1 and ABPI2 showed good solubility in common organic solvents such as chloroform, toluene, dichloromethane, chlorobenzene, etc, which is advantageous for solution processing device fabrication techniques.

The thermogravimetric analyses (TGA) show that all four compounds had similar thermal stabilities. High thermal decomposition temperatures (T$_d$, 5% weight loss) were found in the range from 390° C. to 410° C. Differential scanning calorimetry (DSC) was used to further investigate the thermal behaviors of the molecules. Among them, ABPI1 exhibited the highest stability and no apparent transition was observed in the temperature range from 30° C. to 300° C. The other molecules exhibited one or two thermal transitions during DSC scans from 30° C. to 300° C. The thermal decomposition temperature (T$_d$), the melting transition temperature (T$_m$) and the corresponding recrystallization temperatures (T$_c$) are summarized in Table 1.

TABLE 1

|       | Tm/° C. $^a$ | Tc/° C. $^a$ | Td/° C. $^b$ |
|-------|------|----------|------|
| ATPI1 | 120  | 97, 68   | 391  |
| ATPI2 | 218  | 178/176  | 388  |
| ABPI1 | 145, 201 | 163, 118 | 413  |
| ABPI2 | n/a  | n/a      | 316  |

$^a$ from DSC scans at 20° C./min under nitrogen.
$^b$ from TGA at 10° C./min under nitrogen.

All four molecules exhibited two absorption bands in dilute solution: the relatively intense high energy absorption band was mainly in the region from 300 nm to 400 nm, with the exception of ATPI1, whose high energy absorption band was much broader and extended to 450 nm in chloroform solution; the weak low energy absorption band strongly depended on the main chain structure of the molecules. On one hand, ATPI1 and ATPI2, with a thieno-core, exhibited strongly red-shifted low energy absorption compared to ABPI-based molecules; on the other hand, this band was red-shifted going from ABPI1 and ATPI1 to ABPI2 and ATPI2 because of the extended π-conjugation resulted from the two additional thiophene rings in the main chains. Going from the dilute solution to the thin films, the low energy absorption was red shifted for a few tens of nm, while the high energy absorption was almost the same with the exception of that of ATPI1, which was broad and red-shifted. The optical energy gap estimated from the absorption edge varied from 1.53 eV for ATPI1, 2.05 eV for ATPI2, 2.14 eV for ABPI1, to 2.51 eV for ABPI2, indicating a significant change in the electron structures by variation of the chemical structures. Fusion with the electron-donating thiophene units or extending π-conjugation with thiophene groups favors a narrower energy gap.

The electron affinities of the oligomers were evaluated by cyclic voltammetry. A quasi-reversible reduction wave was observed at −1.05 V to −1.35 V vs. SCE, except that ATPI2 exhibited an irreversible reduction at −1.3 V. The LUMO energy levels estimated from the scan onsets varied from −3.44 eV for ATPI1, −3.74 eV for ATPI2, to 3.62 eV for both ABPI1 and ABPI2. With two additional thiophenes, ATPI1 and ABPI1 also showed an irreversible oxidation event at 0.55 V and 1.05 V vs. SCE, respectively. The HOMO was ca. −5.09 eV for ATPI1 and ca. −5.59 eV for ABPI1. However, no apparent oxidation signal up to 1.0 V (vs. SCE) was detected for ATPI2 and ABPI2 during anodic scans indicating that the HOMO energy levels were significantly decreased (Lower than −5.70 eV) by removing the two thiophene moieties from the main chains. The high electron affinity and large ionization potentials of ATPI2 and ABPI2 are desired for applications in n-channel OFETs since it can increase the hole injection barrier and block the hole transport.

The planar structure and high electron affinity of the resulting molecules are highly advantageous for n-type organic semiconductors. Bottom gate/bottom contact field-effect transistors were fabricated using spin coated ATPI- and ABPI-based thin films as active layer. While ATPI1- and ABPI1-based transistors exhibited ambipolar charge transport, ATPI2- and ABPI2-based transistors exhibited unipolar n-type charge transport.

In summary, a family of novel organic semiconductors was designed and synthesized through attaching the naphthalene imide group onto different π-conjugated oligomers. The formed acenaphtoarylenepyrazine imide moieties have a desirable planar structure for efficient solid state packing. The photophysical and electrochemical properties of the resulting molecules varied with the main chain structures and thus can be tuned.

$^1$H NMR and $^{13}$C NMR spectra were recorded on a Bruker AV500 at 500 MHz using either deuterochloroform (CDCl$_3$) as the solvent. Mass spectra were obtained from Bruker AutoFlex II Matrix-Assisted LASER Desorption Ionization—Time of Flight Mass Spectrometer (MALDI-TOF) using benzo[α]pyrene as a matrix recorded in a (+)-reflector mode. Thermogravimetric analyses of the polymers were conducted on a TA Instrument model Q50TGA. A heating rate of 10° C./min under a flow of N$_2$ was used with runs conducted from room temperature to 800° C. Cyclic voltammetry was performed on an EG&G Princeton Applied Research potentiostat/galvanostat (model 273A). Data were analyzed by using a Model 270 Electrochemical Analysis System Software on a PC computer. A three-electrode cell was used, using platinum wire electrodes as both counter and working electrode. Silver/silver ion (Ag in 0.1 M AgNO$_3$ solution, Bioanalytical System, Inc.) was used as a reference electrode. Ferrocene was used as an internal standard with Ferrocene/ferrocenium (Fc/Fc$^+$) couple at 0.16 V vs SCE. All solutions were purged with argon for 20 min before each experiment. UV-Vis absorption spectra were collected on a Perkin-Elmer model Lambda 900 UV/Vis/near-IR spectrophotometer. The photoluminescence (PL) emission spectra were obtained with a Photon Technology International (PTI) Inc. ModelQM2001-4 spectrofluorimeter.

Part V

Example 33

Synthesis of Ar-PABPI Polymers

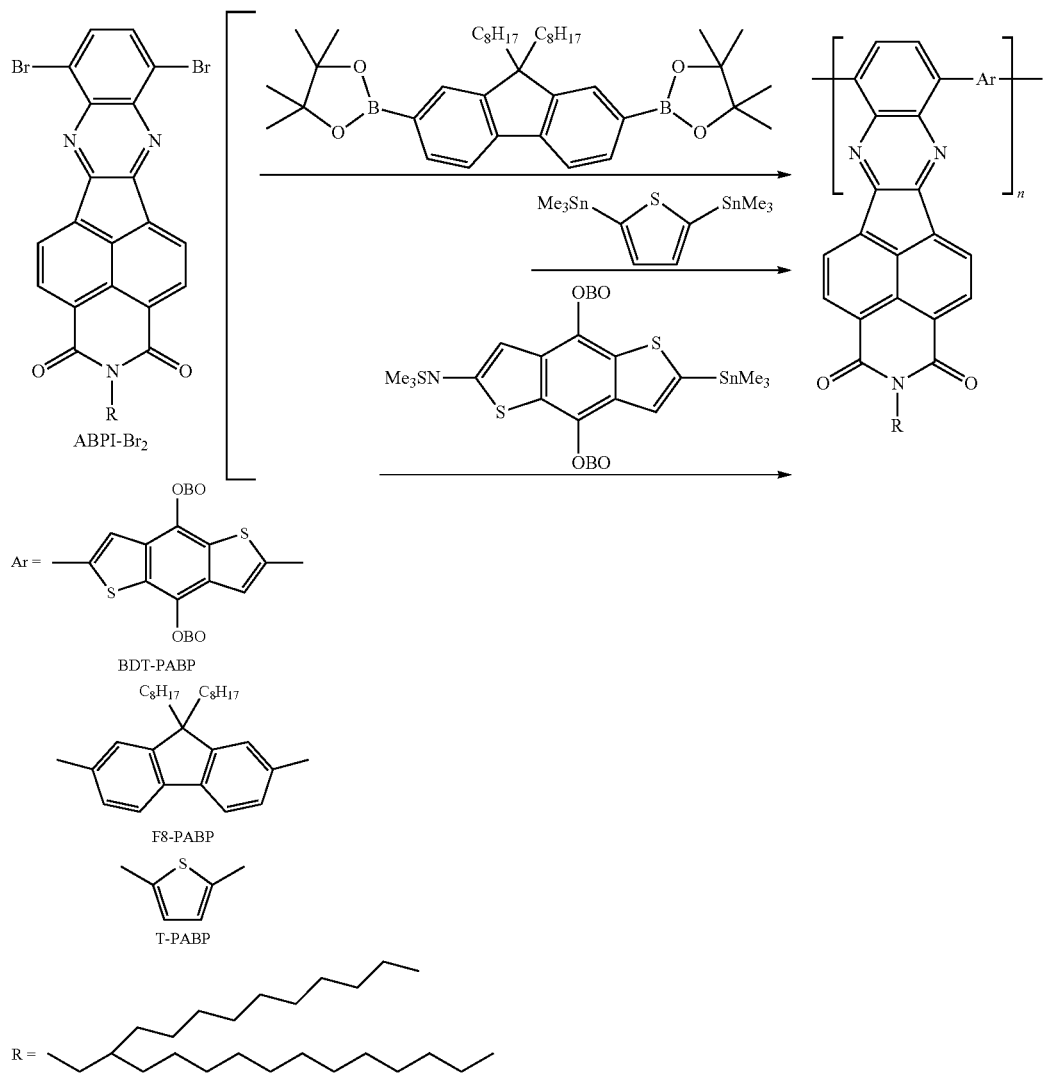

Chromium trioxide and bis(dibenzylideneacetone)palladium(0), tri-o-tolylphosphine, tatrakis(tripheylphosphine)palladium(0), 4,7-dibromobenzo[c]-1,2,5-thiadiazole, and 2,5-dibromo-3,4-dinitrothiophene were purchased from Sigma-Aldrich. Acenaphthylene dicarboxylic acid imide, 3,6-dibromobenzene-1,2-diamine (Hong, D.-J.; et al, *Chem. Commun.* 2010, 46, (27), 4896-4898), 9,9-dioctyl-2,7-bis(4,4,5,5-tetramethyl-1,3,2-dioxaborolane)fluorene (Geng, Y.; et al, *Chem. Mater.* 2003, 15, (2), 542-549), and 2,6-bis(trimethylsannanyl)-4,8-bis(2-butyloctoxyl)benzo[1,2-b:4,5-b']dithiophene (Hundt, N.; et al, *Org. Lett.* 2009, 11, (19), 4422-4425) were synthesized according to reported procedures.

Synthesis of T-PABPI

Under argon protection, ABPI-Br2 (250 mg, 0.31 mmole), 2,5-bis(trimethylsannanyl)thiophene (125 mg, 0.31 mmole), Pd(dba)2 (3.0 mg, 0.005 mmole) and P(o-tol)3 (6.0 mg, 0.010 mmole) were dissolved in 10 mL of toluene and transferred into a reaction tube. The solution was heated to 100 to 110° C. and kept stirring for 72 hours. After cooling back to room temperature, the volatile materials were removed in vacuo. The solid residue was re-dissolved in 8 mL of toluene and precipitated into 100 mL of methanol/HCl (20 v:1 v) mixed solvents. The solids were collected and subjected to sequential Soxhlet extraction with methanol, acetone, hexanes. T-PABPI was isolated as a blue solid. Yield: 156 mg (68.1%).

Synthesis of F8-PABPI

Under argon protection, ABPI-Br2 (200 mg, 0.24 mmole), 9,9-dioctyl-2,7-bis(4,4,5,5-tetramethyl-1,3,2-dioxaborolane)fluorene (157 mg, 0.24 mmole), Pd(PPh3)4 (11.3 mg, 0.010 mmole) were dissolved in 10 mL of toluene, transferred into a reaction tube followed by adding 6 mL of K2CO3 aqueous solution (2M). The solution was heated to 100 to 110° C. and kept stirring for 72 hours. After cooling back to room temperature, the organic phase was collected and dried in vacuo. The solid residue was re-dissolved in 8 mL of toluene and precipitated into 100 mL of methanol/HCl (20 v:1 v) mixed solvents. The solids were collected and subjected to sequential Soxhlet extraction with methanol, acetone, hexanes. F8-PABPI was isolated as a red solid. Yield: 167 mg (66.5%).

Synthesis of BDT-PABPI

Under argon protection, ABPI-Br2 (200 mg, 0.24 mmole), 2,6-bis(trimethylsannanyl)-4,8-bis(2-butyloctoxyl)benzo[1,2-b:4,5-b']dithiophene (217.4 mg, 0.24 mmole), Pd(dba)2 (3.0 mg, 0.005 mmole) and P(o-tol)3 (6.0 mg, 0.01 mmole) were dissolved in 10 mL of toluene and transferred into a reaction tube. The solution was heated to 100 to 110° C. and kept stirring for 72 hours. After cooling back to room temperature, the volatile materials were removed in vacuo. The solid residue was re-dissolved in 8 mL of toluene and precipitated into 100 mL of methanol/HCl (20 v:1 v) mixed solvents. The solids were collected and subjected to sequential Soxhlet extraction with methanol, acetone, hexanes. BDT-PABPI was isolated as a green solid. Yield: 181 mg (62.1%).

Example 34

Characterization of Ar-PABPI Polymers

Both BDT-PABPI and F8-PABPI showed good solubility in common organic solvents, such as chloroform, chlorobenzene, toluene, tetrahydrofuran, etc. The weight average molecular weight $M_w$ measured by gel permeation chromatography (GPC) analysis in chlorobenzene at 60° C. against polystyrene standards was 71.1 KDa for BDT-PABPI with a polydispersity index (PDI) of 3.9, and was 21.9 KDa for F8-PABPI with a PDI of 2.6. On the other hand, the solubility of T-PABPI was low, possibly due to lack of solubilizing groups on the thiophene ring and the better coplanarity between the thiophene unit and ABPI unit.

Thermal gravimetric analysis shows that the three polymers exhibited moderate to high thermal stability. The thermal decomposition temperatures ($T_d$) varied from 330° C. for BDT-PABPI, 440° C. for T-PABPI to 445° C. for F8-PABPI. Differential scanning calorimetry scans show that no apparent thermal transition was observed in the temperature range from 30° C. to 300° C.

Similar absorption was observed for T-PABPI and BDT-PABPI. They both showed two absorption bands: one presents in the region from 500 to 900 nm and the other in the region from 300 to 490 nm. The optical energy band gaps estimated from the absorption edges were 1.48 eV for T-PABPI and 1.53 eV for BDT-PABPI. While for F8-PABPI, both absorption bands experienced a strong blue-shift and the optical band gap was ca. 2.18 eV, which is consistent with the fact that fluorene is a weaker electron donor with relatively poorer electron delocalization than thiophene and benzodithiophene.

The electronic structures of the polymers were further investigated by cyclic voltammetry. BDT-PABPI exhibited two quasi-reversible reduction events at ca. −1.11 and −1.55 V (vs. SCE, E1/2) and an irreversible oxidation event at ca. 0.80 V (vs. SCE, E1/2). One irreversible reduction and oxidation event was observed for T-PABPI at ca. −1.02 V and 0.58 V, respectively. While for F8-PABPI, no oxidation signal was observed up to 1.2 V (vs. SCE) indicating a relatively high ionization potential due to the weak electron-donating property of fluorene moieties. Both BDT-PABPI and T-PABPI exhibited ambipolar electrochemical properties, i.e. they can be reduced and oxidized electrochemically at relatively low potentials, which is again in good agreement with the fact that benzodithiophene and thiophene are stronger electron-donors. The LUMO and HOMO energy levels calculated from the scan onsets of the cyclic voltammograms were −3.56 eV and −5.31 eV for BDT-PABPI, −3.62 eV and −5.22 eV for T-PABPI, and −3.52 eV (LUMO) for F8-PABPI, respectively.

In summary, a new acceptor-type functional group, acenaphthylene imide, was successfully incorporated into three polymers, BDT-PABPI, T-PABPI and F8-PABPI. A high electron affinity of 3.52 eV to 3.62 eV was observed. Depending on the second repeat unit, the HOMO ranged from −5.22 eV for T-PABPI, −5.31 eV for BDT-PABPI to lower than −5.90 eV for F9-PABPI.

$^1$H NMR and $^{13}$C NMR spectra were recorded on a Bruker AV500 at 500 MHz using either deuterochloroform (CDCl$_3$) as the solvent. Mass spectra were obtained from Bruker AutoFlex II Matrix-Assisted LASER Desorption Ionization—Time of Flight Mass Spectrometer (MALDI-TOF) using benzo[α]pyrene as a matrix recorded in a (+)-reflector mode. Thermogravimetric analyses of the polymers were conducted on a TA Instrument model Q50TGA. A heating rate of 10° C./min under a flow of N$_2$ was used with runs conducted from room temperature to 800° C. Cyclic voltammetry was performed on an EG&G Princeton Applied Research potentiostat/galvanostat (model 273A). Data were analyzed by using a Model 270 Electrochemical Analysis System Software on a PC computer. A three-electrode cell was used, using platinum wire electrodes as both counter and working electrode. Silver/silver ion (Ag in 0.1 M AgNO$_3$ solution, Bioanalytical System, Inc.) was used as a reference electrode. Ferrocene was used as an internal standard with Ferrocene/ferrocenium (Fc/Fc$^+$) couple at 0.16 V vs SCE. All solutions were purged with argon for 20 min before each experiment. UV-vis absorption spectra were collected on a Perkin-Elmer model Lambda 900 UV/vis/near-IR spectrophotometer. The photoluminescence (PL) emission spectra were obtained with a Photon Technology International (PTI) Inc. ModelQM2001-4 spectrofluorimeter.

What is claimed is:
1. A compound represented by formula (VII):

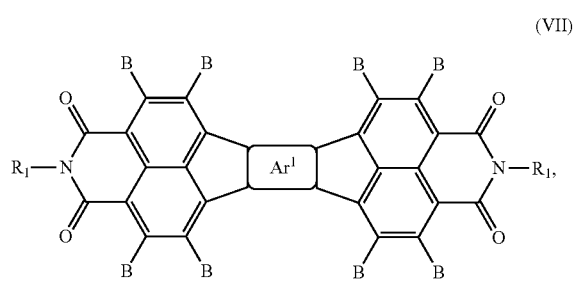

(VII)

wherein: (i) Ar$^1$ comprises three or more rings fused together, each ring is an optionally substituted aryl ring or an optionally substituted heteroaryl ring; (ii) R$_1$ at each occurrence is an optionally substituted C$_1$-C$_{50}$ organic group; and (iii) B at each occurrence is independently selected from hydrogen, halogen, cyano, nitro, optionally substituted alkyl group and optionally substituted heteroalkyl group, or a structure wherein each pair of substituents B in ortho position optionally forms a conjugated ring.

2. The compound of claim 1, wherein Ar¹ comprises two or more N heteroatoms.

3. The compound of claim 1, wherein B is hydrogen and Ar¹ is represented by

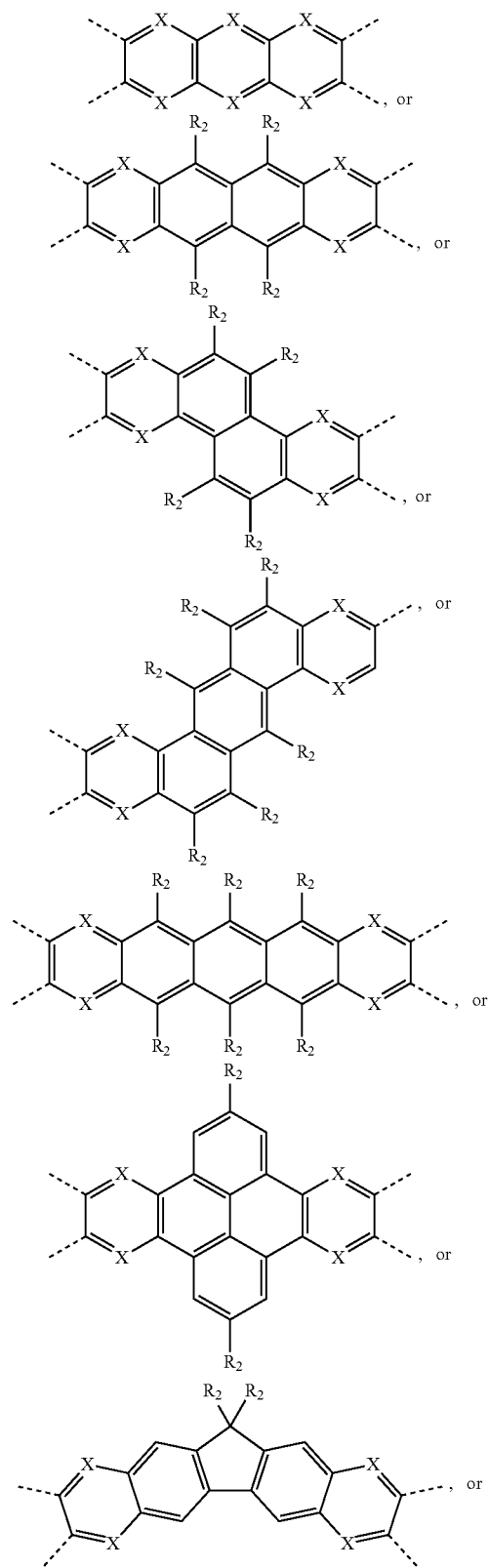

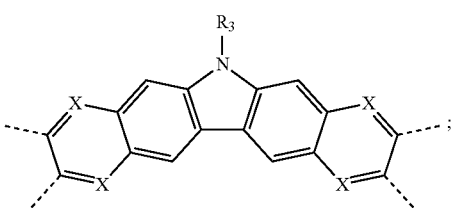

wherein X at each occurrence is independently selected from

and wherein $R_2$ at each occurrence is an end group optionally linked by a single bond or by one or more conjugation side groups; wherein the end group at each occurrence is independently selected from hydrogen, cyano, an optionally substituted $C_1$-$C_{24}$ alkyl group and an optionally substituted $C_1$-$C_{24}$ heteroalkyl group; and wherein the optional conjugation side group at each occurrence is independently selected from an optionally substituted aryl group, an optionally substituted heteroaryl group, an optionally substituted ethenylene, and ethynylene; and wherein $R_3$ is selected from hydrogen, an optionally substituted $C_1$-$C_{24}$ alkyl group and an optionally substituted $C_1$-$C_{24}$ heteroalkyl group.

4. The compound of claim 3, wherein Ar¹ comprises one or more conjugation side groups selected from

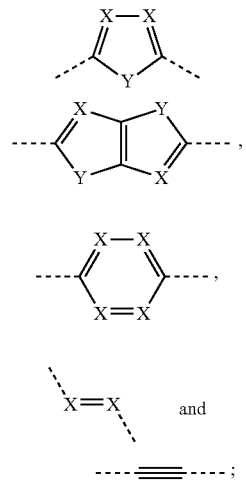

wherein Y at each occurrence is independently selected from O, S, Se, Te, $N(R_3)$, $C(R_3)_2$ and $Si(R_3)_2$.

5. The compound of claim 3, wherein the compound is selected from:

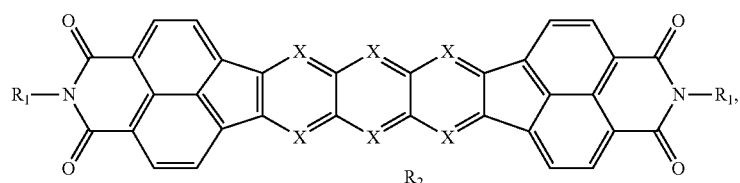
(XII)
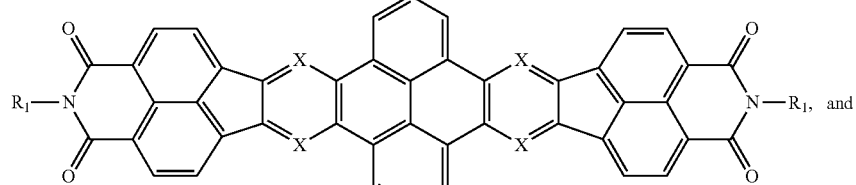
(XIII)
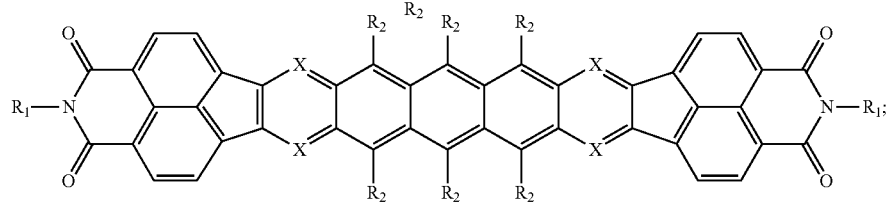
(XIV)
and
wherein the optional conjugation side group is selected from
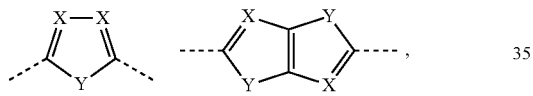
Y at each occurrence is independently selected from O, S, Se, Te, $N(R_3)$, $C(R_3)_2$ and $Si(R_3)_2$.
6. The compound of claim 1, wherein the compound is selected from:
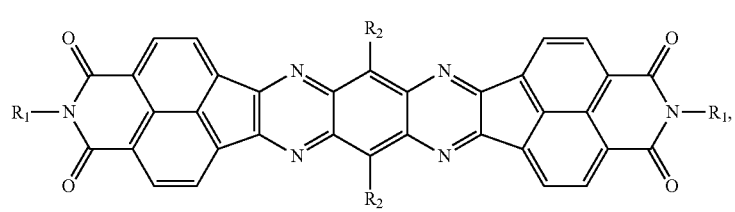
(XV)
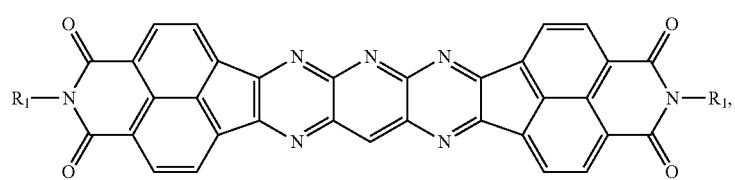
(XVI)
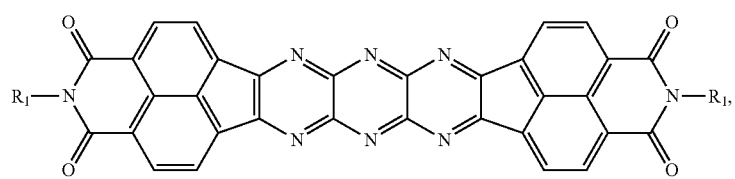
(XVII)

(XVIII)

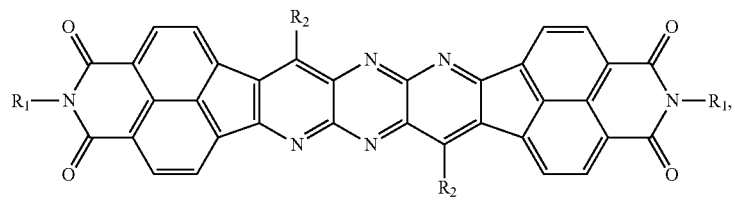

(XIX)

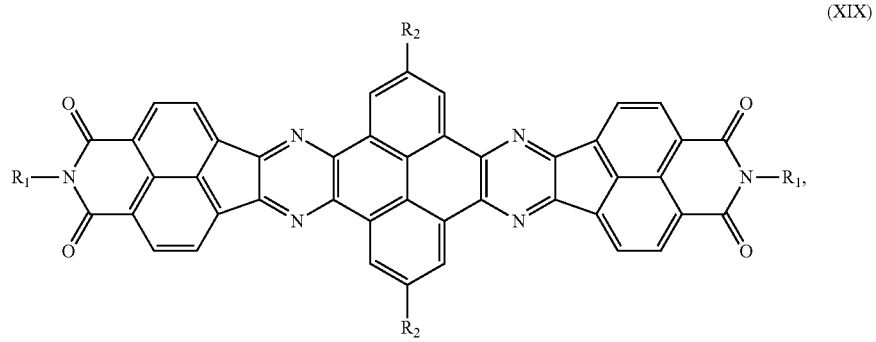

(LXXII)

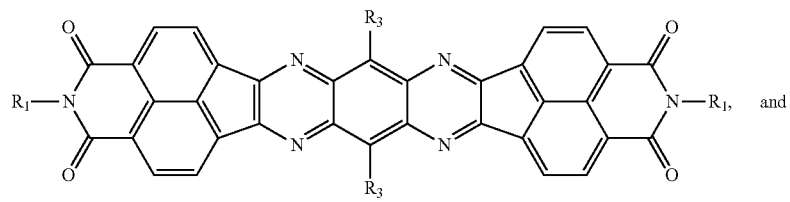

and (LXIX)

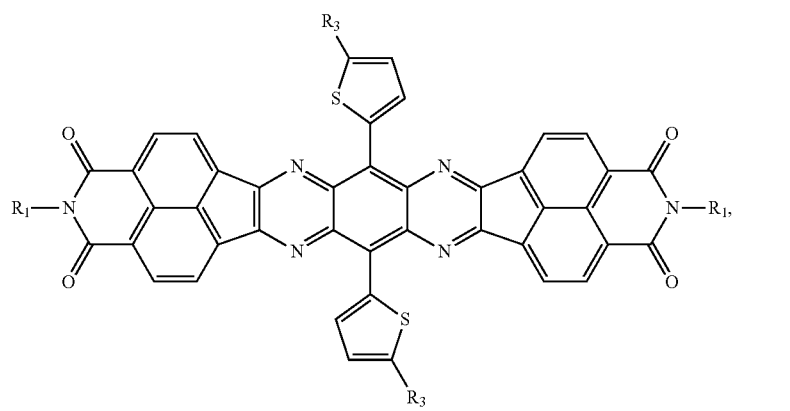

wherein R₃ at each occurrence is independently selected from hydrogen, cyano, an optionally substituted $C_1$-$C_{24}$ alkyl group and an optionally substituted $C_1$-$C_{24}$ heteroalkyl group wherein R₂ at each occurrence is an end group optionally linked by a single bond or by one or more conjugation side groups; wherein the end group at each occurrence is independently selected from hydrogen, cyano, an optionally substituted $C_1$-$C_{24}$ alkyl group and an optionally substituted $C_1$-$C_{24}$ heteroalkyl group; and wherein the optional conjugation side group at each occurrence is independently selected from an optionally substituted aryl group, an optionally substituted heteroaryl group, an optionally substituted ethenylene, and ethynylene.

7. The compound of claim 1, wherein the compound is a monomer suitable for polymerization or copolymerization, and wherein $Ar^1$ comprises one or more halogen atoms that are polymerizable.

8. The compound of claim 7, wherein the compound is represented by formula (XXXIII):

(XXXIII)

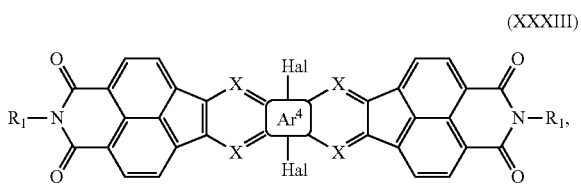

wherein:
(i) $Ar^4$ comprises an optionally substituted aryl ring or an optionally substituted heteroaryl ring, or two or more of said rings fused together;
(ii) Hal at each occurrence comprises a halogen optionally linked by one or more conjugation side groups, wherein the optional conjugation side group at each occurrence is independently selected from an optionally substituted aryl group, an optionally substituted heteroaryl group, an optionally substituted ethenylene, and ethynylene;

(iii) X at each occurrence is independently selected from

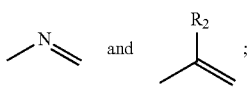

(iv) R$_2$ at each occurrence is an end group optionally linked by a single bond or by one or more conjugation side groups, wherein the end group at each occurrence is independently selected from hydrogen, cyano, an optionally substituted linear or branched C$_1$-C$_{24}$ alkyl group and an optionally substituted linear and branched C$_1$-C$_{24}$ heteroalkyl group.

9. The compound of claim 7, wherein the compound is selected from:

(iii) R$_2$ at each occurrence is an end group optionally linked by a single bond or by one or more conjugation side groups, wherein the end group at each occurrence is independently selected from hydrogen, cyano, an optionally substituted linear or branched C$_1$-C$_{24}$ alkyl group and an optionally substituted linear and branched C$_1$-C$_{24}$ heteroalkyl group; and (iv) the optional conjugation side group at each occurrence is independently selected from

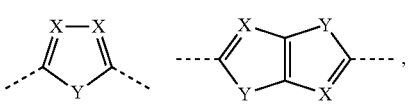

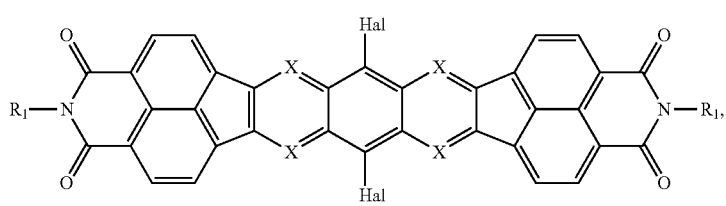

(VIII)

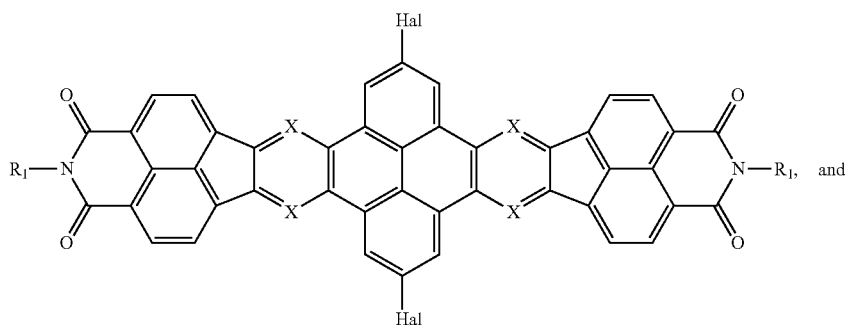

(IX)

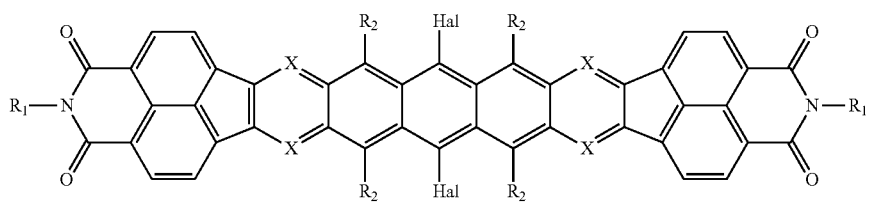

(X)

wherein:
(i) Hal at each occurrence is a halogen optionally linked by a single bond or by one or more conjugation side groups;
(ii) X at each occurrence is independently selected from

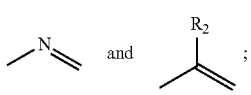

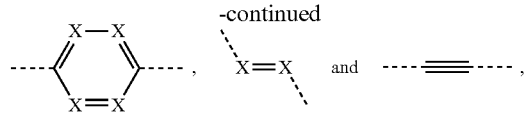

wherein Y at each occurrence is independently selected from O, S, Se, Te, N(R$_3$), C(R$_3$)$_2$ and Si(R$_3$)$_2$, and wherein R$_3$ at each occurrence is independently selected from hydrogen, an optionally substituted linear or branched C$_1$-C$_{24}$ alkyl group and an optionally substituted linear or branched C$_1$-C$_{24}$ heteroalkyl group.

10. The compound of claim 1, wherein the compound is:

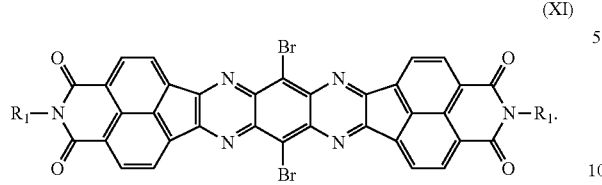
(XI)

11. A composition comprising a compound of claim 1.

12. An electronic or optoelectronic device, comprising a compound of claim 1.

13. An electronic or optoelectronic device, comprising a film obtained by solution processing and annealing a composition, said composition comprising a compound of claim 1.

14. A nanostructure comprising a compound of claim 1.

15. A polymer comprising one or more first repeating units RU1 represented by

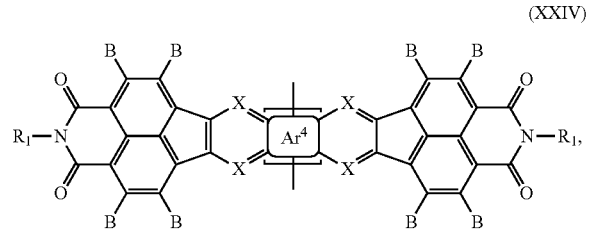
(XXIV)

wherein:

(i) $Ar^4$ comprises an optionally substituted aryl ring or an optionally substituted heteroaryl ring, or two or more of said rings fused together;

(ii) $R_1$ at each occurrence is an optionally substituted $C_1$-$C_{50}$ organic group;

(iii) B at each occurrence is independently selected from hydrogen, halogen, cyano, nitro, optionally substituted alkyl group and optionally substituted heteroalkyl group, or a structure wherein each pair of substituents B in ortho position optionally forms a conjugated ring; and (iv) X at each occurrence is independently selected from

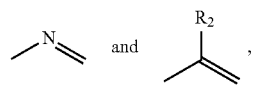

wherein R2 at each occurrence is an end group optionally linked by a single bond or by one or more conjugation side groups, wherein the end group at each occurrence is independently selected from hydrogen, cyano, an optionally substituted $C_1$-$C_{24}$ alkyl group and an optionally substituted $C_1$-$C_{24}$ heteroalkyl group, wherein the optional conjugation side group at each occurrence is independently selected from optionally substituted aryl group, an optionally substituted heteroaryl group, an optionally substituted ethenylene, and ethynylene.

16. The polymer of claim 15, wherein the one or more first repeating units RU1 are selected from

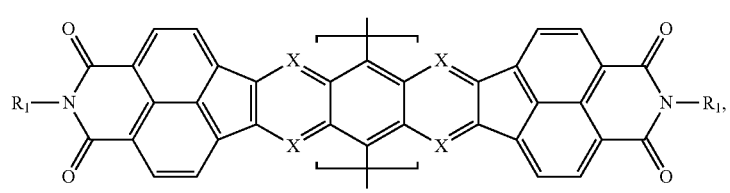
(XXV)

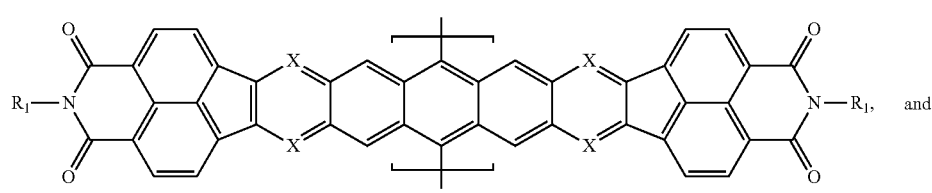
(XXVI)

and

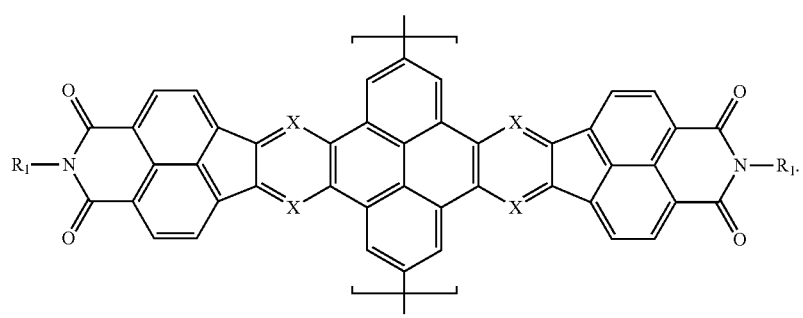
(XXVII)

17. The polymer of claim 15, wherein the polymer is a copolymer further comprising one or more second repeating units RU2 selected from

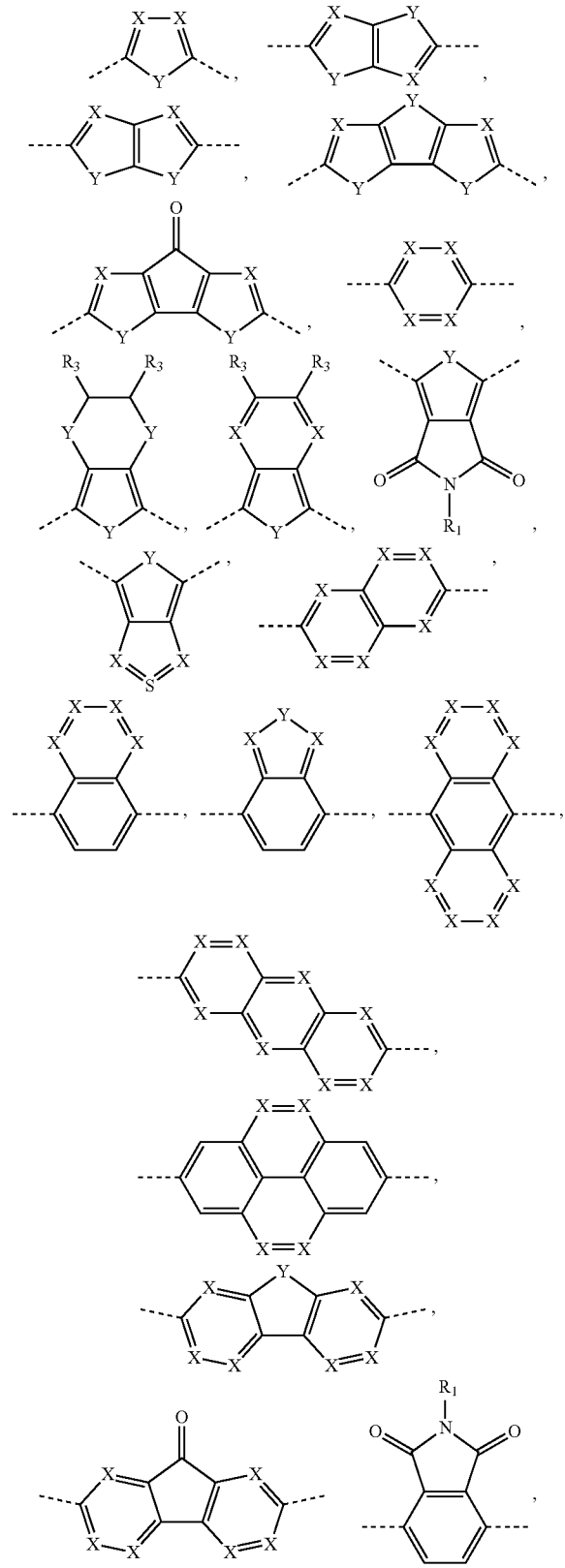

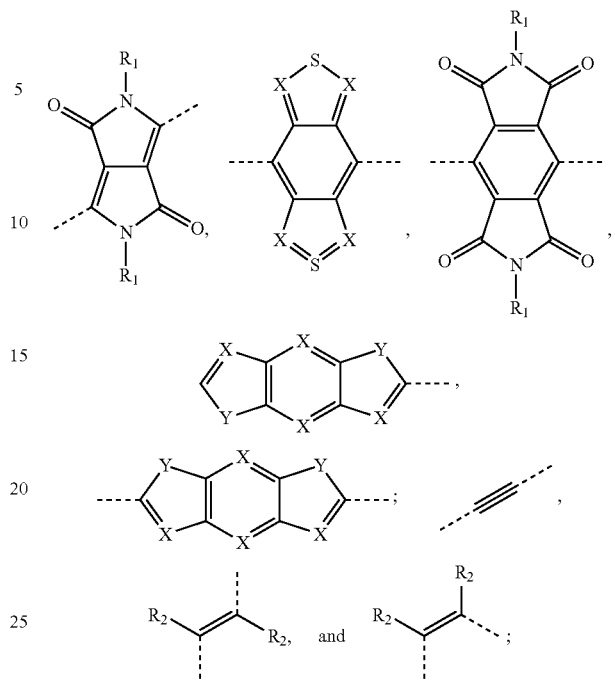

wherein Y at each occurrence is independently selected from O, S, Se, Te, $N(R_3)$, $C(R_3)_2$ and $Si(R_3)_2$; and wherein $R_3$ at each occurrence is independently selected from hydrogen, an optionally substituted linear or branched $C_1$-$C_{24}$ alkyl group and an optionally substituted linear or branched $C_1$-$C_{24}$ heteroalkyl group.

18. The polymer of claim 15, wherein the polymer is selected from

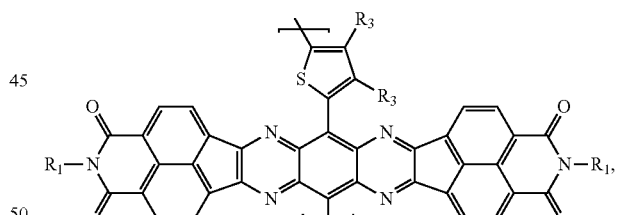

(XXVIII)

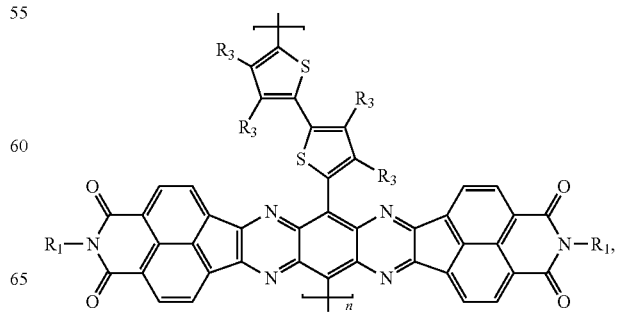

(XXIX)

111
-continued

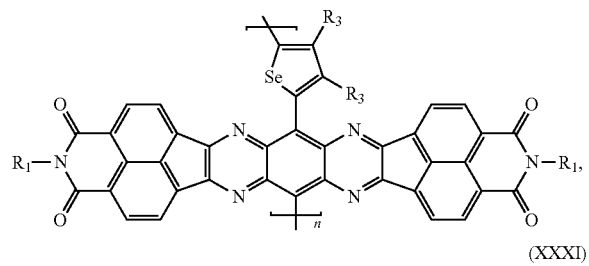

(XXX)

(XXXI)

112
-continued

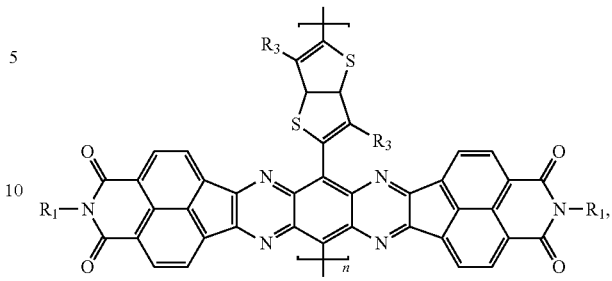

(LXXX)

wherein $R_3$ at each occurrence is independently selected from hydrogen, an optionally substituted linear or branched $C_1$-$C_{24}$ alkyl group and an optionally substituted linear or branched $C_1$-$C_{24}$ heteroalkyl group.

19. A composition comprising at least one polymer of claim 15.

20. An electronic or optoelectronic device, comprising a polymer of claim 15.

21. An electronic or optoelectronic device, comprising a film obtained by solution processing and annealing a composition, said composition comprising a polymer of claim 15.

22. A nanostructure comprising a polymer of claim 15.

* * * * *